United States Patent
McArthur et al.

(10) Patent No.: US 6,413,943 B1
(45) Date of Patent: Jul. 2, 2002

(54) METHODS AND REAGENTS FOR INHIBITING PROLIFERATION OF SMOOTH MUSCLE CELLS

(75) Inventors: James McArthur, San Carlos; Mitchell H. Finer, Woodside, both of CA (US); Jeno Gyuris, Winchester, MA (US)

(73) Assignees: Cell Genesys, Inc., Foster City, CA (US); GPC Biotech Inc., Waltham, MA (US)

( * ) Notice: Subject to any disclaimer, the term of this patent is extended or adjusted under 35 U.S.C. 154(b) by 0 days.

(21) Appl. No.: 09/457,568

(22) Filed: Dec. 9, 1999

Related U.S. Application Data
(60) Provisional application No. 60/122,974, filed on Mar. 1, 1999, and provisional application No. 60/163,382, filed on Nov. 5, 1999.

(51) Int. Cl.[7] .................. A61K 48/00; A61K 35/00; C12N 15/63; C12N 15/85; C07H 21/04

(52) U.S. Cl. ............... 514/44; 435/320.1; 435/325; 435/352; 435/366; 424/93.1; 424/93.21; 536/23.1; 536/23.4

(58) Field of Search .............. 514/44; 424/93.1; 435/320.1, 325, 352, 366; 536/23.1, 23.4

(56) References Cited

U.S. PATENT DOCUMENTS

| | | | | |
|---|---|---|---|---|
| 5,672,508 A | * | 9/1997 | Gyuris et al. | 435/320.1 |
| 6,110,744 A | * | 8/2000 | Fang et al. | 435/456 |

FOREIGN PATENT DOCUMENTS

| | | | |
|---|---|---|---|
| WO | WO9727297 | 7/1997 | |
| WO | WO9903508 | 1/1999 | |
| WO | WO99/06540 | 2/1999 | C12N/15/00 |

OTHER PUBLICATIONS

A Vidal et al., Elsevier Review, "Cell–cycle inhibitors: three families united by a common cause," Gene 247 (2000), 1–15.*

McArthur et al. XP–082144030 p. 603, (1999) "Cancer Gene Therapy with Novel Chimeric p27/p16 Tumor Suppressor Genes."

Biochemical and Biophysical Research Communications, vol. 220, No. 3, pp. 703–709 (1996). Kwon et al., "The cdk2 Binding Domain of p27$^{kip}$ Correlates with the Inhibition of the Kinase Activity of cdk2/Cyclin Complexes."

Lange, MD, R.A. et al. The American Journal of the Medical Sciences vol. 306, No. 4, Oct. 1993, "Southwestern Internal Medicine Conference: Restenosis: The Achilles Heel of Coronary Angioplasty", pp. 265–275.

Kaneda, Y. et al., Annals New York Academy of Sciences 811; "Prevention of Restenosis by Gene Therapy", pp. 299–310.

Fukui, R. et al., Atherosclerosis 132 (1997); Inhibition of smooth muscle cell migration by the p21 cyclin–dependent kinase inhibitor (Cip1); pp. 53–59.

Morisake, H. et al., Biochemical and Biophysical Research Communications 240 (1997); Cell Cycle–Dependent Phosphorylation of p27 Cyclin–Dependent Kinase (Cdk) Inhibitor by Cyclin E/Cdk2, pp. 386–390.

Blais, A. et al., Biochemical and Biophysical Research Communications 247 (1998); "Structure of the Gene Encoding the Human Cyclin–Dependent Kinase Inhibitor p18 and Mutational Analysis in Breast Cancer", pp. 146–153.

(List continued on next page.)

Primary Examiner—James Ketter
Assistant Examiner—Q Janice Li
(74) Attorney, Agent, or Firm—Roylance, Abrams, Berdo & Goodman, L.L.P.

(57) ABSTRACT

Disclosed are methods for using ΔE1/ΔE4 recombinant adenoviruses encoding cyclin dependent kinase inhibitors (CDKi's) as reagents for inhibiting smooth muscle cell proliferation. Also disclosed are recombinant lentiviruses encoding cyclin dependent kinase inhibitors (CDKi's).

26 Claims, 35 Drawing Sheets

OTHER PUBLICATIONS

Jen, J. et al., Cancer Research 56, Dec. 15, 1994; "Deletion of p16 and p15 Genes in Brain Tumors", pp. 6353–6358.

Channon, K.M. et al., Cardiovascular Research 35 (1997); "Efficient adenoviral gene transfer to early venous bypass grafts: comparison with native vessels", pp. 505–513.

Sherr, C. J., Cell, vol. 73, Jun. 18, 1993; "Mammalian G, Cyclins", pp. 1059–1065.

Gyuris, J. et al., Cell vol. 75, Nov. 19, 1993; Cdi1, a Human G1 and S Phase Protein Phosphatase That Associates with Cdk2; pp. 791–803.

Harper, J.W. et al., Cell, vol. 75, Nov. 19, 1993; "The p21 Cdk–Interacting Protein Cip1 is a Potent Inhibitor of G1 Cyclin–Dependent Kinases", pp. 805–816.

Polyak, K. et al., Cell, vol. 78, Jul. 15, 1994; "Cloning of $p27^{kip1}$, a Cyclin–Dependent Kinase Inhibitor and a Potential Mediator of Extracellular Antimitogenic Signals", pp. 59–66.

Yonemitsu, Y. et al., Cir. Res. 82; "Transfer of Wild–Type p53 Gene Effectively Inhibits Vascular Smooth Muscle Cell Proliferation In Vitro and In Vivo", pp. 147–156.

Nomura, H. et al., Gene 191 (1997); "Cloning and Characterization of rat $p27^{kip1}$, a cyclin–dependent kinase inhibitor", pp. 221–218.

Scheaff, R.J. et al., Genes & Development 11, 1997; "Cyclin E–CDK2 is a regulator of $p27^{kip1}$", pp. 1464–1478.

Scherr, C.J. et al., Genes & Development 9, 1995; "Inhibitors of mammalian $G_1$ cyclin–dependent kinases", pp. 1149–1163.

Lee, M.H. et al., Genes & Development 9, 1995; "Cloning of $p57^{kip2}$, a cyclin–dependent kinase inhibitor with unique domain structure and tissue distribution", pp. 639–649.

Matsuoka, S. et al., Genes & Development 9, 1995; "$p57^{kip2}$, a structurally distinct member of the $p21^{cip1}$ Cdk inhibitor family, is a candidate tumor suppressor gene", pp. 650–662.

Chang, M.W. et al., J Clin. Invest. vol. 96, Nov. 1995; "Adenovirus–mediated Over–expression of the Cyclin/Cyclin–dependent Kinase Inhibitor, p21 Inhibits Vascular Smooth Muscle Cell Proliferation and Neointima Formation in the Rat Carotid Artery Model of Balloon Angioplasty", pp. 2260–2268.

Chen, D. et al., J. Clin. Invest. vol. 99, No. 10, May 1997; "Downregulation of Cyclin–dependent Kinase 2 Activity and Cyclin A Promoter Activity in Vascular Smooth Muscle Cells by $p27^{kip1}$, an inhibitor of Neointima Formation in the Rat Carotid Artery", pp. 2334–2341.

Graham, F.L. et al., J. gen. Virol., (1997), 36; "Characteristics of a Human Cell Line Transformed by DNA from Human Adenovirus Type 5", pp. 59–72.

Dull, T. et al., Journal of Virology, vol. 72, No. 11, Nov. 1998; "A Third–Generation Lentivirus Vector with a Conditional Packaging System", pp. 8463–8471.

Guan, K.L. et al., Molecular Biology of the Cell, vol. 7, Jan. 1996; "Isolation and Characterization of $p19^{INK4d}$, a p16–related Inhibitor Specific to CDK6 and CDK4", pp. 57–70.

Susuki, J. et al., Nature Medicine, vol. 3, No. 8, Aug. 1997; "Prevention of graft coronary arteriosclerosis by anisense cdk2 kinase oligonucleotide", pp. 900–903.

Serrano, M. et al., Nature, vol. 366, Dec. 16, 1993; "A new regulatory motif in cell–cycle control causing specific inhibition of cyclin D/CDK4"; pp. 704–707.

Morgan, D.O., Nature, vol. 374, Mar. 9, 1995; "Principles of CDK Regulation", pp. 131–134.

Russo, A.A. et al., Nature, vol. 395, Sep. 17, 1998; "Structural basis for inhibition of the cyclin–dependent kinase Cdk6 by the tumour suppressor $p16^{INK4a}$"; pp. 237–242.

Okamoto, A. et al., Proc. Natl. Acad. Sci. USA, vol. 91, Nov. 1994; "Mutations and altered expression of $p16^{INK4a}$ in human cancer"; pp. 11045–11049.

Yang, Z.Y. et al., Proc. Natl. Acad. Sci. USA, vol. 93, Jul. 1996; "Role of the p21 cyclin–dependent kinase inhibitor in limiting intimal cell proliferation in response to arterial injury", pp. 7905–7910.

Zhang, S. et al., Proc. Natl. Acad. Sci. USA, vol. 95, Mar. 1998; "Cdkn2a, the cyclin–dependent kinase inhibitor encoding $p16^{INK4a}$ and $p19^{ARF}$, is a candidate for the plasmacytoma susceptibility locus, Pctr1"; pp. 2429–2434.

Chang, M.W. et al., Science, vol. 267, Jan. 27, 1995; "Cytostatic Gene Therapy for Vacsular Proliferative Disorders witha Constitutively Active Form of Retinoblastoma Gene Product", pp. 518–522.

Draetta, G., Trends Biochem Science Oct. 15, 1990, "Cell cycle control in eurkaryotes: molecular mechanisms of cdc2 activation"; pp. 378–383.

* cited by examiner

| | | CDK4/ cyclin D1 (nM) | CDK2/ cyclin E (nM) | CDC2/ cyclin B (nM) | HALF-LIFE (HRS) | |
|---|---|---|---|---|---|---|
| | | | | | $G_0$ | As |
| p16 | 1—156 | 100 | >1000 | >1000 | ~3 | ~3 |
| p27 | 1—198 | 23 | 2.4 | 12 | ~3 | ~4.5 |
| Δp27 12-178 | 12—178 | 52 | 11 | 44 | <2 | <1 |
| Δp27 25-93 | 25—93 | 30 | 8.3 | 31 | <1 | <1 |
| W3 | 1—198 2—156 | 17 | 3.0 | 18 | ~2.5 | ~6.5 |
| W4 | 1—198/2—156 | 39 | 8.9 | 15 | | |
| W5 | 1—156 2—198 | 44 | 11 | 18 | | |
| W6 | 1—156/2—198 | 26 | 8.4 | 17 | | |
| W8 | 12—178 2—156 | 23 | 4.4 | 17 | | |
| W7 | 12—178/2—156 | 16 | 2.6 | 9.2 | ~3 | ~20 |
| W10 | 25—93 2—156 | 38 | 3.0 | 17 | | |
| W9 | 25—93/2—156 | 47 | 3.5 | 18 | ~2 | ~4.5 |
| p27 + p16 | 1—156  1—198 | 25 | 1.7 | 12 | | |

FIG. 1

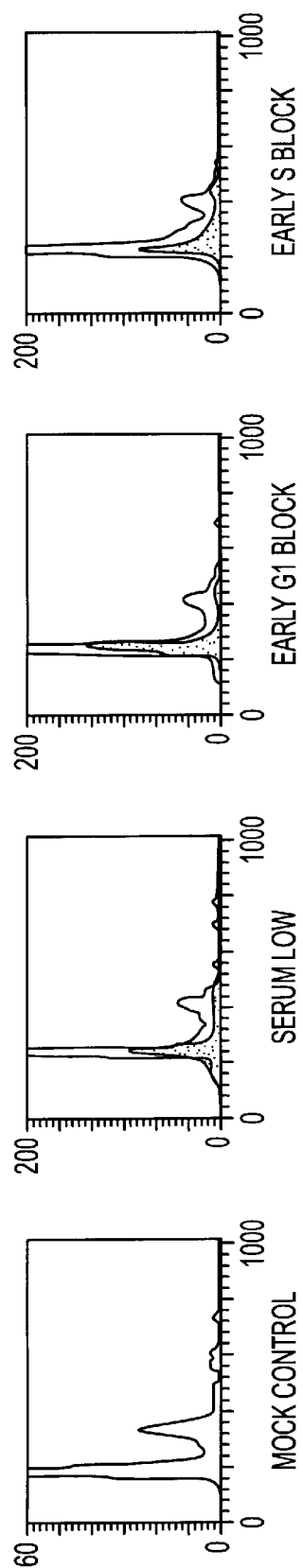

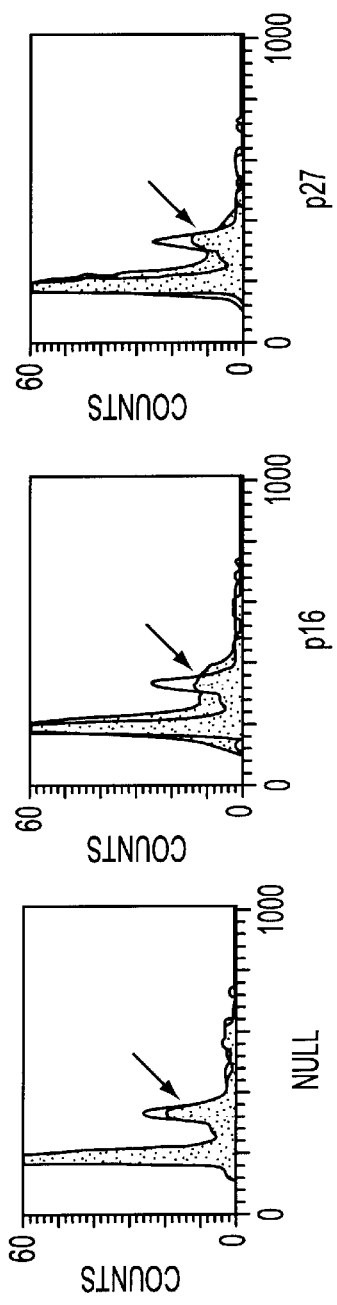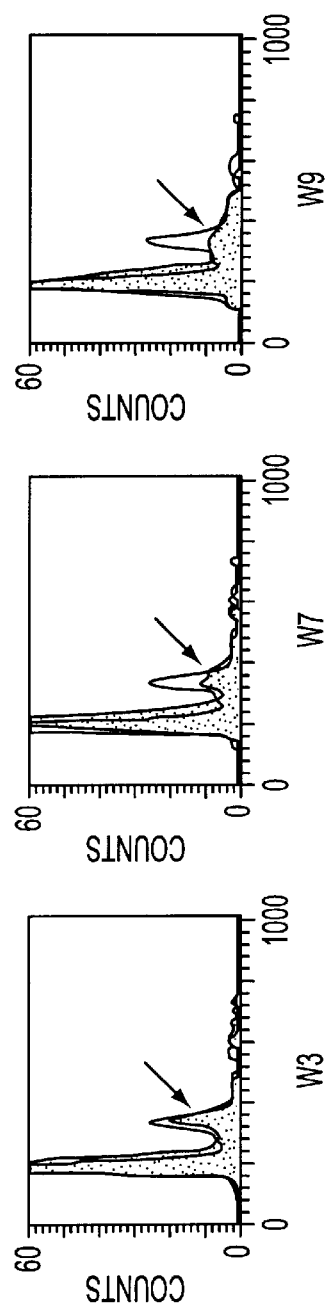

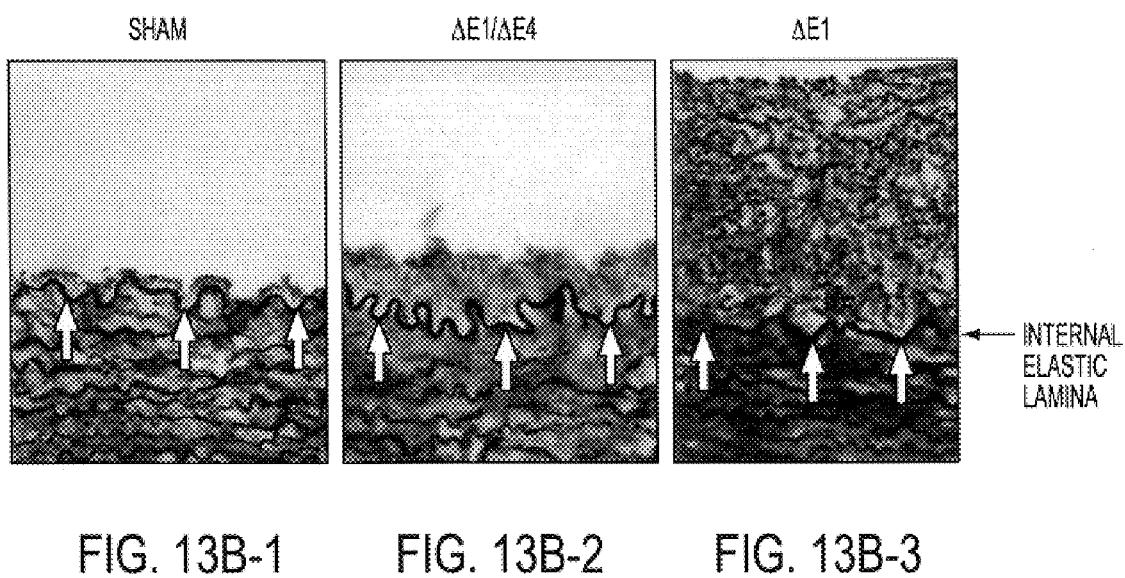

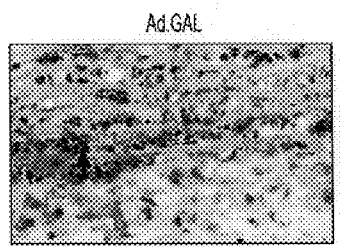 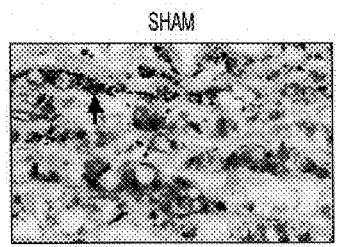 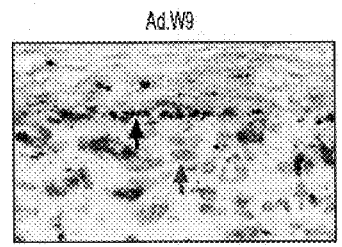
FIG. 18A-7  FIG. 18A-8  FIG. 18A-9

DATA ARE MEAN ± SE; **p<0.01 VS.SHAM CONTROL AND Ad.β-GAL;
++p<0.01 VS.Ad.p16 AND p27

Ad.W9

Ad.p16

Ad.p27

Ad.GAL

SHAM

FIG. 22A-1        FIG. 22A-2 under US 6,413,943 B1

SEQUENCE LISTING

```
<160> NUMBER OF SEQ ID NOS: 28

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 1
gcggccggtc atatgcacca ccatcaccat cactcaaacg tgcgagtgtc t            51

<210> SEQ ID NO 2
<211> LENGTH: 96
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
gccgccggcg tcgactcggc cgaattcgga tccaccccg ccggaaccgc cacccccgct    60
gcccccgcca cccgtttgac gtcttctgag gccagg                             96

<210> SEQ ID NO 3
<211> LENGTH: 1420
<212> TYPE: DNA
<213> ORGANISM: Homo sapiens

<400> SEQUENCE: 3
catatgcacc accatcacca tcactcaaac gtgcgagtgt ctaacgggag ccctagcctg   60
gagcggatgg acgccaggca ggcggagcac cccaagccct cggcctgcag gaacctcttc  120
ggcccggtgg accacgaaga gttaacccgg gacttggaga agcactgcag agacatggaa  180
gaggcgagcc agcgcaagtg gaatttcgat tttcagaatc acaaacccct agagggcaag  240
tacgagtggc aagaggtgga gaagggcagc ttgcccgagt tctactacag accccgcgg   300 ccccccaaag gtgcctgcaa ggtgccggcg caggagagcc aggatgtcag cgggagccgc  360
ccggcggcgc ctttaattgg ggctccggct aactctgagg acacgcattt ggtggaccca  420
aagactgatc cgtcggacag ccagacgggg ttagcggagc aatgcgcagg aataaggaag  480
cgacctgcaa ccgacgattc ttctactcaa aacaaaagag ccaacagaac agaagaaat   540 gtttcagacg gttccccaaa tgccggttct gtggagcaga cgcccaagaa gcctggcctc  600
```

-continued

```
agaagacgtc aaacgggtgg cgggggcagc gggggtggcg gttccggcgg gggtggatcc       660
gaattctgcg ccgcgcgtg cgctcggcgg ctgcggagag gggagagcat gcagcgggcg        720
gcggggagca gcatggagcc ttcggctgac tggctggcca cggccgcggc ccgggtcgg        780 gtagaggagg tgcgggcgct gctggaggcg gtggcgctgc ccaacgcacc gaatagttac      840
ggtcggaggc cgatccaggt catgatgatg gcagcgccc gagtggcgga gctgctgctg       900
ctccacggcg cggagcccaa ctgcgccgac cccgccactc tcacccgacc cgtgcacgac      960
gctgcccggg agggcttcct ggacacgctg gtggtgctgc accggccgg ggcgcggctg      1020 gacgtgcgcg atgcctgggg ccgtctgccc gtggacctgg ctgaggagct gggccatcgc     1080
gatgtcgcac ggtacctgcg cgcggctgcg ggggcacca gaggcagtaa ccatgcccgc      1140
atagatgccg cggaaggtcc ctcagacatc cccgattgaa agaaccagag aggctctgag     1200
aaacctcggg aaacttagat catcagtcac cgaaggtcct acagggccac aactgccccc     1260
gccacaaccc accccgctttt cgtagttttc atttagaaaa tagagctttt aaaaatgtcc    1320
tgccttttaa cgtagatata agccttcccc cactaccgta aatgtccatt tatatcattt     1380
tttatatatt cttataaaaa tgtaaaaaag aaaactcgag                            1420
```

<210> SEQ ID NO 4
<211> LENGTH: 391
<212> TYPE: PRT
<213> ORGANISM: Homo sapiens

<400> SEQUENCE: 4

```
Met His His His His His His Ser Asn Val Arg Val Ser Asn Gly Ser
  1               5                  10                  15

Pro Ser Leu Glu Arg Met Asp Ala Arg Gln Ala Glu His Pro Lys Pro
             20                  25                  30

Ser Ala Cys Arg Asn Leu Phe Gly Pro Val Asp His Glu Glu Leu Thr
         35                  40                  45

Arg Asp Leu Glu Lys His Cys Arg Asp Met Glu Glu Ala Ser Gln Arg
     50                  55                  60

Lys Trp Asn Phe Asp Phe Gln Asn His Lys Pro Leu Glu Gly Lys Tyr
 65                  70                  75                  80

Glu Trp Gln Glu Val Glu Lys Gly Ser Leu Pro Glu Phe Tyr Tyr Arg
                 85                  90                  95

Pro Pro Arg Pro Pro Lys Gly Ala Cys Lys Val Pro Ala Gln Glu Ser
            100                 105                 110

Gln Asp Val Ser Gly Ser Arg Pro Ala Ala Pro Leu Ile Gly Ala Pro
        115                 120                 125

Ala Asn Ser Glu Asp Thr His Leu Val Asp Pro Lys Thr Asp Pro Ser
    130                 135                 140

Asp Ser Gln Thr Gly Leu Ala Glu Gln Cys Ala Gly Ile Arg Lys Arg
145                 150                 155                 160

Pro Ala Thr Asp Asp Ser Ser Thr Gln Asn Lys Arg Ala Asn Arg Thr
                165                 170                 175

Glu Glu Asn Val Ser Asp Gly Ser Pro Asn Ala Gly Ser Val Glu Gln
            180                 185                 190

Thr Pro Lys Lys Pro Gly Leu Arg Arg Arg Gln Thr Gly Gly Gly Gly
        195                 200                 205

Ser Gly Gly Gly Gly Ser Gly Gly Gly Ser Glu Phe Cys Gly Arg
    210                 215                 220
```

-continued

```
Ala Cys Ala Arg Arg Leu Arg Arg Gly Glu Ser Met Gln Arg Ala Ala
225                 230                 235                 240

Gly Ser Ser Met Glu Pro Ser Ala Asp Trp Leu Ala Thr Ala Ala
            245                 250                 255

Arg Gly Arg Val Glu Glu Val Arg Ala Leu Leu Glu Ala Val Ala Leu
                260                 265                 270

Pro Asn Ala Pro Asn Ser Tyr Gly Arg Arg Pro Ile Gln Val Met Met
            275                 280                 285

Met Gly Ser Ala Arg Val Ala Glu Leu Leu Leu Leu His Gly Ala Glu
        290                 295                 300

Pro Asn Cys Ala Asp Pro Ala Thr Leu Thr Arg Pro Val His Asp Ala
305                 310                 315                 320

Ala Arg Glu Gly Phe Leu Asp Thr Leu Val Val Leu His Arg Ala Gly
                325                 330                 335

Ala Arg Leu Asp Val Arg Asp Ala Trp Gly Arg Leu Pro Val Asp Leu
            340                 345                 350

Ala Glu Glu Leu Gly His Arg Asp Val Ala Arg Tyr Leu Arg Ala Ala
                355                 360                 365

Ala Gly Gly Thr Arg Gly Ser Asn His Ala Arg Ile Asp Ala Ala Glu
        370                 375                 380

Gly Pro Ser Asp Ile Pro Asp
385                 390

<210> SEQ ID NO 5
<211> LENGTH: 1121
<212> TYPE: DNA
<213> ORGANISM: Homo sapiens

<400> SEQUENCE: 5
gaattcgccg ccaccatggg ataccttat gatgtgccag attatgcctc aaacgtgcga      60
gtgtctaacg ggcgccctag cctggagcgg atggacgcca ggcaggcgga gcaccccaag     120
ccctcggcct gcaggaacct cttcggcccg gtggaccacg aagagttaac ccggggacttg    180 gagaagcact gcagagacat ggaagaggcg agccagcgca agtggaattt cgattttcag    240
aatcacaaac ccctagaggg caagtacgag tggcaagagg tggagaaggg cagcttgccc    300
gagttctact acagaccccc gcggccccc aaaggtgcct gcaaggtgcc ggcgcaggag     360
agccaggatg tcagcgggag ccgcccggcg gcgcctttaa ttggggctcc ggctaactct    420
gaggacacgc atttggtgga cccaaagact gatccgtcgg agagccagac ggggttagcg    480
gagcaatgcg caggaataag gaagcgacct gcaaccgacg attcttctac tcaaaacaaa    540
agagccaaca gaacagaaga aaatgtttca gacggttccc caaatgccgg ttctgtggag    600
cagacgccca gaagcctggg cctcagaaga cgtcaaacgg tcgaggatcc ggcggcgggg    660
agcagcatgg agccttcggc tgactggctg gccacggccg cggcccgggg tcgggtagag    720
gaggtgcggg cgctgctgga ggcggggcg ctgcccaacg caccgaatag ttacggtcgg     780
aggccgatcc aggtcatgat gatgggcagc gcccgagtgg cggagctgct gctgctccac    840
ggcgcggagc ccaactgcgc cgaccccgcc actctcaccc gacccgtgca cgacgctgcc    900
cgggagggct tcctggacac gctggtggtg ctgcaccggg ccggggcgcg gctggacgtg    960
cgcgatgcct ggggccgtct gcccgtggac ctggctgagg agctgggcca tcgcgatgtc   1020
gcacggtacc tgcgcgcggc tgcgggggc accagaggca gtaaccatgc ccgcatagat   1080
gccgcggaag gtccctcaga catccccgat tgagcggccg c                       1121
```

-continued

```
<210> SEQ ID NO 6
<211> LENGTH: 365
<212> TYPE: PRT
<213> ORGANISM: Homo sapiens

<400> SEQUENCE: 6

Met Gly Tyr Pro Tyr Asp Val Pro Asp Tyr Ala Ser Asn Val Pro Val
 1               5                  10                  15

Ser Asn Gly Arg Pro Ser Leu Glu Arg Met Asp Ala Arg Gln Ala Glu
                20                  25                  30

His Pro Lys Pro Ser Ala Cys Arg Asn Leu Phe Gly Pro Val Asp His
            35                  40                  45

Glu Glu Leu Thr Arg Asp Leu Glu Lys His Cys Arg Asp Met Glu Glu
        50                  55                  60

Ala Ser Gln Arg Lys Trp Asn Phe Asp Phe Gln Asn His Lys Pro Leu
 65                  70                  75                  80

Glu Gly Lys Tyr Glu Trp Gln Glu Val Glu Lys Gly Ser Leu Pro Glu
                85                  90                  95

Phe Tyr Tyr Arg Pro Pro Arg Pro Pro Lys Gly Ala Cys Lys Val Pro
            100                 105                 110

Ala Gln Glu Ser Gln Asp Val Ser Gly Ser Arg Pro Ala Ala Pro Leu
        115                 120                 125

Ile Gly Ala Pro Ala Asn Ser Glu Asp Thr His Leu Val Asp Pro Lys
130                 135                 140

Thr Asp Pro Ser Asp Ser Gln Thr Gly Leu Ala Glu Gln Cys Ala Gly
145                 150                 155                 160

Ile Arg Lys Arg Pro Ala Thr Asp Asp Ser Ser Thr Gln Asn Lys Arg
                165                 170                 175

Ala Asn Arg Thr Glu Glu Asn Val Ser Asp Gly Ser Pro Asn Ala Gly
            180                 185                 190

Ser Val Glu Gln Thr Pro Lys Lys Pro Gly Leu Arg Arg Arg Gln Thr
        195                 200                 205

Val Glu Asp Pro Ala Ala Gly Ser Ser Met Glu Pro Ser Ala Asp Trp
210                 215                 220

Leu Ala Thr Ala Ala Ala Arg Gly Arg Val Glu Glu Val Arg Ala Leu
225                 230                 235                 240

Leu Glu Ala Gly Ala Leu Pro Asn Ala Pro Asn Ser Tyr Gly Arg Arg
                245                 250                 255

Pro Ile Gln Val Met Met Met Gly Ser Ala Arg Val Ala Glu Leu Leu
            260                 265                 270

Leu Leu His Gly Ala Glu Pro Asn Cys Ala Asp Pro Ala Thr Leu Thr
        275                 280                 285

Arg Pro Val His Asp Ala Arg Glu Gly Phe Leu Asp Thr Leu Val
    290                 295                 300

Val Leu His Arg Ala Gly Ala Arg Leu Asp Val Arg Asp Ala Trp Gly
305                 310                 315                 320

Arg Leu Pro Val Asp Leu Ala Glu Glu Leu Gly His Arg Asp Val Ala
                325                 330                 335

Arg Tyr Leu Arg Ala Ala Gly Gly Thr Arg Gly Ser Asn His Ala
            340                 345                 350

Arg Ile Asp Ala Ala Glu Gly Pro Ser Asp Ile Pro Asp
        355                 360                 365

<210> SEQ ID NO 7
```

<211> LENGTH: 1143
<212> TYPE: DNA
<213> ORGANISM: Homo sapiens

<400> SEQUENCE: 7

```
atgggatacc cttatgatgt gccagattat gccgatccgg cggcggggag cagcatggag      60
ccttcggctg actggctggc cacggccgcg gcccggggtc gggtagagga ggtgcgggcg     120
ctgctggagg cggggggcgct gcccaacgca ccgaatagtt acggtcggag gccgatccag    180
gtcatgatga tgggcagcgc ccgagtggcg gagctgctgc tgctccacgg cgcggagccc    240
aactgcgccg accccgccac tctcacccga cccgtgcacg acgctgcccg ggagggcttc    300
ctggacacgc tggtggtgct gcaccgggcc ggggcgcggc tggacgtgcg cgatgcctgg    360
ggccgtctgc ccgtggacct ggctgaggag ctgggccatc gcgatgtcgc acggtacctg    420
cgcgcggctg cgggggggcac cagaggcagt aaccatgccc gcatagatgc gcggaaggt    480
ccctcagaca tccccgatgg tggcggggc agcggggtg gcggttccgg cggggtgga      540
tccgtcgagt caaacgtgcg agtgtctaac gggcgcccta gcctggagcg gatgacgcc    600
aggcaggcgg agcaccccaa gccctcggcc tgcaggaacc tcttcggccc ggtggaccac    660
gaagagttaa cccgggactt ggagaagcac tgcagagaca tggaagaggc gagccagcgc    720
aagtggaatt tcgatttca gaatcacaaa ccctagagg gcaagtacga gtggcaagag     780
gtggagaagg gcagcttgcc cgagttctac tacagacccc gcggcccccc caaaggtgcc    840
tgcaaggtgc cggcgcagga gagccaggat gtcagcggga gccgcccggc ggcgccttta    900
attgggctc cggctaactc tgaggacacg catttggtgg acccaaagac tgatccgtcg    960
gacagccaga cggggttagc ggagcaatgc gcaggaataa ggaagcgacc tgcaaccgac   1020
gattcttcta ctcaaaacaa aagagccaac agaacagaag aaaatgtttc agacggttcc    1080
ccaaatgccg gttctgtgga gcagacgccc aagaagcctg gcctcagaag acgtcaaacg   1140
taa                                                                 1143
```

<210> SEQ ID NO 8
<211> LENGTH: 380
<212> TYPE: PRT
<213> ORGANISM: Homo sapiens

<400> SEQUENCE: 8

```
Met Gly Tyr Pro Tyr Asp Val Pro Asp Tyr Ala Asp Pro Ala Ala Gly
  1               5                  10                  15

Ser Ser Met Glu Pro Ser Ala Asp Trp Leu Ala Thr Ala Ala Arg
             20                  25                  30

Gly Arg Val Glu Glu Val Arg Ala Leu Leu Glu Ala Gly Ala Leu Pro
         35                  40                  45

Asn Ala Pro Asn Ser Tyr Gly Arg Arg Pro Ile Gln Val Met Met Met
     50                  55                  60

Gly Ser Ala Arg Val Ala Glu Leu Leu Leu His Gly Ala Glu Pro
 65                  70                  75                  80

Asn Cys Ala Asp Pro Ala Thr Leu Thr Arg Pro Val His Asp Ala Ala
                 85                  90                  95

Arg Glu Gly Phe Leu Asp Thr Leu Val Val Leu His Arg Ala Gly Ala
            100                 105                 110

Arg Leu Asp Val Arg Asp Ala Trp Gly Arg Leu Pro Val Asp Leu Ala
        115                 120                 125

Glu Glu Leu Gly His Arg Asp Val Ala Arg Tyr Leu Arg Ala Ala Ala
```

```
                130             135             140
Gly Gly Thr Arg Gly Ser Asn His Ala Arg Ile Asp Ala Ala Glu Gly
145                 150                 155                 160

Pro Ser Asp Ile Pro Asp Gly Gly Gly Ser Gly Gly Gly Gly Gly Ser
                165                 170                 175

Gly Gly Gly Gly Ser Val Glu Ser Asn Val Arg Val Ser Asn Gly Arg
            180                 185                 190

Pro Ser Leu Glu Arg Met Asp Ala Arg Gln Ala Glu His Pro Lys Pro
            195                 200                 205

Ser Ala Cys Arg Asn Leu Phe Gly Pro Val Asp His Glu Glu Leu Thr
            210                 215                 220

Arg Asp Leu Glu Lys His Cys Arg Asp Met Glu Glu Ala Ser Gln Arg
225                 230                 235                 240

Lys Trp Asn Phe Asp Phe Gln Asn His Lys Pro Leu Glu Gly Lys Tyr
                245                 250                 255

Glu Trp Gln Glu Val Glu Lys Gly Ser Leu Pro Glu Phe Tyr Tyr Arg
                260                 265                 270

Pro Pro Arg Pro Pro Lys Gly Ala Cys Lys Val Pro Ala Gln Glu Ser
            275                 280                 285

Gln Asp Val Ser Gly Ser Arg Pro Ala Ala Pro Leu Ile Gly Ala Pro
            290                 295                 300

Ala Asn Ser Glu Asp Thr His Leu Val Asp Pro Lys Thr Asp Pro Ser
305                 310                 315                 320

Asp Ser Gln Thr Gly Leu Ala Glu Gln Cys Ala Gly Ile Arg Lys Arg
                325                 330                 335

Pro Ala Thr Asp Asp Ser Ser Thr Gln Asn Lys Arg Ala Asn Arg Thr
                340                 345                 350

Glu Glu Asn Val Ser Asp Gly Ser Pro Asn Ala Gly Ser Val Glu Gln
            355                 360                 365

Thr Pro Lys Lys Pro Gly Leu Arg Arg Arg Gln Thr
        370                 375                 380

<210> SEQ ID NO 9
<211> LENGTH: 1098
<212> TYPE: DNA
<213> ORGANISM: Homo sapiens

<400> SEQUENCE: 9
atgggatacc cttatgatgt gccagattat gccgatccgg cggcggggag cagcatggag      60
ccttcggctg actggctggc cacggccgcg gcccggggtc gggtagagga ggtgcgggcg     120
ctgctggagg cggggcgct gcccaacgca ccgaatagtt acggtcggag gccgatccag     180
gtcatgatga tgggcagcgc ccgagtggcg gagctgctgc tgctccacgg cgcggagccc     240
aactgcgccg accccgccac tctcacccga cccgtgcacg acgctgcccg ggagggcttc     300
ctggacacgc tggtggtgct gcaccgggcc ggggcgcggc tggacgtgcg cgatgcctgg     360
ggccgtctgc ccgtggacct ggctgaggag ctgggccatc gcgatgtcgc acggtacctg     420
cgcgcggctg cgggggcac cagaggcagt aaccatgccc gcatagatgc gcgcggaaggt     480 ccctcagaca tccccgatgt cgagtcaaac gtgcgagtgt ctaacgggcg ccctagcctg     540
gagcggatgg acgccaggca ggcggagcac cccaagccct cggcctgcag gaacctcttc     600 ggccccggtgg accacgaaga gttaacccgg gacttggaga agcactgcag agacatggaa     660
gaggcgagcc agcgcaagtg gaatttcgat tttcagaatc acaaacccct agagggcaag     720
```

```
tacgagtggc aagaggtgga gaagggcagc ttgcccgagt tctactacag acccccgcgg    780 cccccaaag gtgcctgcaa ggtgccggcg caggagagcc aggatgtcag cgggagccgc     840
ccggcggcgc ctttaattgg ggctccggct aactctgagg acacgcattt ggtggaccca    900
aagactgatc cgtcggacag ccagacgggg ttagcggagc aatgcgcagg aataaggaag    960
cgacctgcaa ccgacgattc ttctactcaa aacaaaagag ccaacagaac agaagaaaat   1020
gtttcagacg gttccccaaa tgccggttct gtggagcaga cgcccaagaa gcctggcctc   1080
agaagacgtc aaacgtaa                                                 1098
```

```
<210> SEQ ID NO 10
<211> LENGTH: 365
<212> TYPE: PRT
<213> ORGANISM: Homo sapiens

<400> SEQUENCE: 10

Met Gly Tyr Pro Tyr Asp Val Pro Asp Tyr Ala Asp Pro Ala Ala Gly
  1               5                  10                  15

Ser Ser Met Glu Pro Ser Ala Asp Trp Leu Ala Thr Ala Ala Arg
             20                  25                  30

Gly Arg Val Glu Glu Val Arg Ala Leu Leu Glu Ala Gly Ala Leu Pro
         35                  40                  45

Asn Ala Pro Asn Ser Tyr Gly Arg Arg Pro Ile Gln Val Met Met Met
     50                  55                  60

Gly Ser Ala Arg Val Ala Glu Leu Leu Leu Leu His Gly Ala Glu Pro
 65                  70                  75                  80

Asn Cys Ala Asp Pro Ala Thr Leu Thr Arg Pro Val His Asp Ala Ala
                 85                  90                  95

Arg Glu Gly Phe Leu Asp Thr Leu Val Val Leu His Arg Ala Gly Ala
            100                 105                 110

Arg Leu Asp Val Arg Asp Ala Trp Gly Arg Leu Pro Val Asp Leu Ala
        115                 120                 125

Glu Glu Leu Gly His Arg Asp Val Ala Arg Tyr Leu Arg Ala Ala Ala
    130                 135                 140

Gly Gly Thr Arg Gly Ser Asn His Ala Arg Ile Asp Ala Ala Glu Gly
145                 150                 155                 160

Pro Ser Asp Ile Pro Asp Val Glu Ser Asn Val Arg Val Ser Asn Gly
                165                 170                 175

Arg Pro Ser Leu Glu Arg Met Asp Ala Arg Gln Ala Glu His Pro Lys
            180                 185                 190

Pro Ser Ala Cys Arg Asn Leu Phe Gly Pro Val Asp His Glu Glu Leu
        195                 200                 205

Thr Arg Asp Leu Glu Lys His Cys Arg Asp Met Glu Glu Ala Ser Gln
    210                 215                 220

Arg Lys Trp Asn Phe Asp Phe Gln Asn His Lys Pro Leu Glu Gly Lys
225                 230                 235                 240

Tyr Glu Trp Gln Glu Val Glu Lys Gly Ser Leu Pro Glu Phe Tyr Tyr
                245                 250                 255

Arg Pro Pro Arg Pro Pro Lys Gly Ala Cys Lys Val Pro Ala Gln Glu
            260                 265                 270

Ser Gln Asp Val Ser Gly Ser Arg Pro Ala Ala Pro Leu Ile Gly Ala
        275                 280                 285

Pro Ala Asn Ser Glu Asp Thr His Leu Val Asp Pro Lys Thr Asp Pro
    290                 295                 300
```

```
Ser Asp Ser Gln Thr Gly Leu Ala Glu Gln Cys Ala Gly Ile Arg Lys
305                 310                 315                 320

Arg Pro Ala Thr Asp Ser Ser Thr Gln Asn Lys Arg Ala Asn Arg
            325                 330                 335

Thr Glu Glu Asn Val Ser Asp Gly Ser Pro Asn Ala Gly Ser Val Glu
            340                 345                 350

Gln Thr Pro Lys Lys Pro Gly Leu Arg Arg Arg Gln Thr
            355                 360                 365

<210> SEQ ID NO 11
<211> LENGTH: 557
<212> TYPE: DNA
<213> ORGANISM: Homo sapiens

<400> SEQUENCE: 11
gaattcgccg ccaccatggg ataccttat  gatgtgccag attatgccag cctggagcgg      60
atggacgcca ggcaggcgga gcaccccaag ccctcggcct gcaggaacct cttcggcccg     120
gtggaccacg aagagttaac ccgggacttg gagaagcact gcagagacat ggaagaggcg     180
agccagcgca agtggaattt cgattttcag aatcacaaac ccctagaggg caagtacgag     240
tggcaagagg tggagaaggg cagcttgccc gagttctact acagacccc  gcggcccccc     300 aaaggtgcct gcaaggtgcc ggcgcaggag agccaggatg tcagcgggag ccgcccggcg     360
gcgcctttaa ttggggctcc ggctaactct gaggacacgc atttggtgga cccaaagact     420
gatccgtcgg acagccagac ggggttagcg agcaatgcg  caggaataag gaagcgacct     480
gcaaccgacg attcttctac tcaaaacaaa agagccaaca gaacagaaga aaatgtttca     540
gacggttagg cggccgc                                                    557

<210> SEQ ID NO 12
<211> LENGTH: 177
<212> TYPE: PRT
<213> ORGANISM: Homo sapiens

<400> SEQUENCE: 12

Met Gly Tyr Pro Tyr Asp Val Pro Asp Tyr Ala Ser Leu Glu Arg Met
 1               5                  10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Ser Ser
145                 150                 155                 160

Ser Thr Gln Asn Lys Arg Ala Asn Arg Thr Glu Glu Asn Val Ser Asp
```

165                 170                 175
Gly

<210> SEQ ID NO 13
<211> LENGTH: 1073
<212> TYPE: DNA
<213> ORGANISM: Homo sapiens

<400> SEQUENCE: 13

| | | | | | |
|---|---|---|---|---|---|
| gaattcgccg | ccaccatggg | atacccttat | gatgtgccag | attatgccag | cctggagcgg | 60 |
| atggacgcca | ggcaggcgga | gcaccccaag | ccctcggcct | gcaggaacct | cttcggcccg | 120 |
| gtggaccacg | aagagttaac | ccgggacttg | gagaagcact | gcagagacat | ggaagaggcg | 180 |
| agccagcgca | agtggaattt | cgattttcag | aatcacaaac | ccctagaggg | caagtacgag | 240 |
| tggcaagagg | tggagaaggg | cagcttgccc | gagttctact | acagaccccc | gcggcccccc | 300 |
| aaaggtgcct | gcaaggtgcc | ggcgcaggag | agccaggatg | tcagcgggag | ccgcccggcg | 360 |
| gcgcctttaa | ttgggctcc | ggctaactct | gaggacacgc | atttggtgga | cccaaagact | 420 |
| gatccgtcgg | acagccagac | ggggttagcg | gagcaatgcg | caggaataag | gaagcgacct | 480 |
| gcaaccgacg | attcttctac | tcaaaacaaa | agagccaaca | gaacagaaga | aaatgttca | 540 |
| gacggtggtg | gcggggcag | cggggtggc | ggttccggcg | ggggtggatc | cgtcgaggat | 600 |
| ccggcggcgg | ggagcagcat | ggagccttcg | gctgactggc | tggccacggc | cgcggcccgg | 660 |
| ggtcgggtag | aggaggtgcg | ggcgctgctg | gaggcggggg | cgctgcccaa | cgcaccgaat | 720 |
| agttacggtc | ggaggccgat | ccaggtcatg | atgatgggca | cgcccgagt | ggcggagctg | 780 |
| ctgctgctcc | acgcgcgga | gcccaactgc | gccgaccccg | ccactctcac | ccgacccgtg | 840 |
| cacgacgctg | cccgggaggg | cttcctggac | acgctggtgg | tgctgcaccg | ggccggggcg | 900 |
| cggctggacg | tgcgcgatgc | ctggggccgt | ctgcccgtgg | acctggctga | ggagctgggc | 960 |
| catcgcgatg | tcgcacggta | cctgcgcgcg | gctgcggggg | gcaccagagg | cagtaaccat | 1020 |
| gcccgcatag | atgccgcgga | aggtccctca | gacatccccg | attgagcggc | cgc | 1073 |

<210> SEQ ID NO 14
<211> LENGTH: 348
<212> TYPE: PRT
<213> ORGANISM: Homo sapiens

<400> SEQUENCE: 14

Met Gly Tyr Pro Tyr Asp Val Pro Asp Tyr Ala Ser Leu Glu Arg Met
 1               5                  10                  15

Asp Ala Arg Gln Ala Glu His Pro Lys Pro Ser Ala Cys Arg Asn Leu
             20                  25                  30

Phe Gly Pro Val Asp His Glu Glu Leu Thr Arg Asp Leu Glu Lys His
         35                  40                  45

Cys Arg Asp Met Glu Glu Ala Ser Gln Arg Lys Trp Asn Phe Asp Phe
     50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Pro Arg Pro Pro Lys
                 85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

```
His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Ser
145                 150                 155                 160

Ser Thr Gln Asn Lys Arg Ala Asn Arg Thr Glu Glu Asn Val Ser Asp
                165                 170                 175

Gly Gly Gly Gly Gly Ser Gly Gly Gly Ser Gly Gly Gly Gly Ser
                180                 185                 190

Val Glu Asp Pro Ala Ala Gly Ser Ser Met Glu Pro Ser Ala Asp Trp
            195                 200                 205

Leu Ala Thr Ala Ala Ala Arg Gly Arg Val Glu Glu Val Arg Ala Leu
210                 215                 220

Leu Glu Ala Gly Ala Leu Pro Asn Ala Pro Asn Ser Tyr Gly Arg Arg
225                 230                 235                 240

Pro Ile Gln Val Met Met Met Gly Ser Ala Arg Val Ala Glu Leu Leu
                245                 250                 255

Leu Leu His Gly Ala Glu Pro Asn Cys Ala Asp Pro Ala Thr Leu Thr
            260                 265                 270

Arg Pro Val His Asp Ala Ala Arg Glu Gly Phe Leu Asp Thr Leu Val
            275                 280                 285

Val Leu His Arg Ala Gly Ala Arg Leu Asp Val Arg Asp Ala Trp Gly
    290                 295                 300

Leu Pro Val Asp Leu Ala Glu Glu Leu Gly His Arg Asp Val Ala Arg
305                 310                 315                 320

Tyr Leu Arg Ala Ala Ala Gly Gly Thr Arg Gly Ser Asn His Ala Arg
                325                 330                 335

Ile Asp Ala Ala Glu Gly Pro Ser Asp Ile Pro Asp
            340                 345
```

<210> SEQ ID NO 15
<211> LENGTH: 1028
<212> TYPE: DNA
<213> ORGANISM: Homo sapiens

<400> SEQUENCE: 15

```
gaattcgccg ccaccatggg ataccttat  gatgtgccag attatgccag cctggagcgg      60
atggacgcca ggcaggcgga gcaccccaag ccctcggcct gcaggaacct cttcggcccg     120
gtggaccacg aagagttaac ccgggacttg gagaagcact gcagagacat ggaagaggcg     180
agccagcgca gtggaatttt cgattttcag aatcacaaac ccctagaggg caagtacgag     240 tgcaagagg tggagaaggg cagcttgccc gagttctact acagaccccc gcggcccccc      300
aaaggtgcct gcaaggtgcc ggcgcaggag agccaggatg tcagcgggag ccgcccggcg     360
gcgcctttaa ttgggggctcc ggctaactct gaggacacgc atttggtgga cccaaagact    420
gatccgtcgg acagccagac ggggttagcg agcaatgcg caggaataag gaagcgacct       480
gcaaccgacg attcttctac tcaaaacaaa agagccaaca gaacagaaga aaatgtttca      540
gacggtgtcg aggatccggc ggcggggagc agcatggagc cttcggctga ctggctggcc     600 acggccgcg cccggggtcg ggtagaggag gtgcgggcgc tgctggaggc ggggcgctg       660 cccaacgcac cgaatagtta cggtcggagg ccgatccagg tcatgatgat gggcagcgcc     720 cgagtggcg agctgctgct gctccacggc gcggagccca actgcgccga ccccgccact     780
ctcacccgac ccgtgcacga cgctgcccgg gagggcttcc tggacacgct ggtggtgctg    840
```

```
caccgggccg gggcgcggct ggacgtgcgc gatgcctggg gccgtctgcc cgtggacctg      900
gctgaggagc tgggccatcg cgatgtcgca cggtacctgc gcgcggctgc gggggcacc      960 agaggcagta accatgcccg catagatgcc gcggaaggtc cctcagacat ccccgattga     1020
gcggccgc                                                              1028
```

<210> SEQ ID NO 16
<211> LENGTH: 334
<212> TYPE: PRT
<213> ORGANISM: Homo sapiens

<400> SEQUENCE: 16

```
Met Gly Tyr Pro Tyr Asp Val Pro Asp Tyr Ala Ser Leu Glu Arg Met
 1               5                  10                  15

Asp Ala Arg Gln Ala Glu His Pro Lys Pro Ser Ala Cys Arg Asn Leu
                20                  25                  30

Phe Gly Pro Val Asp His Glu Glu Leu Thr Arg Asp Leu Glu Lys His
            35                  40                  45

Cys Arg Asp Met Glu Glu Ala Ser Gln Arg Lys Trp Asn Phe Asp Phe
        50                  55                  60

Gln Asn His Lys Pro Leu Glu Gly Lys Tyr Glu Trp Gln Val Glu
 65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
                100                 105                 110

Arg Pro Ala Ala Pro Leu Ile Gly Ala Pro Ala Asn Ser Glu Asp Thr
            115                 120                 125

His Leu Val Asp Pro Lys Thr Asp Pro Ser Asp Ser Gln Thr Gly Leu
        130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Val Glu Asp Pro Ala Ala Gly Ser Ser Met Glu Pro Ser Ala Asp
            180                 185                 190

Trp Leu Ala Thr Ala Ala Arg Gly Arg Val Glu Val Arg Ala
        195                 200                 205

Leu Leu Glu Ala Gly Ala Leu Pro Asn Ala Pro Asn Ser Tyr Gly Arg
    210                 215                 220

Arg Pro Ile Gln Val Met Met Met Gly Ser Ala Arg Val Ala Glu Leu
225                 230                 235                 240

Leu Leu Leu His Gly Ala Glu Pro Asn Cys Ala Asp Pro Ala Thr Leu
                245                 250                 255

Thr Arg Pro Val His Asp Ala Ala Arg Glu Gly Phe Leu Asp Thr Leu
            260                 265                 270

Val Val Leu His Arg Ala Gly Ala Arg Leu Asp Val Arg Asp Ala Trp
        275                 280                 285

Gly Arg Leu Pro Val Asp Leu Ala Glu Glu Leu Gly His Arg Asp Val
    290                 295                 300

Ala Arg Tyr Leu Arg Ala Ala Ala Gly Gly Thr Arg Gly Ser Asn His
305                 310                 315                 320

Ala Arg Ile Asp Ala Ala Glu Gly Pro Ser Asp Ile Pro Asp
                325                 330
```

<210> SEQ ID NO 17
<211> LENGTH: 266
<212> TYPE: DNA
<213> ORGANISM: Homo sapiens

<400> SEQUENCE: 17

```
gaattcgccg ccaccatggg atacccttat gatgtgccag attatgccaa gccctcggcc      60
tgcaggaacc tcttcggccc ggtggaccac gaagagttaa cccgggactt ggagaagcac     120
tgcagagaca tggaagaggc gagccagcgc aagtggaatt cgattttca gaatcacaaa      180
cccctagagg gcaagtacga gtggcaagag gtggagaagg gcagcttgcc cgagttctac     240
tacagacccc cgcggtaggc ggccgc                                          266
```

<210> SEQ ID NO 18
<211> LENGTH: 80
<212> TYPE: PRT
<213> ORGANISM: Homo sapiens

<400> SEQUENCE: 18

```
Met Gly Tyr Pro Tyr Asp Val Pro Asp Tyr Ala Lys Pro Ser Ala Cys
 1               5                  10                  15
Arg Asn Leu Phe Gly Pro Val Asp His Glu Glu Leu Thr Arg Asp Leu
                20                  25                  30
Glu Lys His Cys Arg Asp Met Glu Glu Ala Ser Gln Arg Lys Trp Asn
            35                  40                  45
Phe Asp Phe Gln Asn His Lys Pro Leu Glu Gly Lys Tyr Glu Trp Gln
        50                  55                  60
Glu Val Glu Lys Gly Ser Leu Pro Glu Phe Tyr Tyr Arg Pro Pro Arg
    65                  70                  75                  80
```

<210> SEQ ID NO 19
<211> LENGTH: 737
<212> TYPE: DNA
<213> ORGANISM: Homo sapiens

<400> SEQUENCE: 19

```
gaattcgccg ccaccatggg atacccttat gatgtgccag attatgccaa gccctcggcc      60
tgcaggaacc tcttcggccc ggtggaccac gaagagttaa cccgggactt ggagaagcac     120
tgcagagaca tggaagaggc gagccagcgc aagtggaatt cgattttca gaatcacaaa      180
cccctagagg gcaagtacga gtggcaagag gtggagaagg gcagcttgcc cgagttctac     240
tacagacccc cgcgggtcga ggatccggcg gcggggagca gcatggagcc ttcggctgac     300
tggctggcca cggccgcggc ccggggtcgg gtagaggagg tgcgggcgct gctggaggcg     360
ggggcgctgc ccaacgcacc gaatagttac ggtcggaggc cgatccaggt catgatgatg     420
ggcagcgccc gagtggcgga gctgctgctg ctccacggcg cggagcccaa ctgcgccgac     480
cccgccactc tcacccgacc cgtgcacgac gctgcccggg agggcttcct ggacacgcta     540
gtggtgctgc accgggccgg ggcgcggctg gacgtgcgca tgcctggggg ccgtctgccc     600
gtggacctgg ctgaggagct gggccatcgc gatgtcgcac ggtacctgcg cgcggctgcg     660
ggggcacca gaggcagtaa ccatgcccgc atagatgccg cggaaggtcc ctcagacatc     720
cccgattgag cggccgc                                                    737
```

<210> SEQ ID NO 20
<211> LENGTH: 237
<212> TYPE: PRT

<213> ORGANISM: Homo sapiens

<400> SEQUENCE: 20

```
Met Gly Tyr Pro Tyr Asp Val Pro Asp Tyr Ala Lys Pro Ser Ala Cys
 1               5                  10                  15
Arg Asn Leu Phe Gly Pro Val Asp His Glu Glu Leu Thr Arg Asp Leu
             20                  25                  30
Glu Lys His Cys Arg Asp Met Glu Glu Ala Ser Gln Arg Lys Trp Asn
         35                  40                  45
Phe Asp Phe Gln Asn His Lys Pro Leu Glu Gly Lys Tyr Glu Trp Gln
     50                  55                  60
Glu Val Glu Lys Gly Ser Leu Pro Glu Phe Tyr Tyr Arg Pro Pro Arg
 65                  70                  75                  80
Val Glu Asp Pro Ala Ala Gly Ser Ser Met Glu Pro Ser Ala Asp Trp
                 85                  90                  95
Leu Ala Thr Ala Ala Ala Arg Gly Arg Val Glu Val Arg Ala Leu
            100                 105                 110
Leu Glu Ala Gly Ala Leu Pro Asn Ala Pro Asn Ser Tyr Gly Arg Arg
            115                 120                 125
Pro Ile Gln Val Met Met Met Gly Ser Ala Arg Val Ala Glu Leu Leu
    130                 135                 140
Leu Leu His Gly Ala Glu Pro Asn Cys Ala Asp Pro Ala Thr Leu Thr
145                 150                 155                 160
Arg Pro Val His Asp Ala Ala Arg Glu Gly Phe Leu Asp Thr Leu Val
                165                 170                 175
Val Leu His Arg Ala Gly Ala Arg Leu Asp Val Arg Asp Ala Trp Gly
            180                 185                 190
Arg Leu Pro Val Asp Leu Ala Glu Glu Leu Gly His Arg Asp Val Ala
        195                 200                 205
Arg Tyr Leu Arg Ala Ala Ala Gly Gly Thr Arg Gly Ser Asn His Ala
    210                 215                 220
Arg Ile Asp Ala Ala Glu Gly Pro Ser Asp Ile Pro Asp
225                 230                 235
```

<210> SEQ ID NO 21
<211> LENGTH: 782
<212> TYPE: DNA
<213> ORGANISM: Homo sapiens

<400> SEQUENCE: 21

```
gaattcgccg ccaccatggg atacccttat gatgtgccag attatgccaa gccctcggcc      60
tgcaggaacc tcttcggccc ggtggaccac gaagagttaa cccgggactt ggagaagcac     120
tgcagagaca tggaagaggc gagccagcgc aagtggaatt tcgattttca gaatcacaaa     180
cccctagagg gcaagtacga gtggcaagag gtggagaagg gcagcttgcc cgagttctac     240
tacagacccc cgcggggtgg cggggggcagc gggggtggcg gttccggcgg gggtggatcc     300
gtcgaggatc cggcggcggg gagcagcatg gagccttcgg ctgactggct ggccacggcc     360
gcggcccggg gtcgggtaga ggaggtgcgg gcgctgctgg aggcgggggc gctgcccaac     420
gcaccgaata gttacggtcg gaggccgatc caggtcatga tgatgggcag cgcccgagtg     480
gcggagctgc tgctgctcca cggcgcggag cccaactgcg ccgaccccgc cactctcacc     540
cgacccgtgc acgacgctgc ccgggagggc ttcctggaca cgctggtggt gctgcaccgg     600
gccggggcgc ggctggacgt gcgcgatgcc tggggccgtc tgcccgtgga cctggctgag     660
```

```
gagctgggcc atcgcgatgt cgcacggtac ctgcgcgcgg ctgcgggggg caccagaggc    720
agtaaccatg cccgcataga tgccgcggaa ggtccctcag acatccccga ttgagcggcc    780
gc                                                                  782
```

<210> SEQ ID NO 22
<211> LENGTH: 252
<212> TYPE: PRT
<213> ORGANISM: Homo sapiens

<400> SEQUENCE: 22

```
Met Gly Tyr Pro Tyr Asp Val Pro Asp Tyr Ala Lys Pro Ser Ala Cys
 1               5                  10                  15

Arg Asn Leu Phe Gly Pro Val Asp His Glu Glu Leu Thr Arg Asp Leu
            20                  25                  30

Glu Lys His Cys Arg Asp Met Glu Glu Ala Ser Gln Arg Lys Trp Asn
        35                  40                  45

Phe Asp Phe Gln Asn His Lys Pro Leu Glu Gly Lys Tyr Glu Trp Gln
    50                  55                  60

Glu Val Glu Lys Gly Ser Leu Pro Glu Phe Tyr Tyr Arg Pro Pro Arg
65                  70                  75                  80

Gly Gly Gly Gly Ser Gly Gly Gly Ser Gly Gly Gly Ser Val
                85                  90                  95

Glu Asp Pro Ala Ala Gly Ser Ser Met Glu Pro Ser Ala Asp Trp Leu
            100                 105                 110

Ala Thr Ala Ala Ala Arg Gly Arg Val Glu Glu Val Arg Ala Leu Leu
        115                 120                 125

Glu Ala Gly Ala Leu Pro Asn Ala Pro Asn Ser Tyr Gly Arg Arg Pro
    130                 135                 140

Ile Gln Val Met Met Met Gly Ser Ala Arg Val Ala Glu Leu Leu Leu
145                 150                 155                 160

Leu His Gly Ala Glu Pro Asn Cys Ala Asp Pro Ala Thr Leu Thr Arg
                165                 170                 175

Pro Val His Asp Ala Ala Arg Glu Gly Phe Leu Asp Thr Leu Val Val
            180                 185                 190

Leu His Arg Ala Gly Ala Arg Leu Asp Val Arg Asp Ala Trp Gly Arg
        195                 200                 205

Leu Pro Val Asp Leu Ala Glu Glu Leu Gly His Arg Asp Val Ala Arg
    210                 215                 220

Tyr Leu Arg Ala Ala Ala Gly Gly Thr Arg Gly Ser Asn His Ala Arg
225                 230                 235                 240

Ile Asp Ala Ala Glu Gly Pro Ser Asp Ile Pro Asp
                245                 250
```

<210> SEQ ID NO 23
<211> LENGTH: 687
<212> TYPE: DNA
<213> ORGANISM: Homo sapiens

<400> SEQUENCE: 23

```
atggccaagc cctcggcctg caggaacctc ttcggcccgg tggaccacga agagttaacc     60
cgggacttgg agaagcactg cagagacatg gaagaggcga gccagcgcaa gtggaatttc    120
gattttcaga tcacaaaacc cctagagggc aagtacgagt ggcaagaggt ggagaagggc    180
agcttgcccg agttctacta cagaccccg cgggtcgagg atccggcggc ggggagcagc    240
atggagcctt cggctgactg gctggccacg gccgcggccc gggtcgggt agaggaggtg    300
```

```
cgggcgctgc tggaggcggg ggcgctgccc aacgcaccga atagttacgg tcggaggccg      360
atccaggtca tgatgatggg cagcgcccga gtggcggagc tgctgctgct ccacggcgcg      420
gagcccaact gcgccgaccc cgccactctc acccgacccg tgcacgacgc tgcccgggag      480
ggcttcctgg acacgctggt ggtgctgcac cgggccgggg cgcggctgga cgtgcgcgat      540
gcctggggcc gtctgcccgt ggacctggct gaggagctgg gccatcgcga tgtcgcacgg      600
tacctgcgcg cggctgcggg gggcaccaga ggcagtaacc atgcccgcat agatgccgcg      660
gaaggtccct cagacatccc cgattga                                          687

<210> SEQ ID NO 24
<211> LENGTH: 228
<212> TYPE: PRT
<213> ORGANISM: Homo sapiens

<400> SEQUENCE: 24

Met Ala Lys Pro Ser Ala Cys Arg Asn Leu Phe Gly Pro Val Asp His
  1               5                  10                  15

Glu Glu Leu Thr Arg Asp Leu Glu Lys His Cys Arg Asp Met Glu Glu
             20                  25                  30

Ala Ser Gln Arg Lys Trp Asn Phe Asp Phe Gln Asn His Lys Pro Leu
         35                  40                  45

Glu Gly Lys Tyr Glu Trp Gln Glu Val Glu Lys Gly Ser Leu Pro Glu
     50                  55                  60

Phe Tyr Tyr Arg Pro Pro Arg Val Glu Asp Pro Ala Ala Gly Ser Ser
 65                  70                  75                  80

Met Glu Pro Ser Ala Asp Trp Leu Ala Thr Ala Ala Arg Gly Arg
                 85                  90                  95

Val Glu Glu Val Arg Ala Leu Leu Glu Ala Gly Ala Leu Pro Asn Ala
                100                 105                 110

Pro Asn Ser Tyr Gly Arg Arg Pro Ile Gln Val Met Met Met Gly Ser
            115                 120                 125

Ala Arg Val Ala Glu Leu Leu Leu Leu His Gly Ala Glu Pro Asn Cys
        130                 135                 140

Ala Asp Pro Ala Thr Leu Thr Arg Pro Val His Asp Ala Ala Arg Glu
145                 150                 155                 160

Gly Phe Leu Asp Thr Leu Val Val Leu His Arg Ala Gly Ala Arg Leu
                165                 170                 175

Asp Val Arg Asp Ala Trp Gly Arg Leu Pro Val Asp Leu Ala Glu Glu
            180                 185                 190

Leu Gly His Arg Asp Val Ala Arg Tyr Leu Arg Ala Ala Ala Gly Gly
        195                 200                 205

Thr Arg Gly Ser Asn His Ala Arg Ile Asp Ala Ala Glu Gly Pro Ser
    210                 215                 220

Asp Ile Pro Asp
225

<210> SEQ ID NO 25
<211> LENGTH: 597
<212> TYPE: DNA
<213> ORGANISM: Homo sapiens

<400> SEQUENCE: 25
atgtcaaacg tgcgagtgtc taacgggagc cctagcctgg agcggatgga cgccaggcag      60
gcggagcacc ccaagccctc ggcctgcagg aacctcttcg gccggtgga ccacgaagag      120
```

```
ttaacccggg acttggagaa gcactgcaga gacatggaag aggcgagcca gcgcaagtgg      180
aatttcgatt ttcagaatca caaacccta gagggcaagt acgagtggca agaggtggag       240
aagggcagct tgcccgagtt ctactacaga ccccccgcggc cccccaaagg tgcctgcaag     300
gtgccggcgc aggagagcca ggatgtcagc gggagccgcc cggcggcgcc tttaattggg      360
gctccggcta actctgagga cacgcatttg gtggacccaa agactgatcc gtcggacagc      420 cagacgggt tagcggagca atgcgcagga ataaggaagc gacctgcaac cgacgattct       480
tctactcaaa acaaaagagc caacagaaca gaagaaaatg tttcagacgg ttccccaaat      540
gccggttctg tggagcagac gcccaagaag cctggcctca gaagacgtca aacgtaa         597
```

<210> SEQ ID NO 26
<211> LENGTH: 198
<212> TYPE: PRT
<213> ORGANISM: Homo sapiens

<400> SEQUENCE: 26

```
Met Ser Asn Val Arg Val Ser Asn Gly Ser Pro Ser Leu Glu Arg Met
  1               5                  10                  15

Asp Ala Arg Gln Ala Glu His Pro Lys Pro Ser Ala Cys Arg Asn Leu
             20                  25                  30

Phe Gly Pro Val Asp His Glu Glu Leu Thr Arg Asp Leu Glu Lys His
         35                  40                  45

Cys Arg Asp Met Glu Glu Ala Ser Gln Arg Lys Trp Asn Phe Asp Phe
     50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Pro Arg Pro Pro Lys
                 85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195
```

<210> SEQ ID NO 27
<211> LENGTH: 987
<212> TYPE: DNA
<213> ORGANISM: Homo sapiens

<400> SEQUENCE: 27

```
cggagagggg gagaacagac aacgggcggc ggggagcagc atggagccgg cggcggggag       60
cagcatggag ccttcggctg actggctgga cacggccgcg gccgggggtc gggtagagga      120
ggtgcgggcg ctgctggagg cggggggcgct gcccaacgca ccgaatagtt acggtcggag     180
gccgatccag gtcatgatga tgggcagcgc ccgagtggcg gagctgctgc tgctccacgg      240
```

```
cgcggagccc aactgcgccg accccgccac tctcacccga cccgtgcacg acgctgcccg    300
ggagggcttc ctggacacgc tggtggtgct gcaccgggcc ggggcgcggc tggacgtgcg    360
cgatgcctgg ggccgtctgc ccgtggacct ggctgaggag ctgggccatc gcgatgtcgc    420
acggtacctg cgcgcggctg cgggggggcac cagaggcagt aaccatgccc gcatagatgc    480
cgcggaaggt ccctcagaca tccccgattg aaagaaccag agaggctctg agaaacctcg    540
ggaaacttag atcatcagtc accgaaggtc ctacagggcc acaactgccc ccgccacaac    600 ccacccgct ttcgtagttt tcatttagaa aatagagctt ttaaaaatgt cctgccttt     660 aacgtagata taagccttcc cccactaccg taaatgtcca tttatatcat tttttatata    720
ttcttataaa aatgtaaaaa agaaaaacac cgcttctgcc ttttcactgt gttggagttt    780
tctggagtga gcactcacgc cctaagcgca cattcatgtg ggcatttctt gcgagcctcg    840
cagcctccgg aagctgtcga cttcatgaca agcattttgt gaactaggga agctcagggg    900
ggttactggc ttctcttgag tcacactgct agcaaatggc agaaccaaag ctcaaataaa    960
aataaaataa ttttcattca ttcactc                                       987
```

<210> SEQ ID NO 28
<211> LENGTH: 156
<212> TYPE: PRT
<213> ORGANISM: Homo sapiens

<400> SEQUENCE: 28

```
Met Glu Pro Ala Ala Gly Ser Ser Met Glu Pro Ser Ala Asp Trp Leu
 1               5                  10                  15

Ala Thr Ala Ala Ala Arg Gly Arg Val Glu Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
    50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
        115                 120                 125

Tyr Leu Arg Ala Ala Gly Gly Thr Arg Gly Ser Asn His Ala Arg
    130                 135                 140

Ile Asp Ala Ala Glu Gly Pro Ser Asp Ile Pro Asp
145                 150                 155
```

METHODS AND REAGENTS FOR INHIBITING PROLIFERATION OF SMOOTH MUSCLE CELLS

This application claims benefit of U.S. Ser. No. 60/122, 974 filed Mar. 1, 1999 and of U.S. Ser. No. 60/163,382 filed Nov. 5, 1999.

BACKGROUND OF THE INVENTION

1. Field of the Invention

This invention relates to the inhibition of smooth muscle cell proliferation, particularly vascular smooth muscle cell proliferation following injury to a blood vessel from stenting of a blood vessel, angioplasty, or engraftment of a vein onto the arterial system.

2. Summary of the Related Art

Several disease phenotypes, including cancer, rheumatoid arthritis, macular degeneration, and restenosis (e.g., restenosis induced by angioplasty), involve the hyper-proliferation of cells. Cyclin-dependent kinase (CDK) complexes play a key role in the eukaryotic cell cycle (Draetta G. (1990) *Trends Biochem. Sci.* 15: 378–383; Sherr, C. J. (1993) *Cell* 73: 1059–1065). The CDK complex activity is regulated by mechanisms such as stimulatory or inhibitory phosphorylations, as well as the synthesis and degradation of the kinase and cyclin subunit themselves. While $p21^{Waf1/Cip1}$ and $p27^{Kip1}$ inhibit all the CDK/cyclin complexes tested, $p16^{Ink4/MTS1}$, p15, p18, and p19 block exclusively the activity of the CDK4/cyclin D and CDK6/cyclin D complexes in the early $G_1$ phase by either preventing the interaction of CDK4 and Cyclin D1, or indirectly preventing catalysis (Serrano et al. (1993) *Nature* 366: 704–707).

Gene therapy offers the opportunity to prevent the disease pathology. In patients with occlusion of the coronary and/or peripheral vasculature, one of the leading treatments is disassociation of the atherosclerotic plaque through angioplasty. In response to angioplasty, the normal vessel architecture is disrupted and a complex cascade of events takes place, concluding with the hyper-proliferation of the vascular smooth muscle cells and eventual reocclusion of the vessel in approximately 30% of patients (Lange et al. (1993) *Am. J. Med. Sci.* 306:265–275).

Vein grafts are also used as a conduit for peripheral and aurotocoronary bypass grafting. However, more than 50% of coronary veinous bypass grafts fail within 10 years of implantation, often due to restenosis and intimal hyperplasia, which results from undesired smooth muscle cell proliferation (Channon et al. (1997) *Cardiovascular Research* 35:505–513). Antiplatelet agents have had limited impact in reducing vein graft failure (Channon et al., supra).

Stent placement, a procedure for the prevention of immediate vessel closure or elastic rebound following angioplasty, where a stent is placed into a blood vessel, also causes injury to the blood vessel, which can promote restenosis.

Several groups have demonstrated that over-expression of the $p21^{Waf1/CiP1}$, $p27^{Kip1}$, p53, or Rb genes, or cdc-2 and cdk-2 anti-sense genes in the cells at the site of vessel injury will inhibit the hyper-proliferation of vascular smooth muscle cells induced by balloon injury (Chang et al. (1995) *J. Clin. Invest.* 96:2260–2268; Fukui et al. (1997) *Atherosclerosis* 132:53–59; Chen et al. (1997) *J. Clin. Invest.* 99:2334–2341; Chang et al. (1995) *Science* 267:518–522; Yang et al (1996) *Proc. Natl. Acad. Sci.* (*USA*) 93:7905–7910; Yonemitsu et al. (1998) *Circ. Res.* 82:147–156; Kaneda et al. (1997) *Ann. N.Y. Acad. Sci.* 811:308–310; Suzuki et al. (1997) *Nat. Med.* 8:900–903). However, the efficiency of intra-vascular gene therapy in patients may limit over-expression of these cell cycle regulators.

Therefore, there still exists a need for very potent antiproliferative reagents to reduce undesired smooth muscle cell proliferation while overcoming the shortcomings of known cell proliferation-inhibiting reagents. Such novel reagents and methods for using them are useful for treating conditions associated with smooth muscle cell proliferation including, without limitation, restenosis due to angioplasty, stent placement, or vein engraftment.

BRIEF SUMMARY OF THE INVENTION

The invention provides methods and reagents for inhibiting hyperproliferation of smooth muscle cells. The invention provides treatments for vascular pathologies associated with smooth muscle cell hyperproliferation, including restenosis. Preferably, the invention provides methods and reagents for inhibiting vascular smooth muscle cell hyperproliferation in restenosis following angioplasty, stent placement, or vein engraftment.

It has been discovered that cyclin dependent kinase inhibitors (CDKi's) can inhibit smooth muscle cell proliferation. This discovery has been exploited to develop the present invention which, in a first aspect, provides a method for inhibiting smooth muscle cell hyperproliferation comprising transducing smooth muscle cells with an effective amount of a recombinant adenovirus that lacks a functional E4 region and a functional E1 region and that comprises a transgene encoding a cyclin dependent kinase inhibitor (CDKi), wherein hyperproliferation of the transduced smooth muscle cells is inhibited. In certain embodiments of the first aspect of the invention, the cyclin dependent kinase inhibitor is selected from the group consisting of a protein from the INK4 family or an active fragment thereof; a protein from the CIP/KIP family or an active fragment thereof; and a fusion protein comprising at least an active fragment of the protein from the INK4 family and at least an active fragment of the protein from the CIP/KIP family.

In certain embodiments of the first aspect of the invention, the cyclin dependent kinase inhibitor is a protein from the CIP/KIP family of CDKi's. In certain embodiments, the CDKi is a human p27 protein (SEQ ID NO:26) or an active fragment thereof, such as an active fragment selected from the group consisting of amino acids 25–93 of p27 protein and amino acids 12–178 of p27 protein.

In certain embodiments of the first aspect of the invention, the cyclin dependent kinase inhibitor is a protein from the INK4 family of CDKi's. In certain embodiments, the cyclin dependent kinase inhibitor is a human p16 protein (SEQ ID NO:28) or an active fragment thereof.

In certain preferred embodiments of the first aspect of the invention, the cyclin dependent kinase inhibitor is derived from a mammal (e.g., a human).

In certain preferred embodiments of the first aspect of the invention, where the cyclin dependent kinase inhibitor is a fusion protein comprising at least an active fragment of a protein from the INK4 family of CDKi's and at least an active fragment of a protein from the CIP/KIP family of CDKi's, the protein from the INK4 family of CDKi's is human p16 and the protein from the CIP/KIP family of CDKi's is human p27. In other embodiments, the cyclin dependent kinase inhibitor a fusion protein comprising an active fragment of human p27 and an active fragment of human p16, and is W3 (SEQ ID NO:4), W4 (SEQ ID NO:6), W5 (SEQ ID NO:8), W6 (SEQ ID NO:10), W7 (SEQ ID NO:14), W8 (SEQ ID NO16), W9 (SEQ ID NO:20), or W10 (SEQ ID NO:22). In preferred embodiments, the dependent kinase inhibitor is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

In various embodiments of the first aspect of the invention, the recombinant adenovirus additionally lacks a functional E2 region, or a functional E3 region. In preferred embodiments, the recombinant adenovirus is replication-deficient.

In some embodiments of the first aspect of the invention, the smooth muscle cells are cultured smooth muscle cells. In certain embodiments the smooth muscle cells are in a mammal. In certain embodiments, the smooth muscle cells were induced to hyperproliferate by vascular injury. In certain embodiments, the injury was induced by angioplasty, stent placement, or vein engraftment.

In a second aspect, the invention provides a recombinant lentivirus that comprises a transgene encoding a cyclin dependent kinase inhibitor (CDKi). In certain embodiments, the cyclin dependent kinase inhibitor is selected from the group consisting of a protein from the INK4 family or an active fragment thereof; a protein from the CIP/KIP family or an active fragment thereof; and a fusion protein comprising at least an active fragment of the protein from the INK4 family and at least an active fragment of the protein from the CIP/KIP family.

In certain embodiments of the second aspect of the invention, the cyclin dependent kinase inhibitor is a protein from the CIP/KIP family of CDKi's. In certain embodiments, the CDKi is a human p27 protein or an active fragment thereof, such as an active fragment selected from the group consisting of amino acids 25–93 of p27 protein and amino acids 12–178 of p27 protein.

In certain embodiments of the second aspect of the invention, the cyclin dependent kinase inhibitor is a protein from the INK4 family of CDKi's. In certain embodiment, the cyclin dependent kinase inhibitor is a human p16 protein or an active fragment thereof.

In certain preferred embodiment of the second aspect of the invention, where the cyclin dependent kinase inhibitor is a fusion protein comprising at least an active fragment of a protein from the INK4 family of CDKi's and at least an active fragment of a protein from the CIP/KIP family of CDKi's, the protein from the INK4 family of CDKi's is human p16 and the protein from the CIP/KIP family of CDKi's is human p27. In other embodiments, the cyclin dependent kinase inhibitor a fusion protein comprising an active fragment of human p27 and an active fragment of human p16, and is W7 or W9. In a particularly preferred embodiment, the cyclin dependent kinase inhibitor is W9.

In preferred embodiments of the second aspect of the invention, the recombinant lentivirus is replication-deficient.

In a third aspect, the invention provides a therapeutic composition comprising a pharmaceutically acceptable carrier and a recombinant lentivirus that comprises a transgene encoding a cyclin dependent kinase inhibitor. In preferred embodiments, the recombinant lentivirus is replication-deficient.

In a fourth aspect, the invention provides a method for treating a condition associated with smooth muscle cell hyperproliferation comprising administering to a patient having or suspected of having the condition, a therapeutically effective amount of a therapeutic composition comprising a pharmaceutically acceptable carrier and a recombinant lentivirus that comprises a transgene encoding a cyclin dependent kinase inhibitor, wherein the condition is inhibited. In preferred embodiments, the recombinant lentivirus is replication-deficient.

In various embodiments of the fourth aspect of the invention, the condition is restenosis. In certain embodiments, the restenosis is induced by injury. In certain embodiments, the injury is induced by angioplasty, stent placement, or vein engraftment.

BRIEF DESCRIPTION OF THE DRAWINGS

The foregoing and other objects of the present invention, the various features thereof, as well as the invention itself may be more fully understood from the following description, when read together with the accompanying drawings in which.

Figure 5A:
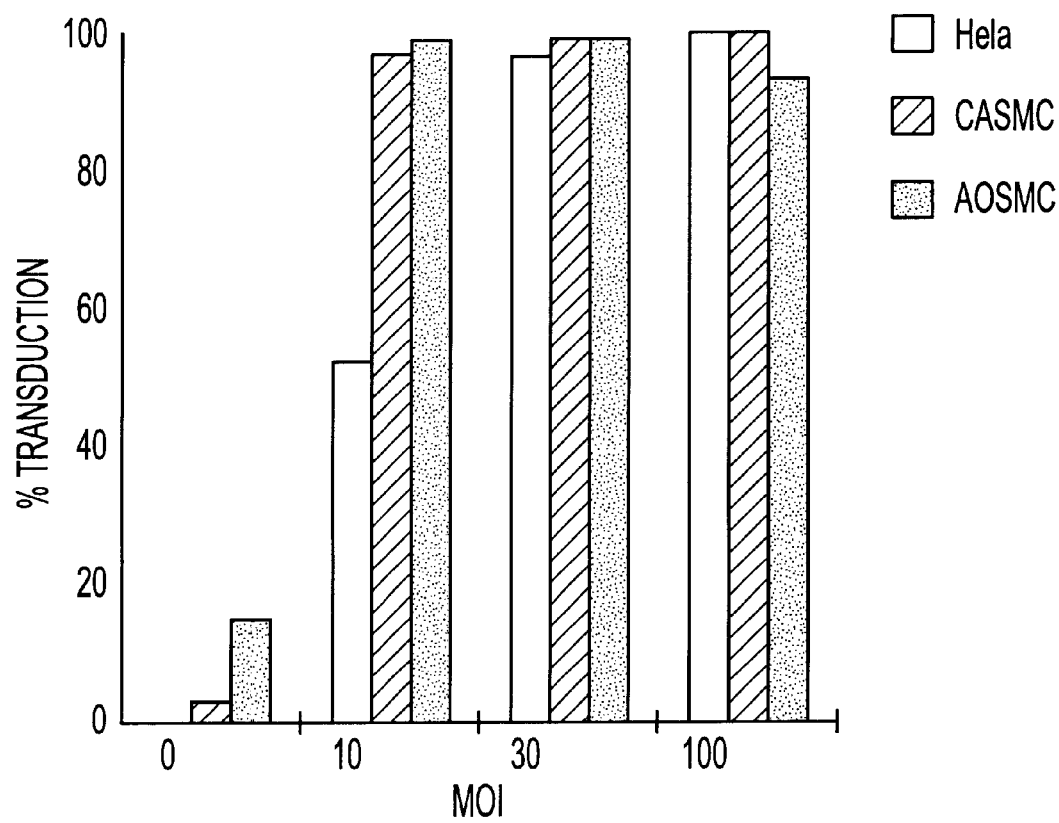
Figure 5B:
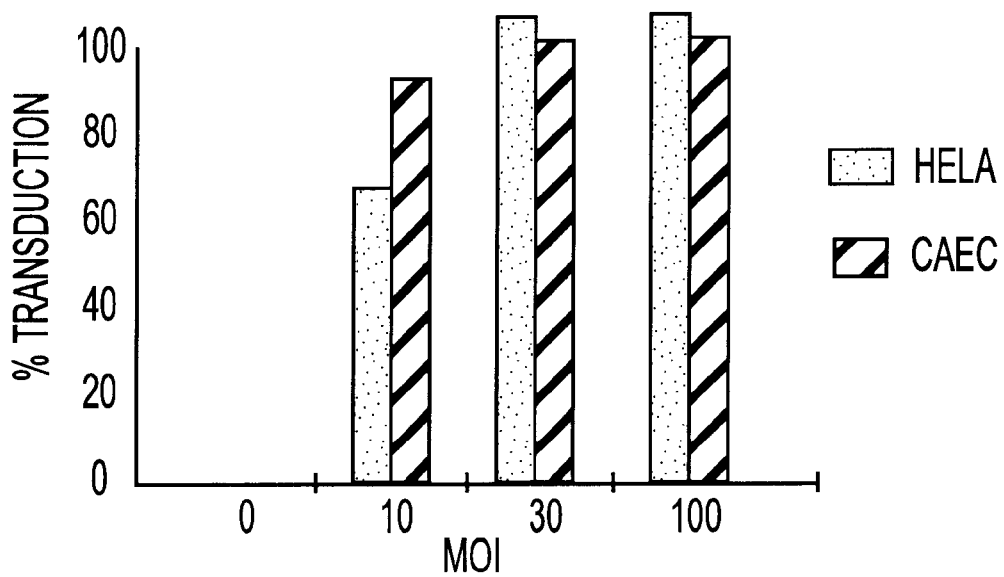
Figure 6:
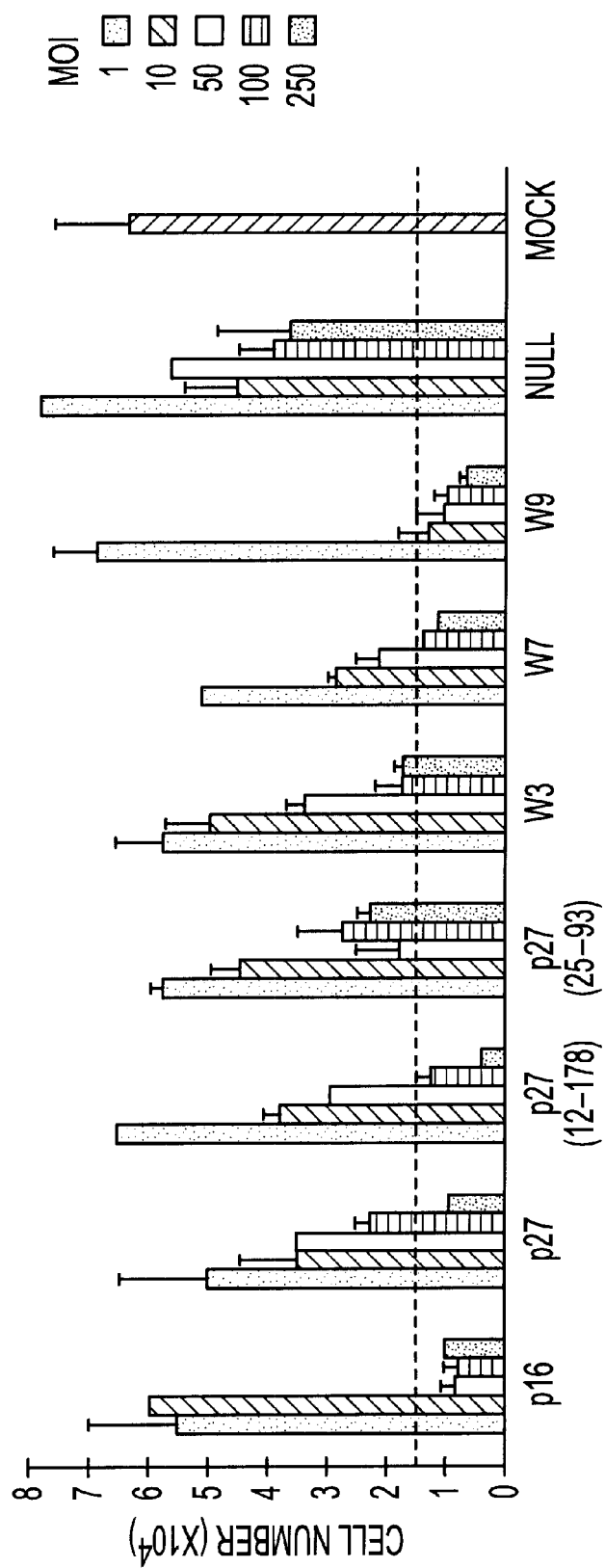
Figures 1, 7B:
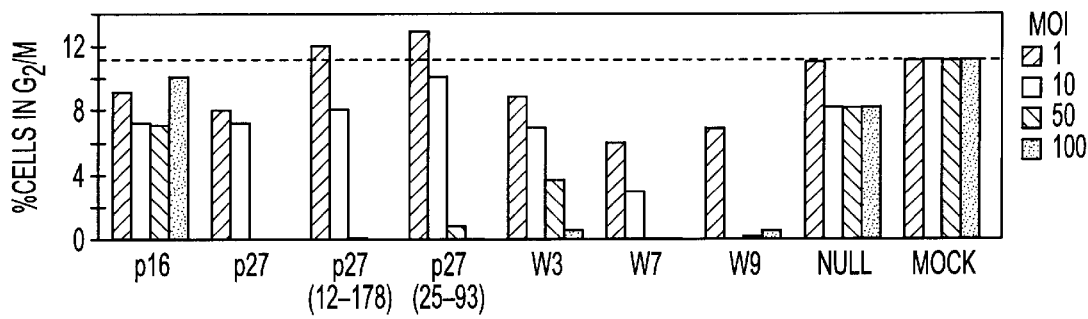
FIG. 1 is a diagrammatic representation showing some recombinant CDK inhibitors of the invention tested in in vitro kinase assays, and the results of these assays. The p16 molecule is indicated by the open box; the p27 molecule and its derivatives are indicated by the hatched boxes; and the 15 amino acids long $(Gly_4Ser)_3$ linker between the p16 and p27 moieties is indicated by the black boxes. Above the schematic for each molecule is the corresponding 5' and 3' amino acid from the parental molecule. The table in the middle shows the $IC^{50}$'s (in nM) of the purified inhibitors as determined by in vitro kinase assays that utilized CDK4/cyclin D1, CDK2/cyclin E, and CDC2/cyclin B kinases. At the right of FIG. 1 is listed the estimated half-life of the adenovirus expressed CDKi protein (in hours) as measured by pulse-chase experiments.
Figures 2, 7B:
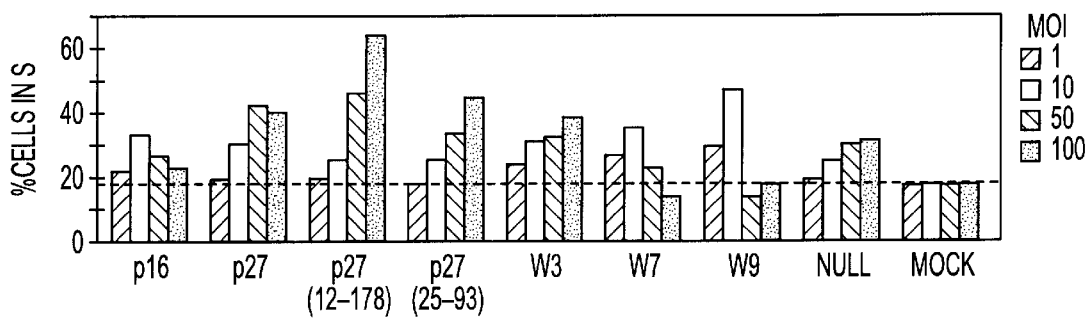
Figure 8A:
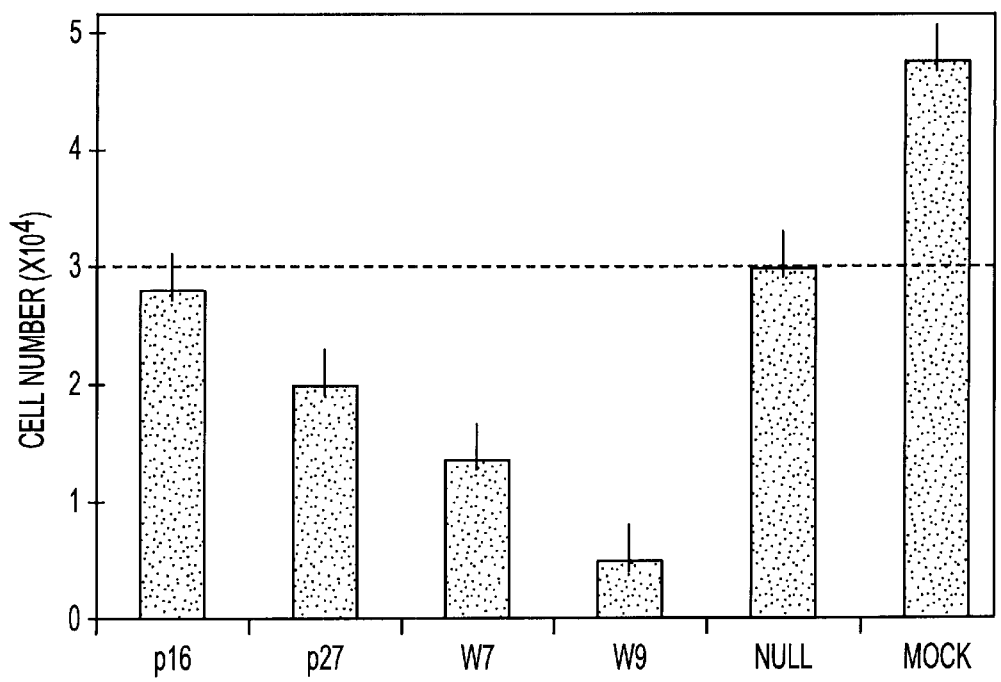
Figure 8B:
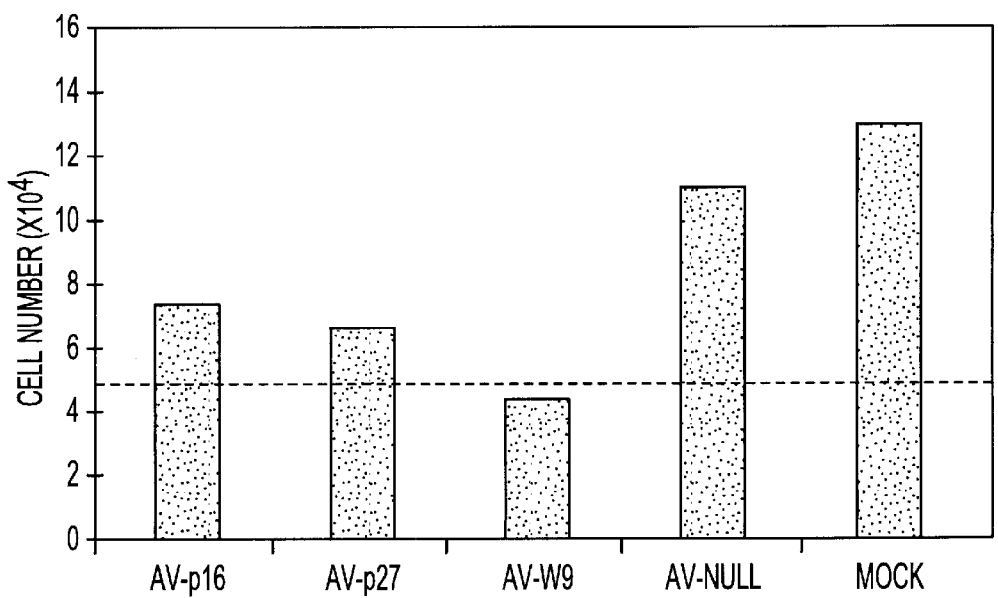
Figures 1, 9A:
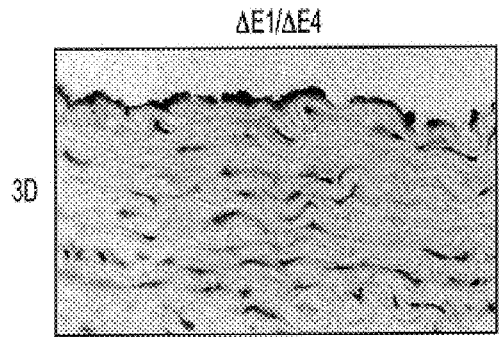
Figures 2, 9A:
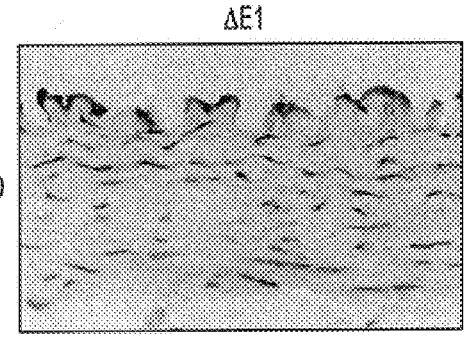
Figures 3, 9A:
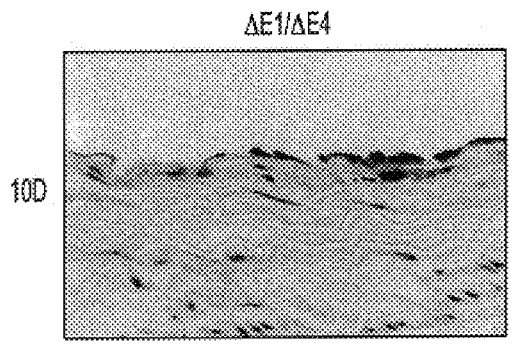
Figures 4, 9A:
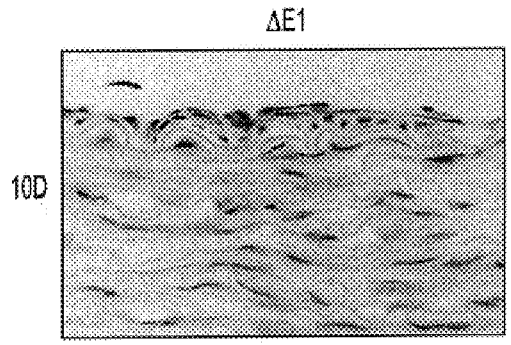
Figures 5, 9A:
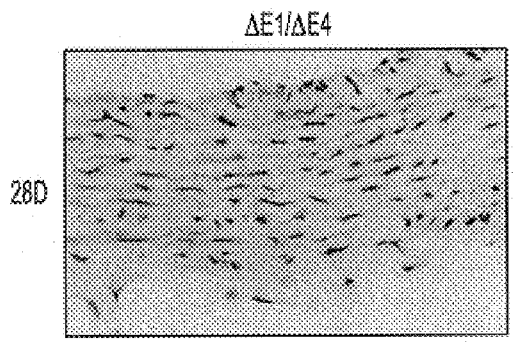
Figures 6, 9A:
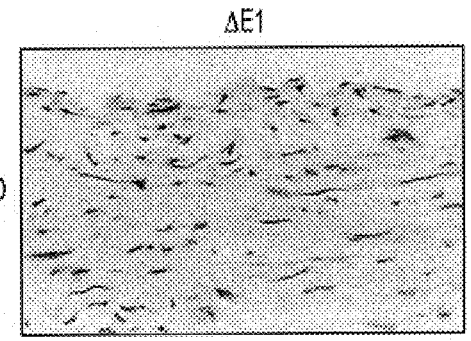
Figure 9B:
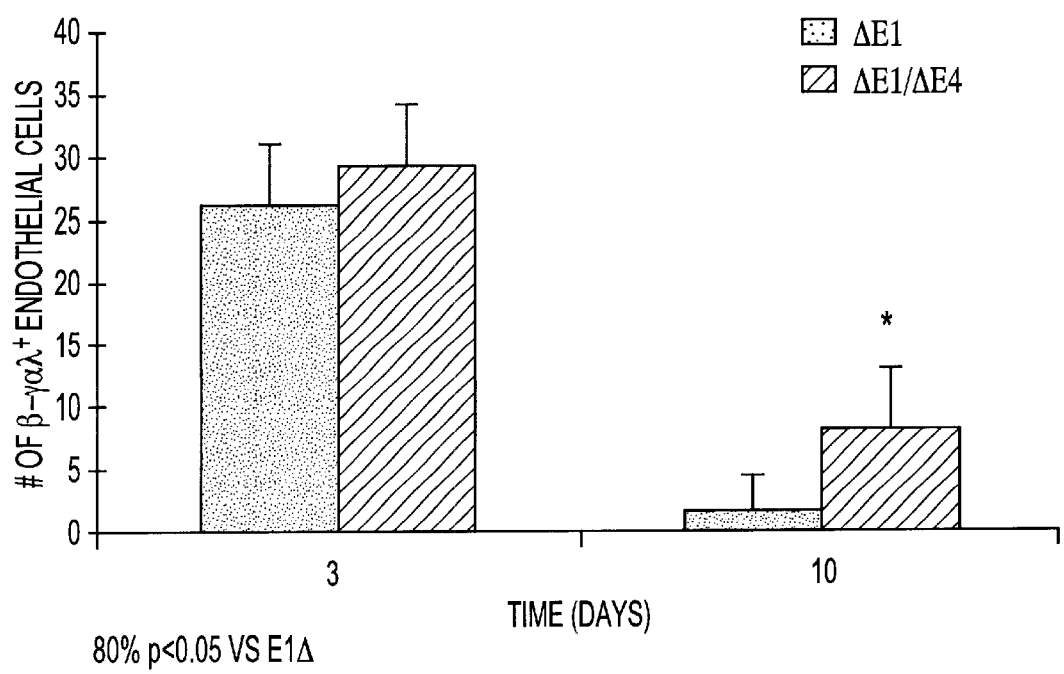
Figures 1, 10A:
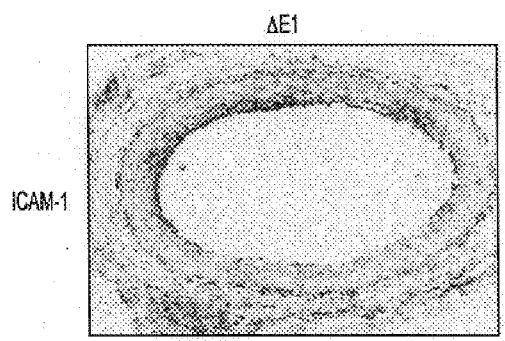
Figures 2, 10A:
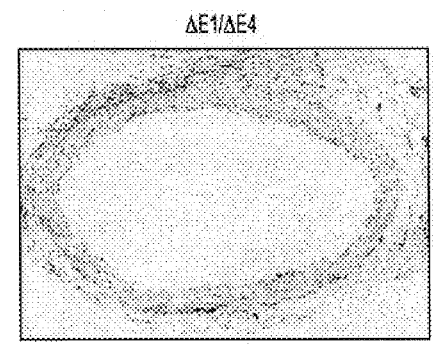
Figures 3, 10A:
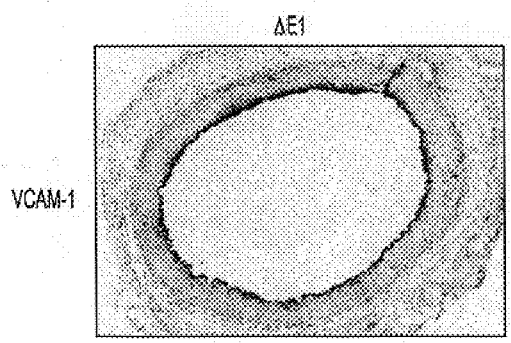
Figures 4, 10A:
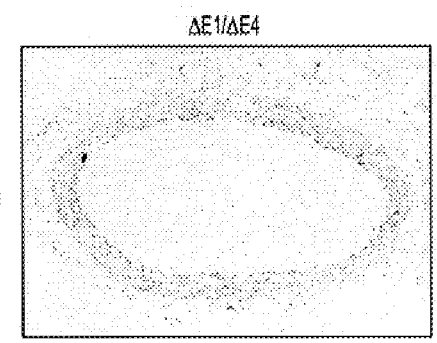
Figures 10B, 10C:
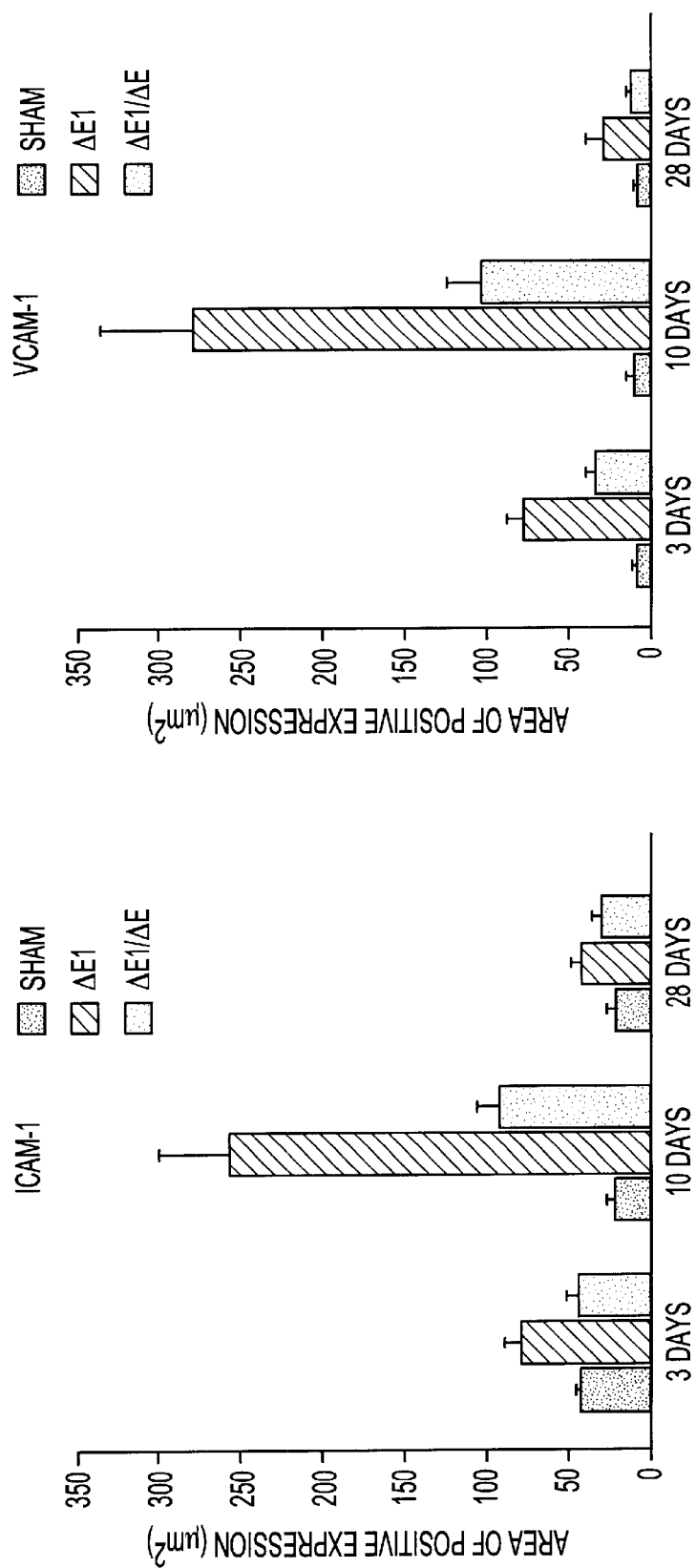
Figures 1, 11A:
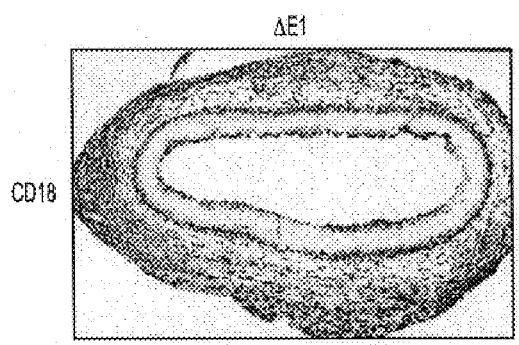
Figures 2, 11A:
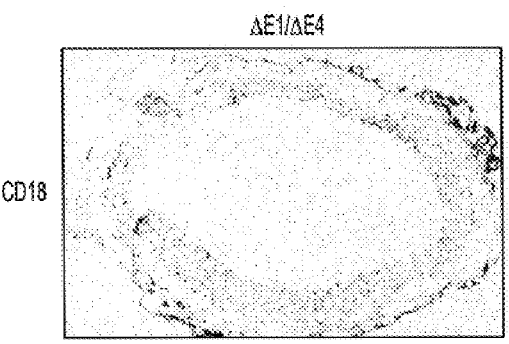
Figures 3, 11A:
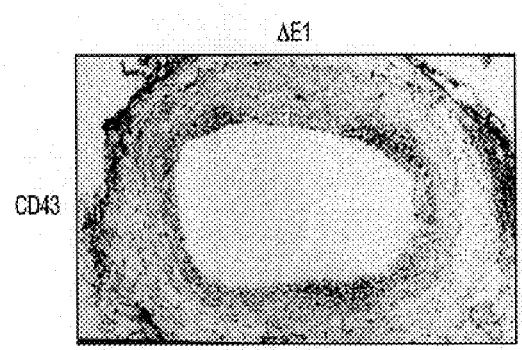
Figures 4, 11A:
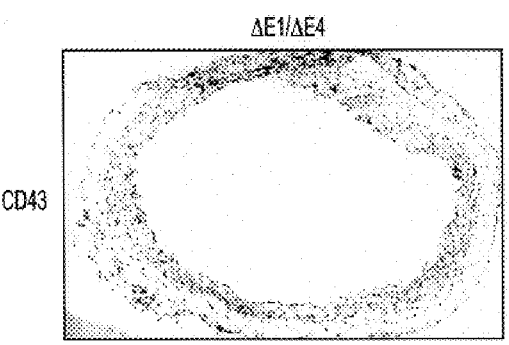
Figure 11B:
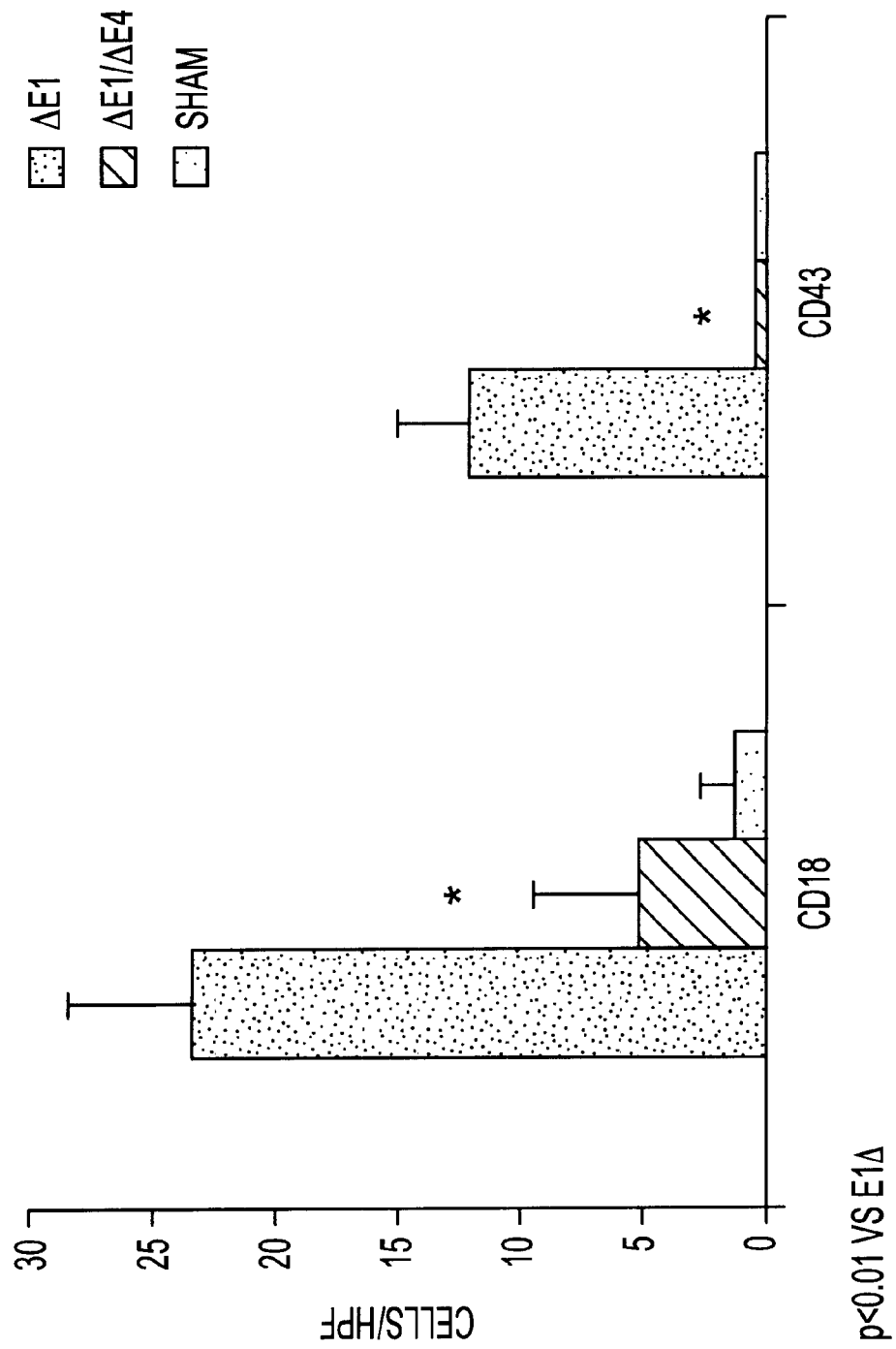
Figure 12B:
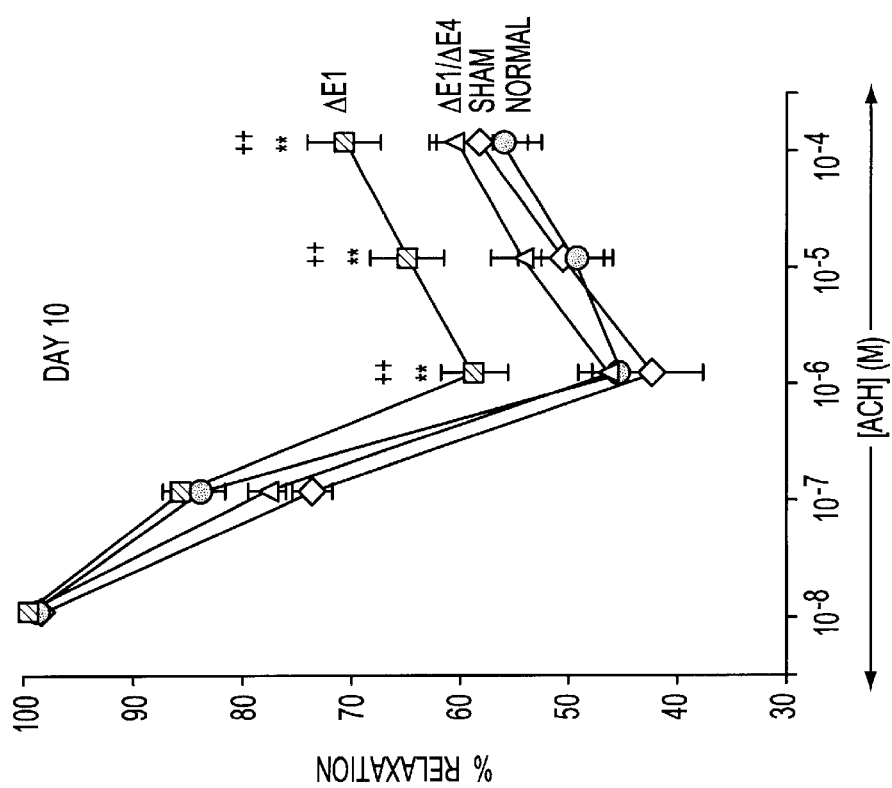
Figure 12A:
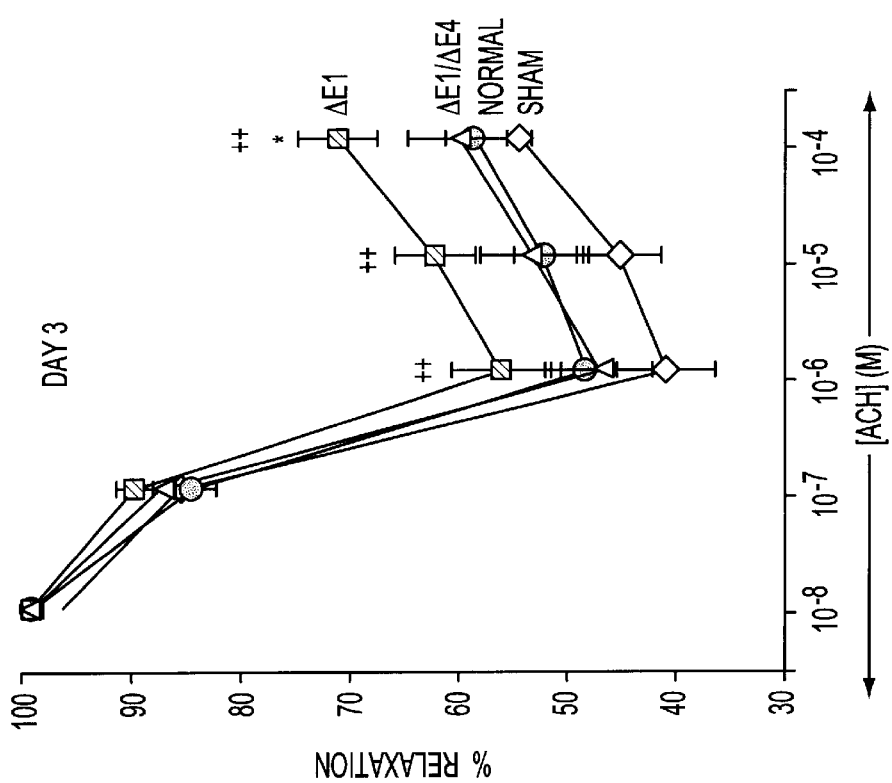
Figures 1, 2, 3, 13A:
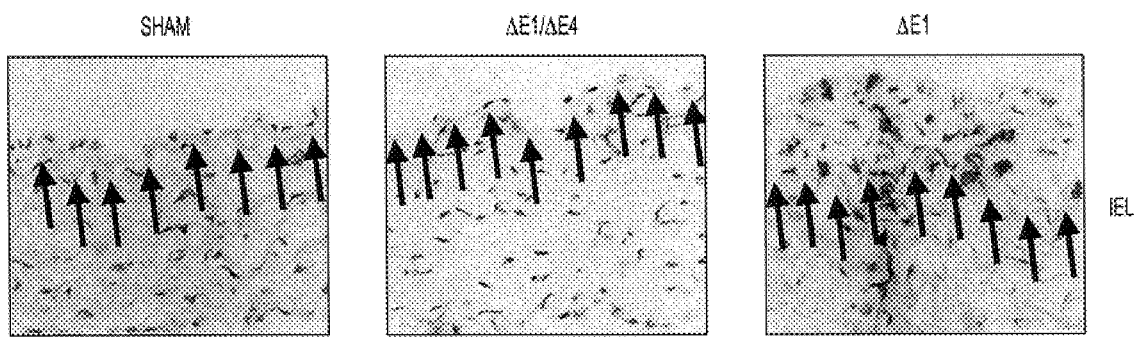
Figures 2, 13C:
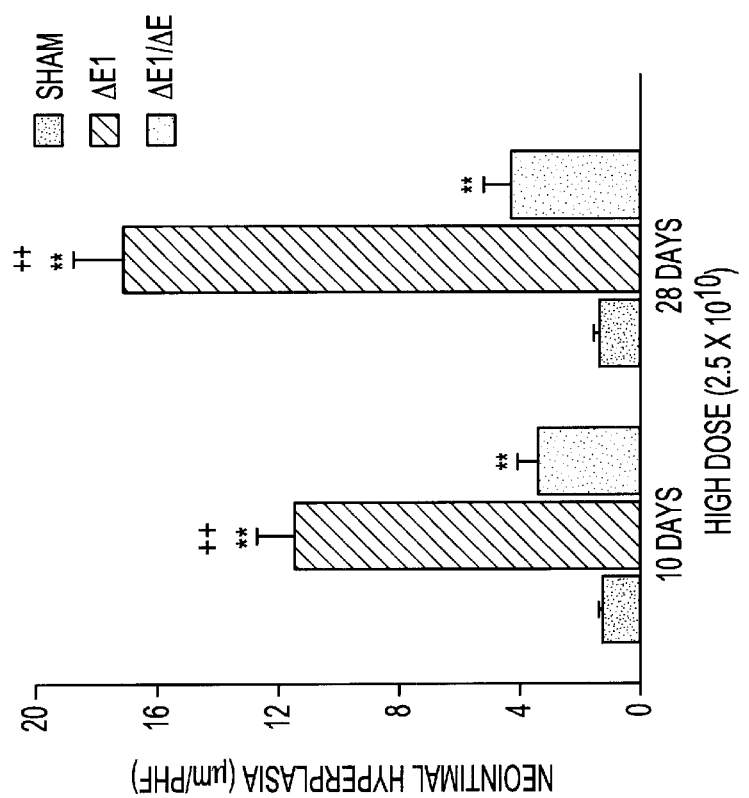
Figures 1, 13C:
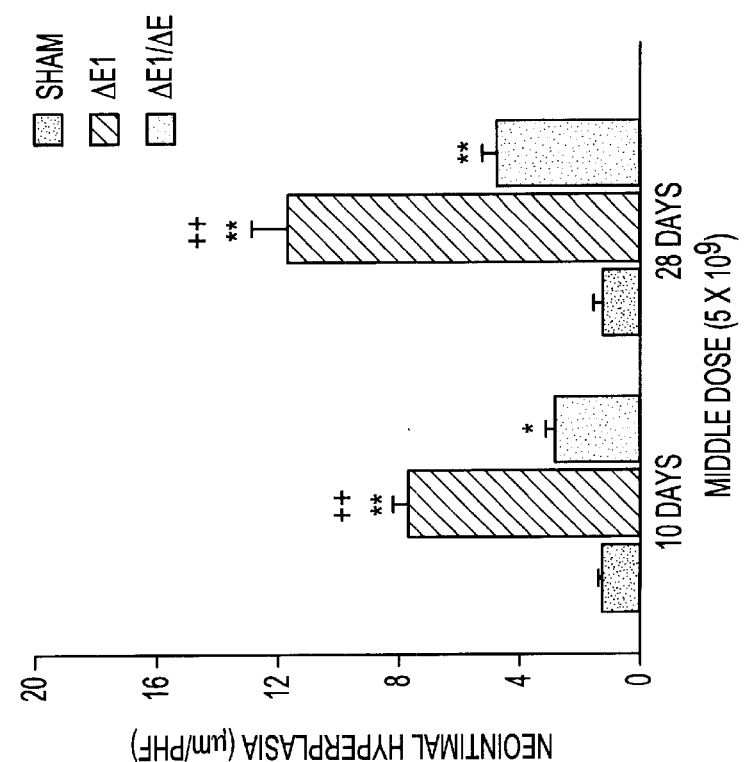
Figure 14A:
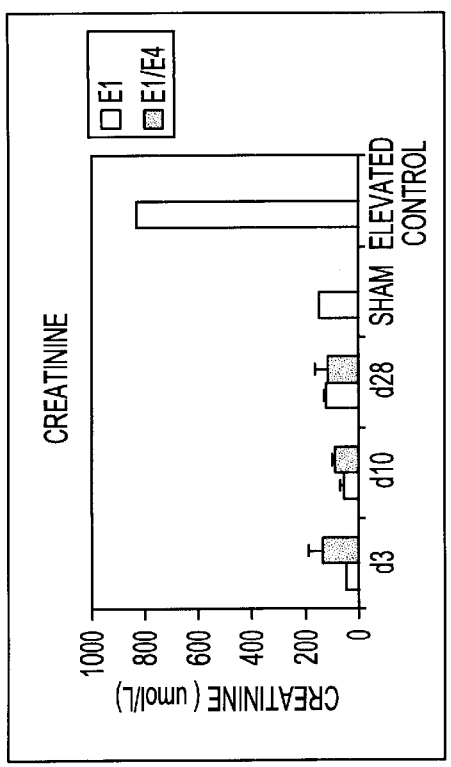
Figure 14B:
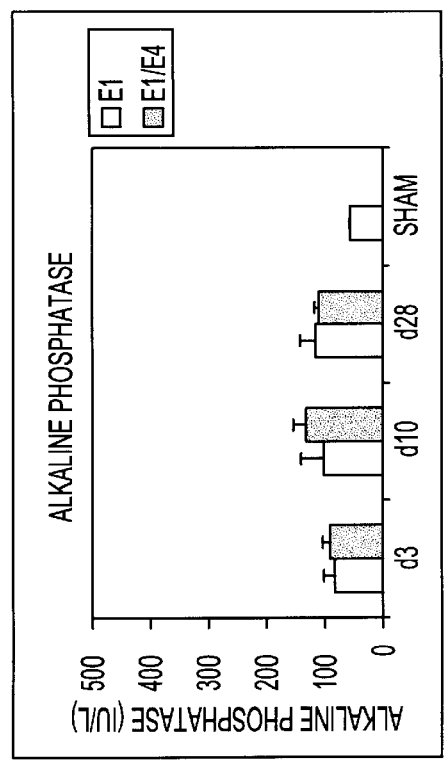
Figure 14C:
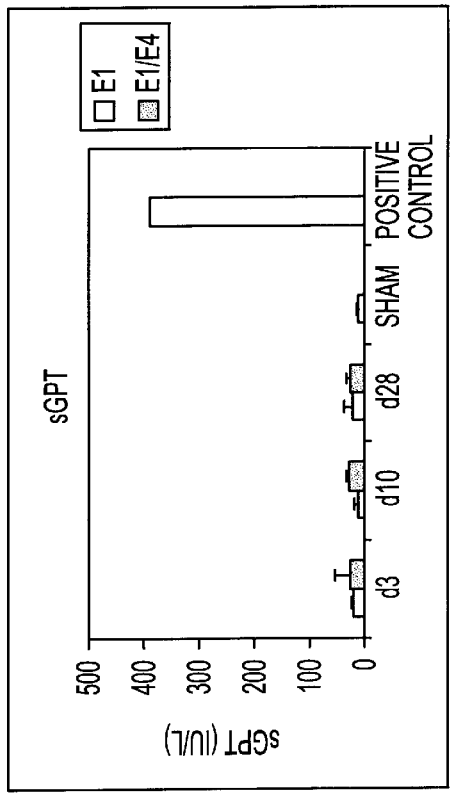
Figure 14D:
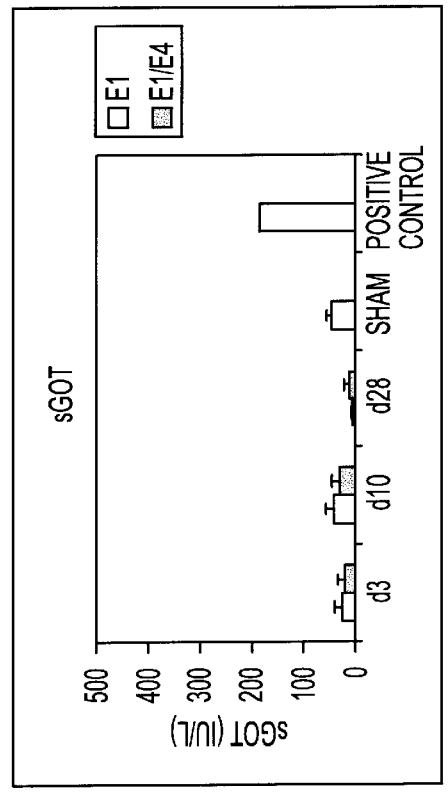

Proliferating cells were transduced with the indicated AV-CDKi at MOI of 50. Forty-eight hours later, the cells were fixed and stained with HA epitope-specific antibody (12CA5, Boehringer) and FITC conjugated rabbit anti-mouse antibody. The left panels show FITC staining of the CDKi proteins in transduced cells; the middle panels show Hoechst staining of the nuclei of these transduced cells, which reveals all of the cells in the field; and the right panels are an overlay of the FITC stained and Hoechst stained images;

FIG. 5A is a graphic representation showing the transduction efficiency of smooth muscle cells with recombinant adenovirus expressing LacZ operably linked to the CMV promoter. Nonproliferating human aortic smooth muscle cells (AoSMC), CASMC, or HeLa cells were either mock treated or transduced with Ad-CMV-Lac-Z at MOI of 10,30 and 100. Five days later, the percentage β-gal positive cells were determined by flow cytometry following staining with FDG substrate (Sigma). Both AoSMC and CASMC showed greater than 95% transduction efficiency at all the MOI tested;

FIG. 5B is a graphic representation showing the transduction efficiency of endothelial cells with recombinant adenovirus expressing LacZ operably linked to the CMV promoter. Nonproliferating human coronary artery endothelial cells (CAECs) or HeLa cells were either mock treated or transduced with AV-CMV-Lac-Z at MOI of 10, 30 and 100. Two days later, the percentage β-gal positive cells were determined by flow cytometry following staining with FDG substrate (Sigma). CAEC showed greater than 90% transduction efficiency at all the MOI tested;

FIG. 6 is a graphic representation showing the inhibition of cell growth of synchronously growing CASMCs by various AV-CDKi. CASMCs were made quiescent by incubation in low serum conditions and transduced with the indicated AV-CDKi's at MOI's of 1 to 250. The next day, cells were stimulated to enter the cell cycle by addition of 10% serum to the media. Cells were harvested 3 days after restimulation with serum-containing media and counted from duplicate wells. The dashed line represents starting cell number;

FIG. 7A is a graphic representation of a series of histograms comparing representative flow cytometric analyses of CASMC's transduced with recombinant adenovirus encoding the various indicated CDKi or Null (i.e., AV-CMV) at 50 MOI. Twenty-four hours after transduction, virus was removed, and the cells were restimulated with 10% FBS-containing media. Three days later, the cells were fixed and stained with propidum iodide, and then subjected to FAC-scan analysis. Cells that were kept in 0.05% FBS for 48 hours (Serum Low) as well as cells that were treated with nothing (Mock Control), n-butyrate (early $G_1$ block), or aphidicolin (early S block) were also analyzed for DNA content as control profiles;

FIG. 7B is a schematic representation of a series of bar graphs comparing the cell cycle distributions (i.e., $G_2$/M phase, S phase, or $G_1$ phase) of the CASMCs transduced with 1,10,50, or 100 MOI of recombinant adenovirus encoding the indicated CDKi or Null (i.e., AV-CMV), or no adenovirus (Mock). The proportion of cells in the different cell cycle stages was determined for mock transduced and adenovirus transduced (1–100 MOI) CASMC. The upper panel shows the percentage of cells in $G_2$/M phase; the middle panel shows the percentage of cells in S phase; and the lower panel shows the percentage of cells in $G_1$ phase;

FIG. 8A is a graphic representation showing the inhibition of cell growth of synchronously growing CAECs by various AV-CDKi. Quiescent CAECs were transduced with AV-CDKi at 10 MOI. The next day, virus was removed, and the cells were stimulated to enter the cell cycle by addition of 10% serum to the media. Cells were harvested 3 days later and counted. The dashed line represents starting cell number at time of infection;

FIG. 8B is a graphic representation showing the inhibition of cell growth of asynchronous CAEC by various AV-CDKi. CAECs were seeded in 6 well dishes and transduced the next day with indicated AV-CDKi at 10 MOI. Virus was removed on the following day, and the cells returned to full serum containing media. Cells were harvested 2 days later and counted. The dashed line represents starting cell number at the time of infection;

FIG. 9A is a representation of a series of photographs comparing the β-gal expression in rabbit carotid arteries 3, 10, or 28 days following treatment with ΔE1-AV-β-gal (right panels) or ΔE1/ΔE4-AV-β-gal (left panels), as determined by immunohistochemistry in which arterial cryosections were stained with lacZ;

FIG. 9B is a graphic representation of quantitation by image analysis of β-gal expression in rabbit carotid arteries following 3 or 10 days of treatment with ΔE1-AV-β-gal (black bars) or ΔE1/ΔE4-AV-β-gal (gray bars);

FIG. 10A is a representation of a series of photographs comparing ICAM-expression in rabbit carotid arteries 10 days following treatment with ΔE1-AV-β-gal (left panels) or ΔE1/ΔE4-AV-β-gal (right panels), as determined by immunohistochemistry in which arterial cryosections were stained with anti-ICAM-1 specific antibodies;

FIG. 10B is a representation of a series of photographs comparing VCAM-1 expression in rabbit carotid arteries 10 days following treatment with ΔE1-AV-β-gal (left panels) or ΔE1/ΔE4-AV-β-gal (right panels), as determined by immunohistochemistry in which arterial cryosections were stained with anti-VCAM-1-specific antibodies;

FIG. 10C is a graphic representation of quantitation by image analysis of ICAM-1 and VCAM-1 expression in rabbit carotid arteries 3,10, or 28 days following treatment with sham (white bars), ΔE1-AV-β-gal (black bars) or ΔE1/ΔE4-AV-β-gal (gray bars). For ICAM-1 (left panel), $5\times10^9$ ffu/ml virus was used for gene transfer. For VCAM-1 (right panel, $2.5\times10^{10}$ focus forming units (ffu)/ml virus was used for gene transfer;

FIG. 11A is a representation of a series of photographs comparing CD18 and CD43 expression in rabbit carotid arteries 10 days following treatment with ΔE1-AV-β-gal (left panels) or ΔE1/ΔE4-AV-β-gal (right panels), as determined by immunohistochemistry in which arterial cryosections were stained with anti-CD18 or anti-CD43 specific antibodies;

FIG. 11B is a graphic representation of quantitation by image analysis of the expression of CD18 (left panel) and CD43 (right panel) in rabbit carotid arteries 10 days following treatment with sham (white bars), ΔE1-AV-β-gal (black bars) or ΔE1/ΔE4-AV-β-gal (gray bars) at $5\times10^9$ ffu/ml virus. Data are presented as mean+/−standard error; * equals $p<0.05$ versus sham control; ** equals $p<0.01$ versus sham control; + equals $p<0.05$ versus ΔE1/ΔE4-AV;++$p<0.01$ versus ΔE1/ΔE4-AV;

FIG. 12 is a graphic representation showing the endothelium-dependent vascular relaxation of arteries pre-contracted to 90% of maximal tension with phenylephrine, and then perfused with the indicated concentrations of acetylcholine ([Ach] (M)). Vasomotor function was evaluated 3 (left panel), 10 (middle panel), and 28 (right panel)

days following gene transfer for both middle titer and high titer-treated arteries. Data for the middle titer (8) are presented as mean+/−standard error; * equals p<0.05 versus sham control; ** equals p<0.01 versus sham control;+equals p<0.05 versus ΔE1/ΔE4-AV;++p<0.01 versus ΔE1/ΔE4-AV;

FIG. 13A is a representation of a series of photographs comparing neointimal hyperplasia 10 days following treatment of the vessels with sham (left panel), 5×10$^9$ ffu/ml ΔE1/ΔE4-AV (middle panel), and 5×10$^9$ ffu/ml ΔE1-AV (right panel). Arterial cryosections are stained with Voerhoff's stain. Arrows indicate the internal elastic lamina (IEL);

FIG. 13B is a representation of a series of photographs comparing neointimal hyperplasia 28 days following treatment of the vessels with ΔE1-AV-β-gal (black bars) or ΔE1/ΔE4-AV-β-gal (gray bars) at 5×10$^9$ ffu/ml virus (left panel) or 2.5×10$^{10}$ ffu/ml virus (right panel). Data are presented as mean+/−standard error; * equals p<0.05 versus sham control; ** equals p<0.01 versus sham control;+ equals p<0.05 versus ΔE1/ΔE4-AV;++p<0.01 versus ΔE1/ΔE4-AV. Arterial cryosections are stained with Voerhoff's stain. Arrows indicate the internal elastic lamina (IEL);

FIG. 13C is a graphic representation of quantitation by image analysis of the neointimal hyperplasia of rabbit carotid arteries 10 or 28 days following treatment with 5×10$^9$ ffu/ml(left panel), or 2.5×10$^{10}$ ffu/ml (right panel) of either ΔE1-AV-β-gal (black bars) or ΔE1/ΔE4-AV-β-gal (gray bars), with sham treatment shown as white bars. Neotintimal hyperplasia in sham-treated carotid arteries is denoted by white bars. Data are presented as mean+/− standard error; * equals p<0.05 versus sham control; * equals p<0.01 versus sham control;+equals p<0.05 versus ΔE1/ΔE4-AV;++p<0.01 versus ΔE1/ΔE4-A;

FIGS. 14A–14D is a graphic representation of four panels showing the levels of glutamic pyruvic transaminase (sGPT; FIG. 14A) and glutamic oxalacetic transaminase (sGOT; FIG. 14B), creatinine (FIG. 14C), and alkaline phosphatase (FIG. 14D) in the serum of rabbits that were either sham-infected or transduced with either the ΔE1-AV (which contains the E3 region) or ΔE1/ΔE4-AV at 3, 10, or 28 days after transduction.

Figures 1, 2, 3, 15A:
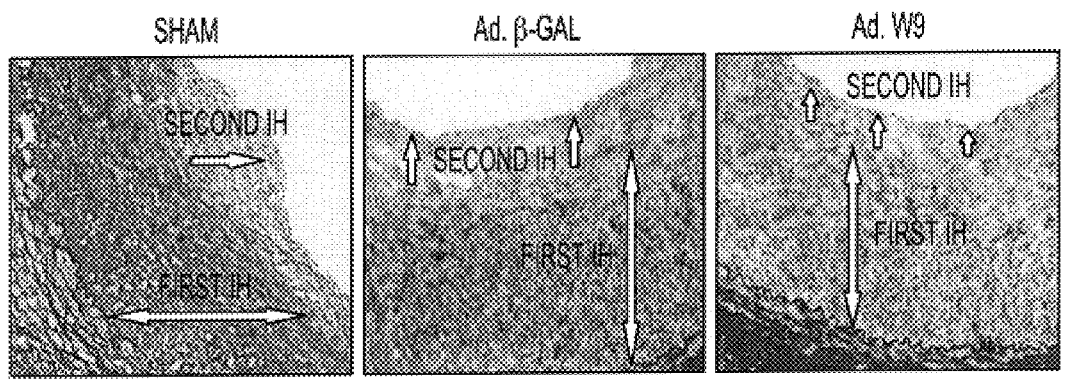
Figures 1, 2, 3, 16A:
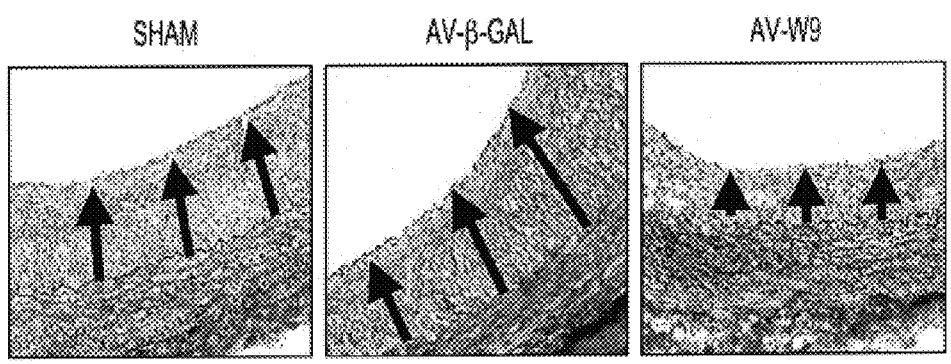
Figure 15B:
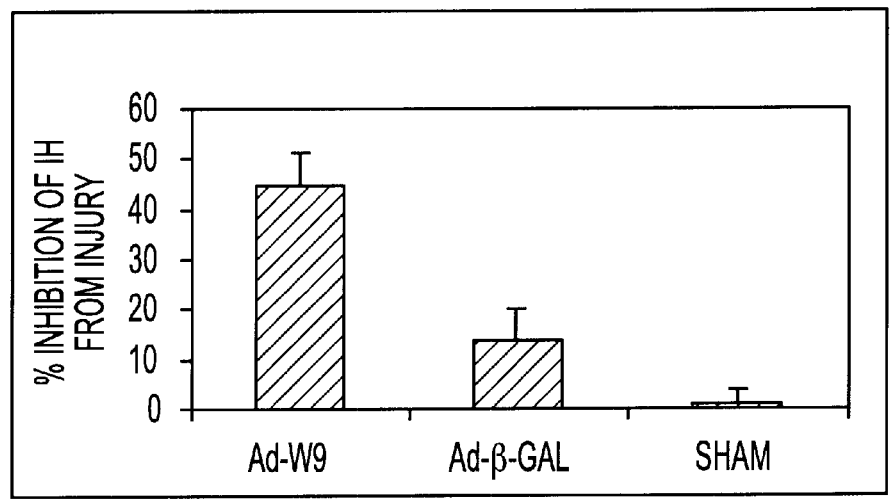
Figure 16B:
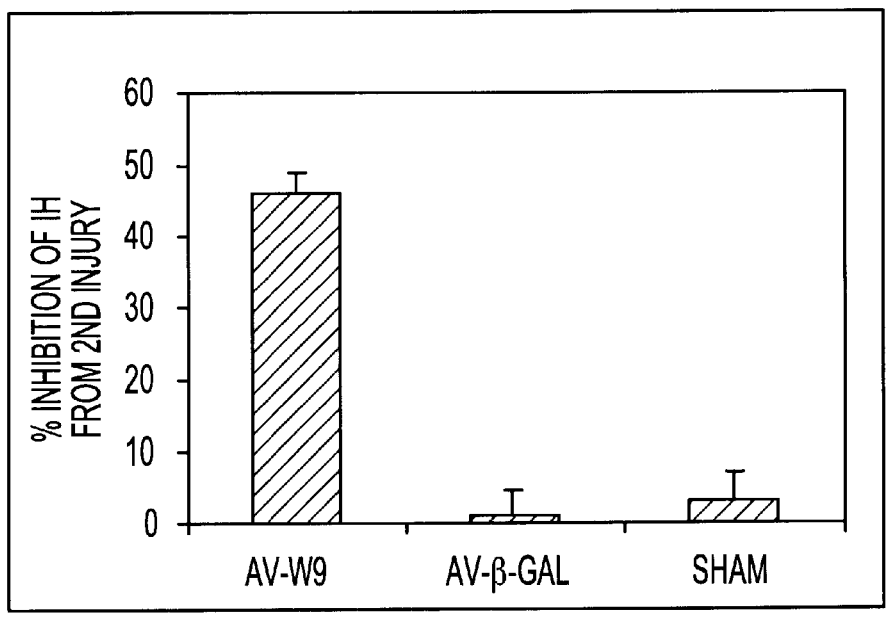
Figures 1, 2, 3, 17A:
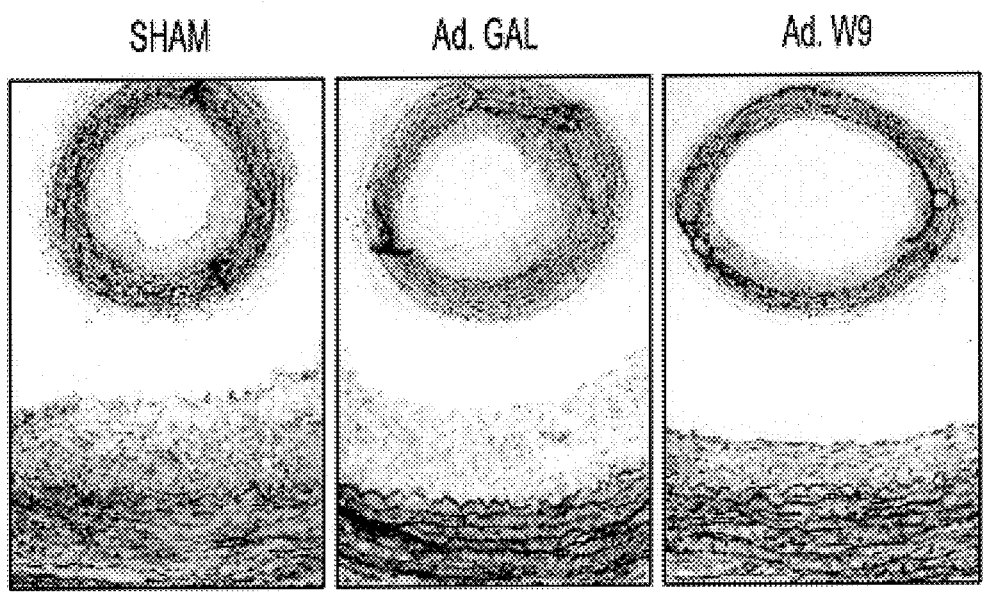
Figure 17B:
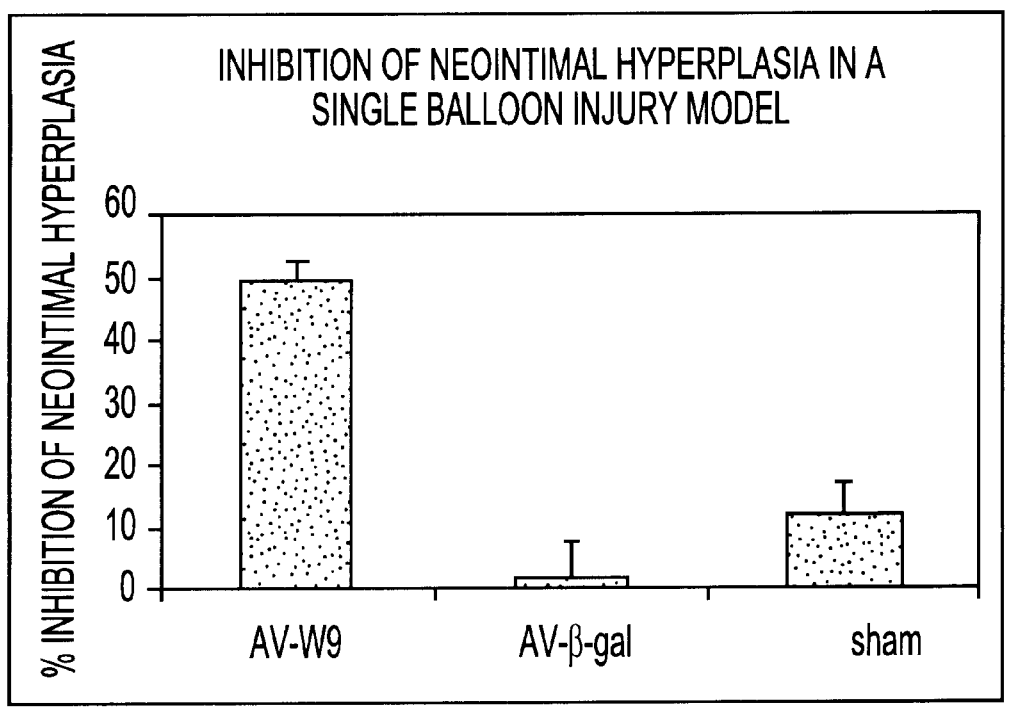
Figures 1, 18A:
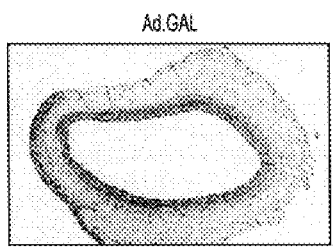
Figures 2, 18A:
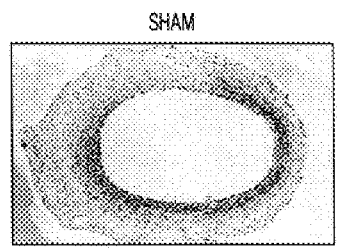
Figures 3, 18A:
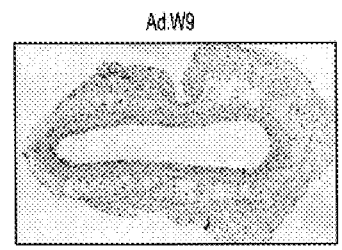
Figures 4, 18A:
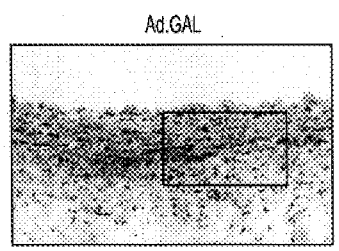
Figures 5, 18A:
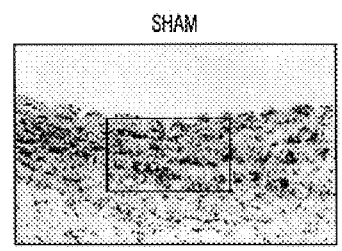
Figures 6, 18A:
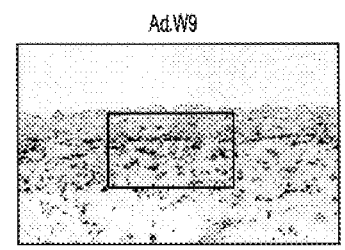
Figure 18B:
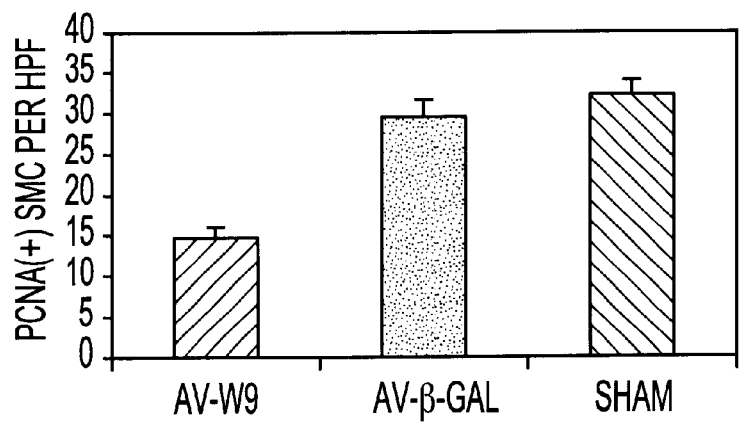
Figure 19:
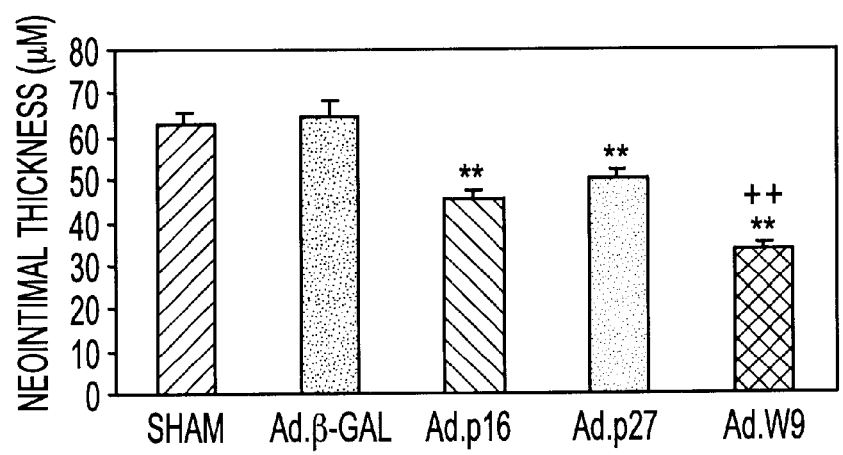
Figures 1, 20A:
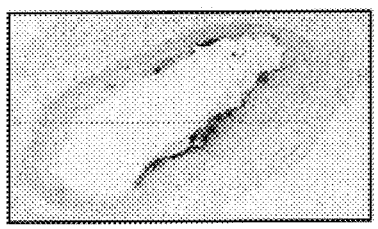
Figures 2, 20A:
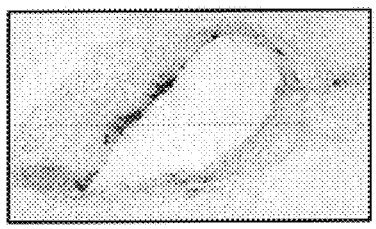
Figures 3, 20A:
Figures 4, 20A:
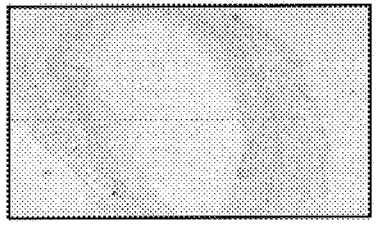
Figures 5, 20A:
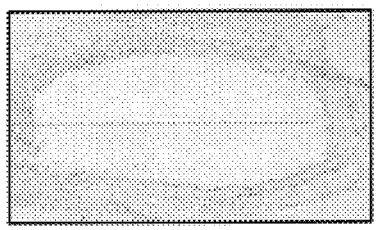
Figure 20B:
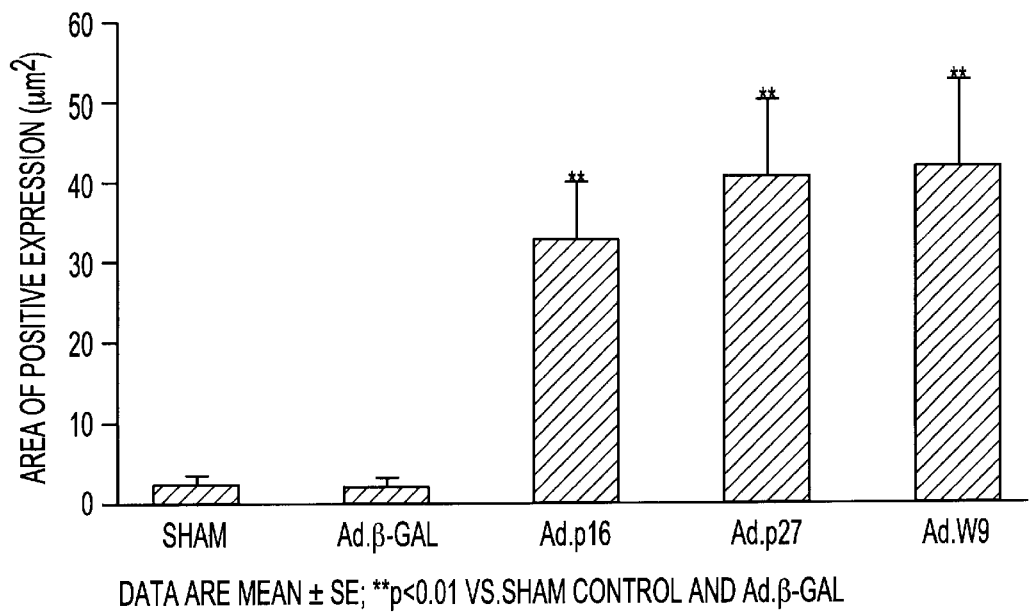
Figure 21:
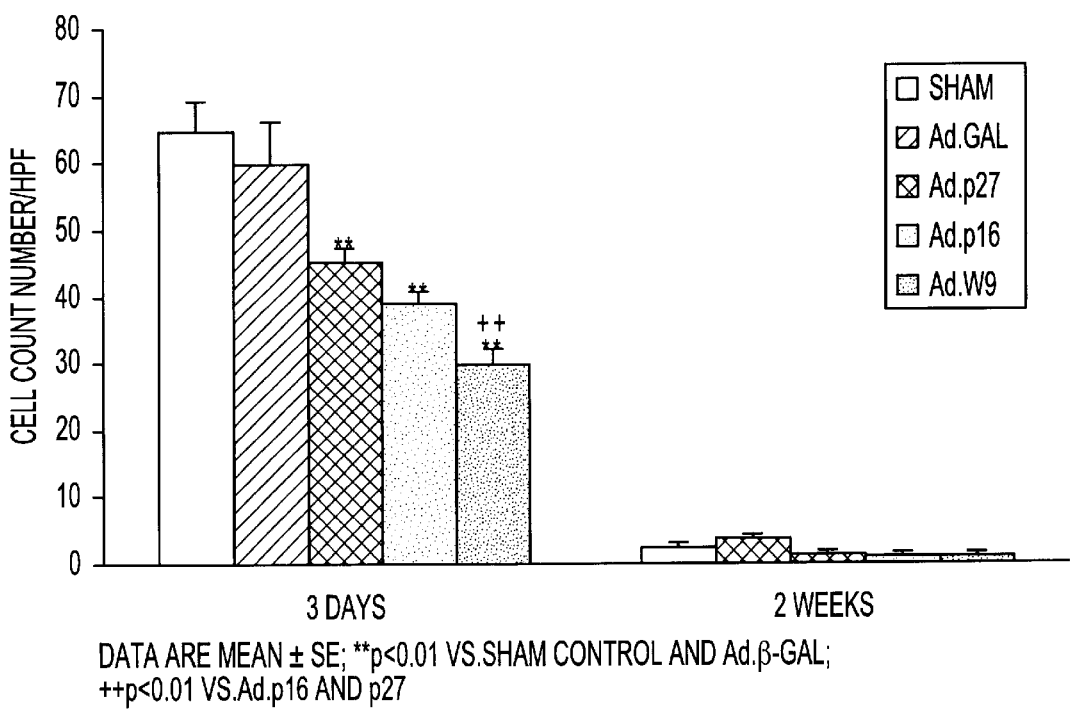
Figure 22B:
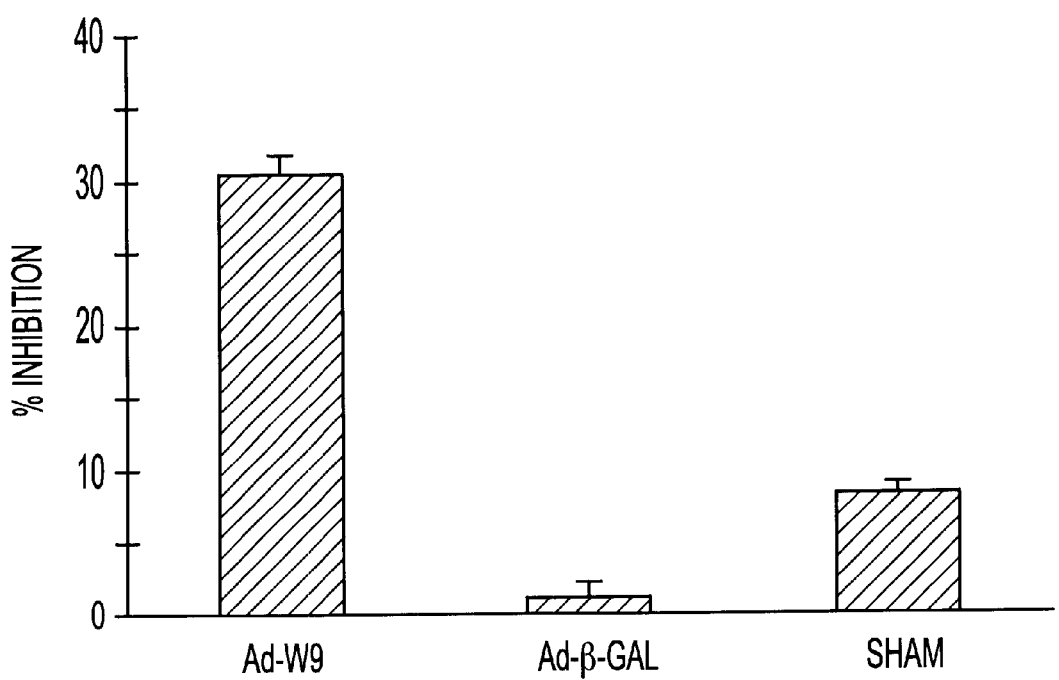
Figure 23A:
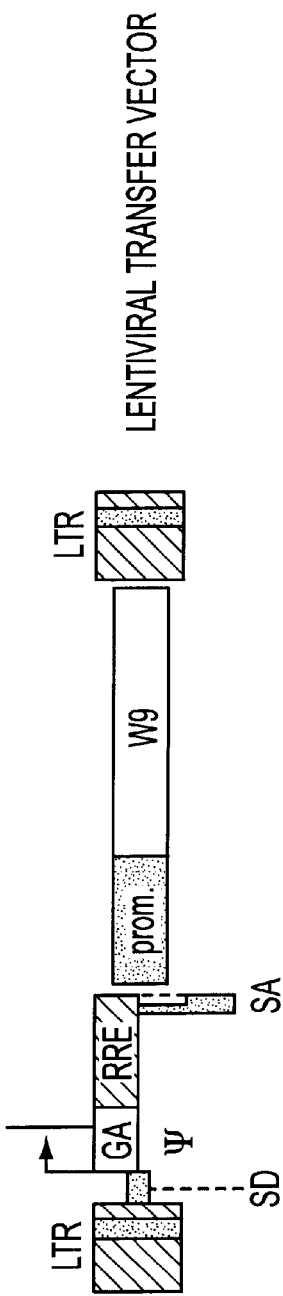
Figure 23B:
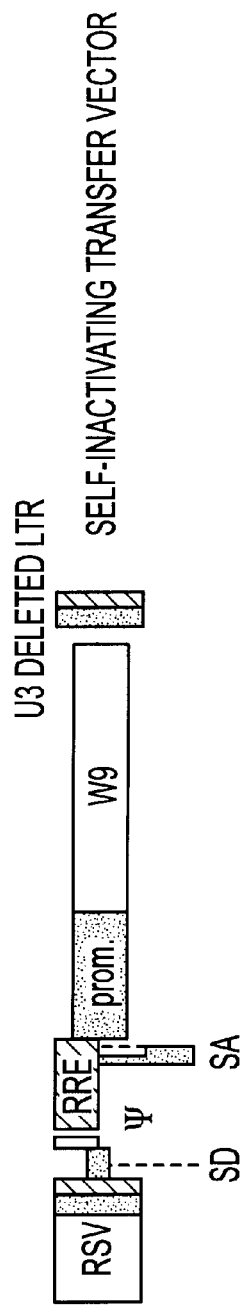

FIG. 15A is a representation of three photographs comparing the neointimal hyperplasia observed in rabbit carotid artery segments in the Double Balloon Injury Model, where the gene transfer occurred two weeks following the first injury and where gene transfer was a sham infection (left panel), transduction with a recombinant adenovirus expressing β-galactosidase (middle panel), or transduction with ΔE1/ΔE3-AV-W9, a ΔE1/ΔE3 adenovirus expressing a non-limiting, representative CDKi of the invention, W9 (right panel);

FIG. 15B is a graphic representation of the percent inhibition of neointimal hyperplasia of rabbit carotid artery segments in the Double Balloon Injury Model, where the gene transfer occurred two weeks following the first injury and was a sham infection, transduction with a recombinant adenovirus expressing β-galactosidase, or transduction with ΔE1/ΔE3-AV-W9, a ΔE1/ΔE3 adenovirus expressing a non-limiting, representative CDKi of the invention, W9;

FIG. 16A is a representation of three photographs comparing the neointimal hyperplasia observed in rabbit carotid artery segments in the Double Balloon Injury Model, where the gene transfer occurred one week following the first injury and where gene transfer was a sham infection (left panel), transduction with a recombinant adenovirus expressing β-galactosidase (middle panel), or transduction with ΔE1/ΔE3-AV-W9, a ΔE1/ΔE3 adenovirus expressing a non-limiting, representative CDKi of the invention, W9 (right panel);

FIG. 16B is a graphic representation of the percent inhibition of neointimal hyperplasia of rabbit carotid artery segments in the Double Balloon Injury Model, where the gene transfer occurred one week following the first injury and was a sham infection, transduction with a recombinant adenovirus expressing β-galactosidase, or transduction with ΔE1/ΔE3-AV-W9, a ΔE1/ΔE3 adenovirus expressing a non-limiting, representative CDKi of the invention, W9;

FIG. 17A is a representation of three photographs comparing the neointimal hyperplasia observed in rabbit carotid artery segments in the Single Balloon Injury Model, where the gene transfer occurred three days following the injury and where gene transfer was a sham infection (left panel), transduction with a recombinant adenovirus expressing β-galactosidase (middle panel), or transduction with ΔE1/ΔE3-AV-W9, a ΔE1/ΔE3 adenovirus expressing a non-limiting, representative CDKi of the invention, W9 (right panel);

FIG. 17B is a graphic representation of the percent inhibition of neointimal hyperplasia of rabbit carotid artery segments in the Single Balloon Injury Model, where the gene transfer occurred three days following the injury and was a sham infection, transduction with a recombinant adenovirus expressing β-galactosidase, or transduction with ΔE1/ΔE3-AV-W9, a ΔE1/ΔE3 adenovirus expressing a non-limiting, representative CDKi of the invention, W9;

FIG. 18A is a representation of nine photographs (A through I) comparing the PCNA expression observed in rabbit carotid artery segments in the Single Balloon Injury Model, where the gene transfer occurred three days following the injury and where gene transfer was a sham infection (middle panels), transduction with a recombinant adenovirus expressing β-galactosidase (left panels), or transduction with ΔE1/ΔE3-AV-W9, a ΔEl /ΔE3 adenovirus expressing a non-limiting, representative CDKi of the invention, W9 (right panels). The black arrows show smooth muscle cells in the state of mitosis, yellow arrows show smooth muscle cells in the state of proliferation (i.e., positive for PCNA), and green arrows show smooth muscle cells which have changed from normal contractive to an abnormal secretory state;

FIG. 18B is a graphic representation of the PCNA expression in rabbit carotid artery segments in the Single Balloon Injury Model, where the gene transfer occurred three days following the injury and was a sham infection, transduction with a recombinant adenovirus expressing β-galactosidase, or transduction with ΔE1/ΔE3-AV-W9, a ΔE1/ ΔE3 adenovirus expressing a non-limiting, representative CDKi of the invention, W9;

FIG. 19 is a graphic representation of the percent inhibition of neointimal hyperplasia of rabbit carotid artery segments in the Single Balloon Injury Model, where the gene transfer occurred three days following the injury and was a sham infection, transduction with a recombinant adenovirus expressing β-galactosidase, or transduction with ΔE1/ΔE3-AV-p16, ΔE1/ΔE3-AV-p27, or ΔE1/ΔE3-AV-W9, three ΔE1/ ΔE3 adenoviruses expressing non-limiting, representative CDKi's of the invention;

FIG. 20A is a representation of five photographs comparing the transgene expression observed in rabbit carotid artery segments in the Single Balloon Injury Model, where the gene transfer occurred three days following the injury and where gene transfer was a sham infection (bottom panel), transduction with a recombinant adenovirus expressing β-galactosidase (fourth panel from the top), or transduction with ΔE1/ΔE3-AV-p27 (third panel from top), ΔE1/ΔE3-AV-p16 (second panel from top), or ΔE1/ΔE3-AV-W9 (top panel), three ΔE1/ΔE3 adenoviruses expressing non-limiting, representative CDKi's of the invention. The segments were stained with anti-HA antibody;

FIG. 20B is a graphic representation of transgene expression in rabbit carotid artery segments in the Single Balloon Injury Model, where the gene transfer occurred three days following the injury and was a sham infection, transduction with a recombinant adenovirus expressing β-galactosidase, or transduction with ΔE1/ΔE3-AV-p27, ΔE1/ΔE3-AV-p16, or ΔE1/ΔE3-AV-W9, three ΔE1/ΔE3 adenoviruses expressing non-limiting, representative CDKi's of the invention. Data shown are Mean +/−SE; ** p<0.001 vs. sham control and ΔE1/ΔE3-AV-β-gal;++p<0.01 vs. ΔE1/ΔE3-p16 and ΔE1/ΔE3-AV-p27;

FIG. 21 is a graphic representation showing the reduction in PCNA expression following transduction with ΔE1/ΔE3 AV-CDKi of the invention. Segments of rabbit carotid artery were stained for PCNA expression, which was quantitated, 3 days or 14 days following gene transfer in the Single Balloon Injury Model. Animals were treated with sham infection (white bars), ΔE1/ΔE3-AV-β-gal (hatched bars), ΔE1/ΔE3-AV-p27 (cross-hatched bars), ΔE1/ΔE3-AV-p16 (gray bars), or ΔE1/ΔE3-AV-29 (black bars). Data shown are Mean+/−SE; ** p<0.01 vs. sham control and ΔE1/ΔE3-AV-β-gal;++p<0.05 vs. ΔE1/ΔE3-AV-p16 and AV-p27;

FIG. 22A is a representation of two photographs comparing the adventitial hyperplasia of rabbit vein graft segments in the Rabbit Vein Graft Model ten days following a gene transfer which was sham infection (left panel) or transduction with ΔE1/ΔE3-AV-W9, a ΔE1/ΔE3 adenovirus expressing a non-limiting, representative CDKi of the invention, W9;

FIG. 22B is a graphic representation of the percent inhibition of adventitial hyperplasia of rabbit vein graft segments in the Rabbit Vein Graft Model, where the gene transfer was sham infection (left panel) or transduction with ΔE1/ΔE3-AV-W9, a ΔE1/ΔE3 adenovirus expressing a non-limiting, representative CDKi of the invention, W9;

FIG. 23A is a schematic representation of a recombinant lentivirus vector, according to the invention, which contains a nucleic acid sequence encoding a secretable, internalizable form of a non-limiting representative CDKi of the invention, W9, operably linked to regulatory sequences and flanked by HIV LTRs; and FIG. 23B is a schematic representation of a recombinant, self-inactivating lentiviral vector according to the invention, which contains a nucleic acid sequence encoding a secretable, internalizable form of a non-limiting representative CDKi of the invention, W9, operably linked to regulatory sequences.

DETAILED DESCRIPTION OF THE PREFERRED EMBODIMENTS

The patent and scientific literature referred to herein establishes knowledge that is available to those with skill in the art. The issued patents, applications, and references, including GenBank database sequences, that are cited herein are hereby incorporated by reference to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The invention provides methods and reagents for inhibiting smooth muscle cell hyperproliferation. These methods and reagents allow the reduction or alleviation of symptoms resulting from a condition associated with smooth muscle cell hyperproliferation, such as restenosis following balloon angioplasty. In addition, therapeutic compositions for treating and/or alleviating the symptoms of a condition associated with smooth muscle cell hyperproliferation may be developed using the methods and reagents of the invention. Moreover, the process of smooth muscle cell proliferation can be better understood and studied using the methods and reagents of the invention. For example, the methods and reagents of the invention are useful for identifying particular characteristics of proliferating smooth muscle cells. In addition, the methods and reagents of the invention can be used to synchronize the growth of smooth muscle cells cultured in vitro.

Thus, the reagents according to the invention are useful as analytical tools and as therapeutic tools, including gene therapy tools. The invention also provides methods and compositions which may be manipulated and fine-tuned to fit the condition(s) to be treated while producing fewer side effects.

Accordingly, in a first aspect, the invention provides a method for inhibiting smooth muscle cell hyperproliferation comprising transducing smooth muscle cells with an effective amount of a recombinant adenovirus that lacks a functional E4 region, lacks a functional E1 region, and that comprises a transgene encoding a cyclin dependent kinase inhibitor (CDKi), wherein hyperproliferation of the transduced smooth muscle cell is inhibited.

Cyclin dependent kinase inhibitors (CDKi) are proteins which regulate the activity of cyclin-dependent kinase (CDK)/cyclin complexes which play a key role in the cell cycle. CDK/cyclin complexes are the association of a catalytic kinase subunit (such as cdc2, CDK2, CDK4, or CDK6) with one of a variety of regulatory cyclin subunits (such as cyclins A, B1, B2, D1, D2, D3, or E) which results in the assembly of functionally distinct CDK/cyclin complexes.

Thus, in accordance with the invention, by "cyclin dependent kinase inhibitor (CDKi)" is meant any protein which inhibits and/or regulates a CDK/cyclin complex. The definition includes, without limitation, proteins from the CIP/KIP family of CDKi proteins which includes, without limitation, human $p27^{kip1}$ (GenBank Accession No. 10906, Polyak et al. (1994) Cell 78: 56–66); murine $p27^{kip1}$ (GenBank Accession No. 09968, Polyak et al. (1994) Cell 78: 56–66); rat $p27^{kip1}$ (GenBank Accession Nos. D86924 and D83792, Nomura et al. (1997) Gene 191(2): 211–218); human $p57^{KIP2}$ (GenBank Accession No. NM_000076, Matsuoka et al. (1995) Genes Dev. 9(6): 650–662); murine $p57^{KIP2}$ (GenBank Accession No. U20553, Lee et al. (1995) Genes Dev. 9(6): 639–649); canine $p21^{Waf1/CiP1}$ (GenBank Accession No. AF076469); and human $21^{Waf1/Cip1}$ (GenBank Accession No. L25610; Harper et al. (1993) Cell 75: 806–816, 1993); as well as proteins from the INK4 family of CDKi proteins which includes, without limitation, human $p18^{CDKN2C}$ (GenBank Accession Nos. AF041248 and NM_001262, Blais et al. (1998) Biochem. Biophys. Res. Commun. 247(1): 146–153); human Cdi1 (GenBank Accession No. NM_005192, Gyuris et al. (1993) Cell 75(4): 791–803); human $p19^{INK4d}$ (GenBank Accession No.

NM_001800, Guan et al. (1996) *Mol. Biol. Cell* 7(1): 57–70); human p15 (GenBank Accession No. S75756, Jen et al. (1994) *Cancer Res.* 54(24): 6353–6358); murine p15$^{INK4b}$ (GenBank Accession Nos. U80415, U79634, and U79639); murine p16$^{Ink4/MTS1}$ (GenBank Accession Nos. AF044336 and AF044335, Zhang et al. (1998) *Proc. Natl. Acad. Sci.* (*USA*) 95(5): 2429–2434); and human p16$^{INK4}$ (GenBank Accession No. NM_000077; Serrano et al. (1993) *Nature* 366(6456): 704–707 and Okamoto et al. (1994) *Proc. Natl. Acad. Sci.* (*USA*) 91(23): 11045–11049). Exemplary CDKi of the invention are the fusion proteins described herein and described in PCT Publication No. WO99/06540 (hereby incorporated by reference).

By "proliferation of smooth muscle cells" is meant an increase in cell number or an increase in rate of cell division. By "hyperproliferation of smooth muscle cells" is meant proliferation of smooth muscle cells in a blood vessel that results in a a vascular pathology. One non-limiting example of smooth muscle cell hyperproliferation is restenosis, which is the hyperproliferation of vascular smooth muscle cells following trauma or injury to the vessels due to, e.g., angioplasty. Preferred smooth muscle cells of the invention are vascular smooth muscle cells including, without limitation, arterial and venous smooth muscle cells.

By "an effective amount" of the agent is meant the maximal tolerable dose or a dose sufficient to prevent clinical restenosis. By "clinical restenosis" is meant at least 50% occlusion of the vessel lumen resulting from smooth muscle cell proliferation.

By "inhibiting" smooth muscle cell proliferation is meant a reduction in the amount of proliferation of smooth muscle cells. The reduction in growth of vascular smooth muscle cells can be determined experimentally using cultured smooth muscle cells in vitro, where the inhibition in smooth muscle cell proliferation following exposure to the CDKi agent is ascertained by counting the number of smooth muscle cells using a microscope or FACS based assay. The reduction in growth in this scenario would be minimally 25% and preferably greater than 80% comparing treated and untreated smooth muscle cell cultures. Alternatively, reduction in growth of vascular smooth muscle cells can be determined experimentally using animal models of arterial balloon injury, where the inhibition in smooth muscle cell proliferation following exposure to the CDKi agent is ascertained by histological assessment of treated and untreated vessels for neointimal hyperplasia or staining the vessel for markers of cell proliferation, such as PCNA. The reduction in growth in this scenario would be minimally 10% and preferably greater than 40% comparing treated and untreated vessels. Alternatively, reduction in growth of vascular smooth muscle cells can be determined experimentally using animal models of vein graft failure, where the inhibition in smooth muscle cell hyperproliferation following exposure to the CDKi agent is ascertained by histological assessment of treated and untreated vessels for neointimal hyperplasia, adventitial hyperplasia or staining the vessel for markers of cell proliferation, such as PCNA. The reduction in growth in this scenario would be minimally 10% and preferably greater than 40% comparing treated and untreated vessels.

In one embodiment where a transgene encoding a CDKi of the invention is introduced via a viral vector to smooth muscle cells in vitro, one with skill in the art will appreciate that an effective amount of the transgene may be readily determined by comparing the inhibition of proliferation of smooth muscle cells to which has been introduced the transgene, as compared to smooth muscle cells subjected to the same culture conditions, but to which the transgene has not been introduced, and determining the viral dose required to achieve maximal inhibition of smooth muscle cell proliferation. Inhibition of smooth muscle cell proliferation can be measured, for example, by determining a change in the number of cells in a culture with a hemacytometer, or by using a FACScan, or a Coulter Cell Counter.

Where a transgene encoding a CDKi of the invention is administered to a blood vessel, by administering a recombinant adenovirus containing a transgene encoding the CDKi, it will be understood that the "effective amount" of virus administered is clinically determined. For example, typically recombinant viral particles are highly concentrated, and as many particles as possible and safely tolerated are administered to the blood vessel. In another example, where, e.g., $10^{12}$ viral particles have been determined to result in inhibition of smooth muscle proliferation in a treated blood vessel following angioplasty (and so inhibiting restenosis of the blood vessel), a similar number of particles may be used in a blood vessel of similar size. Such clinical determinations are a matter of routine to those of skill in the art.

By "transducing" is meant the introduction of exogenous nucleic acid into a cell using a recombinant virus. A recombinant virus is made by introducing appropriate viral vector sequences encoding a protein of interest into a packaging cell line. By "introducing" nucleic acid is meant the introduction of exogenous nucleic acid into a cell by any means, including, without limitation, means known in the art as transfection, transduction, infection (introduction of exogenous nucleic acid with a virus), and transformation. For various techniques for manipulating mammalian cells, see Keown et al. (1990) *Meth. Enzymol.* 185: 527–537.

By "transgene" is meant a nucleic acid sequence encoding a desired protein or polypeptide fragment operably linked to one or more regulatory sequences such that the nucleic acid sequence is transcribed and translated when the transgene is introduced into a cell. Where the transgene is contained within a recombinant adenovirus (or other DNA viruses), the transgene typically comprises, in the following order, a promoter/enhancer, a splice acceptor site/splice donor site, a protein-encoding nucleic acid sequence, and a polyA signal. Where the transgene is contained within an RNA virus (e.g., a lentivirus), the transgene typically comprises, in the following order, a promoter/enhancer, a protein-encoding nucleic acid sequence, and a polyA signal. It should be noted that where a recombinant virus is used to deliver the transgene encoding the CDKi of the invention, the inserted transgene may also use regulatory sequences the regulatory sequences endogenous to the virus (e.g., a viral promoter/enhancer).

A polycistronic transgene comprising two protein encoding nucleic acid sequences separated by an IRES sequence is also within the definition of a transgene. By "regulatory sequence" is meant nucleic acid sequences, such as initiation signals, polyadenylation (polyA) signals, promoters, and enhancers which control expression of protein coding sequences with which they are operably linked. By "operably linked" is meant that the nucleic acid sequence encoding a protein of interest and transcriptional regulatory sequences are connected in such a way as to permit expression of the nucleic acid sequence when introduced into a cell. By "expression" of a nucleic acid sequence encoding a protein is meant transcription of that nucleic acid sequence as mRNA and/or transcription and translation of that nucleic acid sequence resulting in production of that protein.

By "nucleic acid sequence" is meant a single-stranded or double-stranded chain of two or more nucleotide bases including, without limitation, deoxyribonucleic acid (DNA), ribonucleic acid (RNA), analogs of either DNA or RNA, mRNA, and cDNA.

By "engineered" is meant using standard molecular biology techniques to modify a nucleic acid sequence (and the resulting encoded protein) (see general laboratory manuals Maniatis et al., *Molecular Cloning: A Laboratory Manual* (2nd ed.), Cold Spring Harbor Press, 1989; and Ausubel et al., *Current Protocols in Molecular Biology*, John Wiley & Sons, New York, N.Y., 1994). Engineered proteins and/or nucleic acids may be modified such that amino acid residues or nucleotide bases are added or subtracted, or even replaced with other amino acid residues or nucleotide bases.

In certain embodiments of the first aspect of the invention, the cyclin dependent kinase inhibitor is selected from the group consisting of a protein from the INK4 family or an active fragment thereof; a protein from the CIP/KIP family or an active fragment thereof; and a fusion protein comprising at least an active fragment of the protein from the INK4 family and at least an active fragment of the protein from the CIP/KIP family.

In certain embodiments of the first aspect of the invention, the cyclin dependent kinase inhibitor is a protein from the CIP/KIP family of CDKi's. In certain embodiments, the CDKi is a human $p27$ protein or is an active fragment of the human p27 protein, such as an active fragment selected from the group consisting of amino acids 25–93 of p27 protein and amino acids 12–178 of p27 protein. By "active fragment" is meant a polypeptide that encompasses at least the amino acid sequence required for inhibition of the appropriate cyclin dependent kinase which is targeted by the indicated CDKi (e.g., for human p27, see, Russo et. al. (1998) *Nature* 395:237–243). Methods for determining smooth muscle cell hyperproliferation and inhibition thereof are described below and include, without limitation, the rabbit balloon injury model. In a preferred embodiment, the cyclin dependent kinase inhibitor of the invention is a derived from a mammal, such as a a human.

In certain embodiments of the first aspect of the invention, the cyclin dependent kinase inhibitor is a protein from the INK4 family of CDKi's. In certain embodiment, the cyclin dependent kinase inhibitor is a human p16 protein or an active fragment thereof.

In a certain preferred embodiment, the cyclin dependent kinase inhibitor is a fusion protein comprising at least an active fragment of a first cyclin dependent kinase inhibitor and at least an active fragment of a second cyclin dependent kinase inhibitor. A "fusion protein" of the invention is a single polypeptide chain that comprises at least an active fragment of a first protein and at least an active fragment of a second protein, wherein the two active fragment s are joined either directly or indirectly with a peptide bond. It will be understood that fusion protein of the invention may comprise more than two proteins (or an active fragments thereof). Each an active fragment of a fusion protein may be from a separate CDKi, or may be from the same CDKi. For example, a fusion protein of the invention comprises an active fragment of the human p27 protein with the full length human p16 protein.

In a certain embodiment, the first cyclin dependent kinase inhibitor of a fusion CDKi of the invention is a protein from the CIP/KIP family of CDKi's, such as human p27. In a certain embodiment, the second cyclin dependent kinase inhibitor is a protein from the INK4 family of CDKi's, such as human p16. Exemplary cyclin dependent kinase inhibitor fusion proteins of the invention include W3, W5, W6, W7, W8, W9, and W10, each of which is described below. In preferred embodiments, the cyclin dependent kinase inhibitor is W7 or W9. Preferably, the cyclin dependent kinase inhibitor is W9.

Fusion proteins of the invention may also include a linker between the two joined active fragments. A "linker" is any chemical, synthetic, carbohydrate, lipid, polypeptide (or combination thereof) molecule positioned between and joined to two adjacent active fragments in a fusion protein. A preferred linker of the invention is a polypeptide chain consisting of one or more amino acid residues joined by amino acid bonds to the two active fragments. For example, a $(Gly_4Ser)_3$ linker may be positioned between the two active fragments in the fusion protein.

In accordance with the first aspect of the invention, the recombinant adenovirus employed to deliver the CDKi of the invention to a smooth muscle cell (by transducing that cell) lacks functional E1 and E4 regions. By "lacks a functional region" is meant that in a recombinant adenovirus, the indicated region is deleted or the expression of any of the proteins and/or RNAs encoded by the indicated region is abrogated In certain embodiments of this aspect of the invention, the adenovirus may be of any serotype. Such adenoviruses lacking functional E1 and E4 regions, and methods for generating them, are disclosed in Wang et al., U.S. patent application Ser. No. 08/552,839, filed Nov. 3,1995 (hereby incorporated by reference). In a certain embodiment, the adenovirus is replication-deficient. By "replication-deficient" is meant a recombinant adenovirus that is unable to reproduce itself in a cell other than a packaging cell that complements the missing viral functional region(s). Thus, a smooth muscle cell transduced with a replication-defective adenovirus will not provide de novo adenoviral particles. In a certain embodiment, the adenovirus of the invention that lacks a functional E1 region (or expression of any E1 region-encoded proteins) and a functional E4 region (or expression of any E4 region-encoded proteins) also lacks a second essential viral protein encoded by viral genes, such as E2 or E3 (or expression of any proteins encoded by these regions).

The CDKi-encoding sequences may replace one or more of the regions of the adenovirus genome (e.g., the E4 region or the E1 region). Into this region may be inserted promoter and/or enhancer sequences using standard molecular biology techniques (see, for example, Ausubel et al., supra). Such promoter/enhancer sequences may be constitutively active (e.g., the CMV promoter or the EF1α promoter), cell-type specific (e.g., a promoter of a gene that is specifically expressed by smooth muscle cells such as the SM22α gene promoter (described in PCT Publication No. WO98/15575 (PCT Application No. PCT/US97/16204) and in Solway et al. (1995) *J. Biol. Chem.* 270: 13460–13469), or inducible (eg., the cytokine-stimulated inducible nitric oxide synthase (iNOS) gene promoter). Numerous promoter/enhancer sequences are well known and their sequences available, for example, in the GenBank database (National Center for Biotechnology Information, National Institutes of Health, Bethesda, Md.). The inserted promoter (e.g., the CMV promoter) may then be operably linked to the nucleic acid sequence encoding the CDKi protein, which may then be operably linked to a poly A signal sequence (from, e.g., SV40 virus) to create a CDKi-encoding transgene.

In a preferred embodiment, the adenovirus of the invention is replication-deficient, and lacks a functional E4 region (or expression of any E4 proteins) and a functional E1 region (or expression of any E1 proteins). Preferably, the adenovirus of the invention is replication-deficient. One non-limiting way to make such a recombinant adenovirus expressing a CDKi protein is to replace the deleted E1 region sequences in a ΔE1/ΔE4 adenovirus vector with a CDKi-encoding transgene (e.g., a CDKi protein-encoding nucleic acid sequence operably linked to a CMV promoter/enhancer and an SV40 poly A signal). The recombinant adenovirus vector containing the transgene is then packaged in 293-E4 cells to produce infectious recombinant adenovirus particles (see Wang et al., U.S. patent application Ser. No. 08/552,839 filed Nov. 3, 1995). Alternatively, the CDKi-encoding transgene may replace deleted E4 and/or E3 regions.

The recombinant adenovirus encoding a CDKi of the invention may be used to transduce smooth muscle cells in vivo or in vitro. The amount of adenovirus used to transduce smooth muscle cells in vitro may be standardized by determining the multiplicity of infection (MOI) of the recombinant adenovirus, or by determining the actual number of viral particles based on the amount of viral DNA. Such standardization of viral particles is routine and is generally described in Phillipson et al., *Molecular Biology of Adenoviruses*, Virology Monograph, Springer Verlag, New York, N.Y., 1975.

In certain embodiments of the first aspect of the invention, the smooth muscle cells are in a mammal. The recombinant adenovirus comprising a transgene encoding a CDKi of the invention is administered to the mammal. In certain embodiments of the method of inhibiting hyperproliferation, the smooth muscle cells were induced to hyperproliferate by vascular injury. In certain embodiments, the injury was induced by angioplasty, stent placement, or vein engraftment. Preferably, the method is used in the case of restenosis induced by angioplasty.

Administration of a recombinant adenovirus in order to transduce smooth muscle cells in vitro or in vivo may be accomplished by any suitable method. For example, compositions that comprise recombinant adenoviruses may be diluted in serum-free culture media and added to cells cultured in vitro. Similarly, for in vivo delivery, compositions comprising recombinant adenoviruses comprising transgenes encoding the CDKi of the invention in a pharmaceutically acceptable carrier, such as buffered saline (see below), may be administered, e.g., to the smooth muscle cells at the blood vessel treatment site following angioplasty, by administration with a catheter. For example, the recombinant adenovirus of the invention is administered to a patient undergoing angioplasty or afflicted with restenosis within a previously treated blood vessel (or having a predisposition to develop restenosis).

To deliver the transgene encoding a CDKi of the invention to smooth muscle cells, standard administration protocols may be employed. Where the injury is induced by angioplasty, for example, the recombinant adenovirus of the invention is administered to the smooth muscle cells at the site of the treated blood vessel. Any appropriate route of administration may be employed, including, without limitation, intravenous and intra-arterial. Preferably, the recombinant adenovirus encoding a CDKi protein of the invention is administered locally to the affected area (e.g., directly into a blood vessel immediately following treatment of the vessel with angioplasty), or may be administered to the blood stream directly upstream of the affected area. Preferably, recombinant viruses of the invention are administered locally to the site of the smooth muscle cells affected with hyperproliferation (e.g., to the site of the vessel following angioplasty treatment) by way of an infusion catheter or to the outside of the vessel (e.g., the adventitia) by way of an arterial cuff. A recombinant adenovirus of the invention is preferably administered to an individual in a pharmaceutically-acceptable diluent, carrier, or excipient. One exemplary pharmaceutically-acceptable carrier is physiological saline. Other pharmaceutically-acceptable carriers and their formulations are well-known and generally described in, for example, *Remington's Pharmaceutical Sciences* (18th Edition, ed. A. Gennaro, Mack Publishing Co., Easton, Pa., 1990).

If desired, treatment of a patient with the smooth muscle cell hyperproliferation-inhibiting reagents and compositions of the invention may be combined with more traditional therapies or other smooth muscle cell proliferation-inhibiting reagents.

In a second aspect, the invention provides a recombinant lentivirus that comprises a transgene encoding a cyclin dependent kinase inhibitor (CDKi). Recombinant lentiviruses can be engineered to comprise a transgene encoding a CDKi of the invention according to standard techniques. For example, recombinant lentiviruses can be generated using the lentivirus vectors described below in Example XIV.

The CDKi according to the second aspect of the invention, are as described for the first aspect of the invention. In certain embodiments, the recombinant lentivirus is replication-deficient.

In a third aspect, the invention provides a therapeutic composition comprising a pharmaceutically acceptable carrier and a recombinant lentivirus that comprises a transgene encoding a cyclin dependent kinase inhibitor. Preferably, the recombinant lentivirus is replication-deficient.

In a fourth aspect, the invention provides a method for treating a condition associated with smooth muscle cell hyperproliferation comprising administering to a patient at risk for the condition, a therapeutically effective amount of a therapeutic composition comprising a pharmaceutically acceptable carrier and a recombinant lentivirus that comprises a transgene encoding a cyclin dependent kinase inhibitor, wherein the condition is inhibited. Preferably, the recombinant lentivirus is replication-deficient.

By "therapeutically effective amount" is meant the total amount of each active component of a therapeutic composition that is sufficient to show a meaningful patient benefit. When administered to an animal having a condition associated with smooth muscle cell hyperproliferation, a therapeutically effective amount is an amount sufficient to slow proliferation of a smooth muscle cell in the treated blood vessel to prevent or inhibit restenosis and/or vessel occlusion.

In various embodiments of the fourth aspect of the invention, the condition is restenosis. In certain embodiments, the restenosis is induced by an injury, where the injury is induced by angioplasty, stent placement, or vein engraftment into the arterial system.

The invention now being generally described will be more readily understood by reference to the following examples which are included merely for purposes of illustration of certain aspects and embodiments of the present invention, and are not intended to limit the invention.

EXAMPLE I

Generation of p27/p16 Fusion Proteins

To create more potent anti-proliferative molecules that possess the activities of both the INK4 (p16) and CIP/KIP (p27) families, a number of recombinant CDKi's were created that fused the parental human p16 and p27 molecules, or their derivatives. The engineered CDKi's included fusion proteins of p16 fused to 5' and 3' truncated $p^27$ molecules. These fusion proteins were designed to increase the protein's half-life and eliminate potential phosphorylation sites involved in the negative regulation of CDKi activity. The p27-p16 fusion proteins interacted with the CDK4/cyclinD, CDK2/cyclinA, and CDK2/cyclinE complexes and inhibited cell cycle progression at multiple points.

To generate the following non-limiting, representative CDKi fusion proteins of the present invention (and nucleic acid sequences encoding these proteins), the published sequences of the human p16 and p27 molecules were utilized. The nucleic acid (SEQ ID NO: 25) and amino acid (SEQ ID NO: 26) sequence of human p27 is available as GenBank Accession No. U10906 (Polyak et al. (1994) Cell 78: 56–66). The nucleic acid (SEQ ID NO: 27) and amino acid (SEQ ID NO: 28) sequence of human p16 is available as GenBank Accession No. L27211 (Serrano et al. (1993) Nature 366: 704–707; Okamoto et al. (1994) Proc. Natl. Acad. Sci. USA 91: 11045–11049). To construct the representative, non-limiting CDKi fusion proteins of the invention, in general, PCR primers were used to insert a NdeI cloning site followed by sequence encoding 6xHis and an epitope tag from the influenza virus hemagglutinin protein (HA tag) at the 5' end of full length p27 or truncated $p27_{25-93}$ and $p27_{12-178}$. In each instance, the CDKi gene was followed by an amber stop codon with SalI cloning site. The NdeI-SalI fragments were amplified by Deep Vent polymerase (commercially available from New England Biolabs, Beverly, Mass.) and cloned into plasmid pT7-7 (commercially available from US Biological (USB), Swampscott, MA) to yield pT7-His6-HA-p27, pT7-His6-HA-$p27_{25-93}$ and pT7-His6-HA-$p27_{12-178}$. To generate fragments without a stop codon and a $(Gly_4Ser)_3$ inker, an alternate set of 3' PCR primers were used to insert sequence coding for a $(Gly_4Ser)_3$ linker in place of the stop codon with SalI cloning site at the 3' end. These NdeI-SalI amplified fragments were then subcloned into a NdeI and XhoI digested pKS plasmid containing full length p16, with the initiating ATG removed, generating an open reading frame in which the various p27 derivatives and full length p16 are linked by $(Gly_4Ser)_3$, histidine, and aspartic acid. The representative, non-limiting CDKi proteins of this example are schematically depicted in FIG. 1, and were constructed as follows:

To construct the nucleic acid sequence encoding the p27-p16 fusion protein (i.e., N-terminal p27 and C-terminal p16) having a $(Gly_4Ser)_3$ hinge region between the p27 and p16 portions (W3), the $p^{27}$ coding sequence was first PCT amplified using the following primers:
N-terminal primer, which carries an NdeI site and 6 histidine codons that are inserted between the ATG and the second amino acid of p27 (SEQ ID NO: 1):

5'-GCGGCCGGTCATATGCACCACCATCACCATCA CTCAAACGTGCGAGTGTCT-3'; and

C-terminal primer, which carries the $(Gly_4Ser)_3$repeat and EcoRI, SalI, and HindIII restriction sites and eliminates the stop codon of p27 (SEQ ID NO: 2):

5'-GCCGCCGGCGTCGACTCGGCCGAATTCGGATC CACCCCCGCCGGAACC- GCCACCCCCGCTGCCCCCGCCACCCGTTTGAC GTCTTCTGAGGCCAGG-3'.

The p27 PCR product was digested with NdeI and HindIII and inserted into pT7-7 linearized with NdeI and HindIII. The resulted construct was digested with EcoRI and SalI and a full length p16 PCR product was inserted as an EcoRI-XhoI fragment. The position of the EcoRI site allows the in-frame insertion of p16. The rest of the hinge region between the p27 and p16 coding sequences is derived from the 5' end of the p16 cDNA. The nucleic acid and amino acid sequence of W3 are provided, respectively, in SEQ ID NO: 3 and SEQ ID NO: 4.

A nucleic acid sequence encoding a second p27-p16 fusion protein, W4, was generated, where the p27 and p16 portions were not separated by a $(Gly_4Ser)_3$ hinge region. The W4-encoding nucleic acid sequence construct includes a 5' EcoRI site, along with the coding sequence for a N-terminal HA tag, and a 3' NotI site. The nucleic acid and amino acid sequence of W4 are provided, respectively, in SEQ ID NO: 5 and SEQ ID NO: 6.

Two p16-$p2^7$ fusion proteins (i.e., N-terminal p16 and C-terminal p27), W5 (having a $(Gly_4Ser)_3$ hinge region located between the p16 and p27 portions) and W6 (not having a $(Gly_4Ser)_3$ hinge region) were similarly generated. The nucleic acid and amino acid sequence of W5 are provided, respectively, in SEQ ID NO: 7 and SEQ ID NO: 8. The nucleic acid and amino acid sequence of W6 are provided, respectively, in SEQ ID NO: 9 and SEQ ID NO: 10.

In addition, a series of truncated versions of p27 designed to increase the protein half-life were fused to full-length p16 at the N-terminus. In one p27 truncation, $p27^{12-178}$, the first 12 N-terminal and the last 20 C-terminal amino acids were removed from full length p27 to remove a CDK consensus phosphorylation site (TPKK) at amino acids 187–190, two other potential phosphorylation sites for proline directed kinases, at amino acids 178–181 (SPN), and a weak CDK phosphorylation site (SP5L) at amino acids 10–13 (Sheaff et al. (1997) Genes & Dev. 11: 1464–1478; Morisaki et al. (1997) Biochem. Biophys. Res. Commun. 240: 386–390). The nucleic acid and amino acid sequences of this truncated p27 protein (12aa–178aa) are shown in SEQ ID NO: 11 and SEQ ID NO: 12, respectively, which provide a polypeptide of the formula EcoRI-ATG-HA epitope-p27 (12–178aa)-Stop-NotI.

W7 comprises amino acids 12-178 of p27 fused to full length p16, where the p27 and p16 portions are separated by a $(Gly_4Ser)_3$ hinge region. The nucleic acid and amino acid sequence of W7 are provided, respectively, in SEQ ID NO: 13 and SEQ ID NO: 14. W8 comprises amino acids 12–178 of p27 fused to full length p16, where the $p^{27}$ and p16 portions are not separated by a $(Gly_4Ser)_3$ hinge region. The nucleic acid and amino acid sequence of W8 are provided, respectively, in SEQ ID NO: 15 and SEQ ID NO: 16.

In a second truncation of p27, $p27_{25-93}$, only the CDK inhibitory domain of p27 (amino acids 25–93) was retained. This domain contacts both the CDK and cyclin binding subunits and is sufficient for kinase inhibition, while lacking the nuclear localization signal at amino acids 152–166 and the QT domain, a potential site for protein interactions, at amino acids 144–194 (Russo et al. (1998) Nature 395: 237–243). Thus, the $p27_{25-93}$CDKi was created to eliminate amino acid residues that may play a role in targeting the parental p27 molecule to the ubiquitin- proteosome degradation pathway or may play a role in p27 phosphorylation. The nucleic acid and amino acid sequences of this truncated p27 protein (25aa–93aa) are shown in SEQ ID NO. 17 and SEQ ID NO: 18, respectively, which provide a polypeptide of the formula EcoRI-ATG-HA epitope-p27 (25–93aa)-Stop-NotI.

The $p27_{25-93}$fragment were fused to the N-terminus of p16 with (W10) or without (W9) the $(Gly_4Ser)_3$hinge (FIG. 1). The nucleic acid and amino acid sequence of W9 are provided, respectively, in SEQ ID NO: 19 and SEQ ID NO: 20. The nucleic acid and amino acid sequence of W10 are provided, respectively, in SEQ ID NO: 21 and SEQ ID NO: 22.

W3, W8, and W10 were further subcloned into a modified pGEX4T-1 plasmid (Pharmacia Biotech, Uppsala, Sweden) (where a NdeI cloning site was inserted between the BamHI and EcoRI sites) as NdeI-NotI fragments to generate glutathione S-transferase (GST) tagged fusion proteins. A similar strategy was used to generate fusion proteins without the $(Gly_4Ser)_3$ linker (i.e., W4 ($p2^7$-p16), W7 ($p27_{12-178}$-p16 fusion CDKi W9 ($p27_{25-93}$-p16)). The nucleic acid and amino acid sequences of the $p27_{25-93}$-p16 fusion CDKi, W9, without the HA tag and six histidine residues are provided in SEQ ID NO: 23 and SEQ ID NO: 24, respectively.

p27, $p27_{25-93}$, and $p27_{12-178}$ proteins were expressed in E. coli BL21 strain using the pT7 plasmids described above. For protein expression, cells were grown in LB+50 mg/ml ampicillin at 37° C. to $OD_{600}$=0.8 and protein expression was induced by IPTG (final; conc.: 2 mM) for 4 hours as 37° C. Cells were collected and the pellet was frozen at -80° C. The preparation of the cell lysate and binding to a $Ni^{2+}$ charged sepharose resin (Invitrogen Corp, San Diego, Calif.; Catalog no. R801) was done according to the manufacturer's instruction (Invitrogen; see also Hochuli et al. (1987) *J. Chromatography* 411:177–184; Janknecht et al. (1991) *Proc. Natl. Acad. Sci. USA* 88: 8972–8976). The bound proteins were eluted with 50 mM, 200 mM, 350 mM, and 500 mM imidazol and the fractions were analyzed on SDS/PAGE. The 200 mM, 350 mM, and 500 mM imidazol fractions were collected, dialysed against 1×PBS (1 mM $KH_2PO_4$, 10 mM $Na_2HPO_4$, 137 mM NaCl, 2.7 mM KCl, pH 7.4)+10% glycerol and stored at -80° C. in aliquots. Approximately 25% of the prep was the protein.

$p27_{25-93}$ and $p27_{12-178}$ were further purified by gel filtration column chromatography using a Superdex 75 FPLC column equilibrated with 10% glycerol in PBS. Expression and purification of the GST-tagged W3, W4, W7, W8, W9, and W10 fusion proteins was essentially as described (Gyuris et al. (1993) *Cell* 75: 791–803). The purified GST-fusion proteins were then buffer exchanged by dialysis into 50 mM Tris-HCl pH 8.0, 150 mM NaCl, 2 mM $CaCl_2$. The GST domain was removed from the fusion proteins by enzymatic cleavage with 1 unit (USB units) of thrombin/mg of protein/hour (thrombin commercially available from USB). Following cleavage, the thrombin was inactivated with 2 fold molar excess of PPACK (USB). The cleaved GST moiety was then removed by passing the protein solution over a column of glutathione-Sepharose. Protein concentration was determined using a protein assay (BioRad, Cambridge, Mass.) with bovine serum albumin (BSA) as a standard. In order to more accurately determine the concentration and purity of the specific proteins in each of the preparations, the protein samples were subjected to SDS-PAGE, and stained with coomassie blue. The stained gels were analyzed using the Gel Doc 1000 image analysis system and Molecular Analyst software (BioRad).

The p27 and p16 CDKi's appear to fold correctly in all of the fusion protein CDKi's, as the biochemical data indicates that the p27 moieties were functional and intra-cellular staining with anti-p16 antibodies indicate that at least at a gross level, the p16 molecules were folded correctly.

EXAMPLE II in vitro Kinase-Inhibiting Activities of the CDKi Proteins

The natural substrates for $p2^7$ and p16 CDKi's are cyclin-dependent kinase (CDK) complexes that are formed via the association of different catalytic CDK and regulatory cyclin subunits. The CDK4/cyclin D and CDK6/cyclin D complexes regulate progression through $G_1$, phase, the CDK2/cyclin E kinase regulates the $G_1$/S transition, the CDK2/cyclin A complex drives the cells through S-phase, and the entry and exit from mitosis is controlled by the CDC2/cyclin B complex (Sherr, C. J. (1996) *Science* 274: 1672–1677). CDKi's regulate the activity of the CDK complexes through a combination of phosphorylation events and physical association (Morgan, M. (1995) *Nature* 374: 131–134). The redistribution of CDKi's between the different CDK/cyclin complexes during the cell cycle coordinates the timing of activation and de-activation of their kinase activity (Sherr and Roberts (1995) *Genes and Dev.* 9: 1149–1163).

To determine the ability of the CDKi proteins of the invention, their abilities to inhibit the in vitro kinase activity of CDK4/cyclin D1, CDK2/cyclin E, and CDC2/cyclin B complexes was determined. The purity of the various p27-p16 fusion proteins, p27, and p16 preparations were normalized using p16 and p27 specific antibodies.

Active CDK4/cyclin D1, CDK2/cyclin E, and CDC2/cyclin B complexes were obtained from Sf9 insect cells transfected with baculoviruses expressing recombinant cyclins and CDK's. Briefly, the assay employed Sf9 cell extracts that were made from cells that were coinfected with the proper CDK and cyclin expression constructs. Typically, 44 mg of Sf9 extract in 50 ml of 50 mM Tris-HCl pH 7.6, 10 mM $MgCl_2$, 1 mM DTT, 25 mM ATP, 10 mCi $^{32}P$-γ-ATP was used in the absence of the presence of the particular inhibitor (inhibitor concentration was between 25 nM to 1 mM). Partial purification of CDK4/cydin D1 was achieved by a 20–40% ammonium sulfate preparation of the cell lysate and was used in the assays. CDK2/cyclin E was purified to greater than 90% and pretreated with CDK-activating kinase (CAK) (Morgan, M., supra) for full activation. CDC2/cyclin B was expressed as a GST fusion protein (CDC2/GST-cyclin B) and purified on glutathione-Sepharose column, cleaved by thrombin, and followed by another glutathione-Sepharose separation for the removal of the cleaved GST. GST-fused Rb (glutathione S-transferase fusion with amino acids 379–928 from the C terminus of pRB; GST-Rb) was used as a substrate for the CDK4/cyclin D1 and CDK2/cyclin E assays; histone H1 was the substrate for CDC2/cyclin B. The reaction was carried out at 30° C. for 30 minutes using 2 mg of substrate. These assays were carried out in 96 well plates (Nunc, Naperville, Ill.) and monitored by γ-$^{32}P$-ATP incorporation.

The reactions were initiated by addition of the insect cell-produced CDK (e.g., CDC2/cyclin B) and the *E. coli*-produced CDKi (e.g., p27 and W9). The concentrations of GST-Rb and histone H1 were 4.4 mM and 19 mM, respectively, and the concentration of ATP was 50–60 mM. The reaction mixtures contained 50 mM Tris-Cl pH 7.5, 10 mM $MgCl_2$, and 1 mM DTT in a total volume of 50 or 100 μl. After incubation at 30 ° C. for 10–20 minutes, the reaction was terminated by the addition of a stop solution containing EDTA. The phosphorylated substrates were captured either by GST-Sepharose or TCA precipitation and then monitored for radioactivity (Microplate Scintillation Counter, Packard, Meriden, Conn.).

The concentration of CDKi protein at which 50% of the kinase activity was blocked (IC50) was calculated for various cyclin/CDK pairs. The results are indicated in Table I (below) and in FIG. 1 (three columns labeled CDK4/cyclin D1 (nM), CDK2/cyclin E (nM), and CDK2/cyclin B (nM)). Moreover, the inhibition constant, $K_i$ for the inhibition of CDK4/cyclin D1 by p27/p16 fusion protein was determined to be 23 nM, compared to a $K_i$ of 75 nM for p16 inhibition of the same CDK4 complex.

TABLE I

Inhibition of Cyclin Dependent Kinase Complexes by
p27-p16 Fusion Protein

| inhibitor | CDK4/cyclinD1 | CDK2/cyclinE | CDK2/cyclinA | cdc2/cyclinB |
|---|---|---|---|---|
| p27-p16 | 25 nM | 30 nM | 25 nM | 15 nM |
| p27 | 63 nM | 52 nM | 65 nM | 20 nM |
| p16 | 250 nM | >500 nM | >500 nM | >500 nM | nM = nanomolar

As shown in Table I and FIG. 1, p16 was a potent inhibitor of the CDK4/cyclin D1 kinase. In contrast, p27 was a powerful inhibitor of all three kinase complexes. The various p27 modifications did not positively impact the monomeric or fusion protein CDKi's inhibitory activity in vitro (see FIG. 1). In general, the order of the p16 and p27 CDK in the fusion CDKi does not appear to impact the activity of the fusion CDKi. Moreover, the $(Gly_4Ser)_3$ hinge region is not necessary to retain $p27$ function in the fusion CDKi.

Thus, in vitro kinase inhibition experiments indicated that the potency of the purified $p27_{12-178}$, $p27_{25-93}$ or the fusion p27/p16 proteins (W3, W4, W7, W8, W9, and W10) were not appreciably different from that of full-length p27 or an equimolar mixture of p16 and p27. The activity of the CDK4/cyclin D1 complex was inhibited by both p16 and p27.

EXAMPLE III

Construction of Recombinant Adenoviruses Expressing CDKi Proteins

Figure 2:
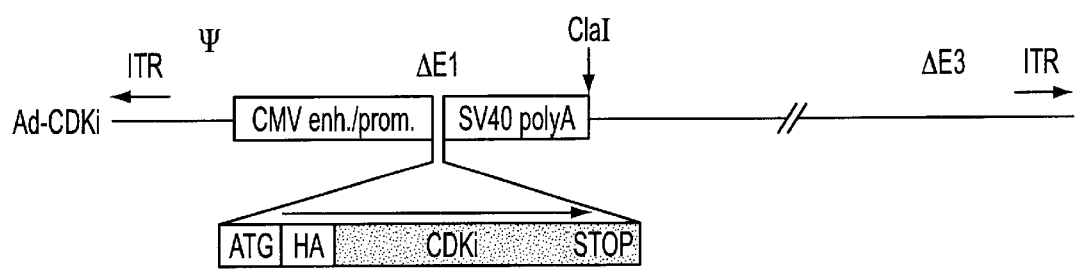
FIG. 2 is a schematic representation of the genomic structure of recombinant adenoviruses that express CDKi's. The expression of the inhibitors is regulated by the CMV enhancer and promoter and the SV40 poly A sequence. In the constructs depicted in this schematic diagram, every inhibitor is fused to the HA epitope tag. The ATG is in the context of the optimal Kozak sequence.
Figure 3A:
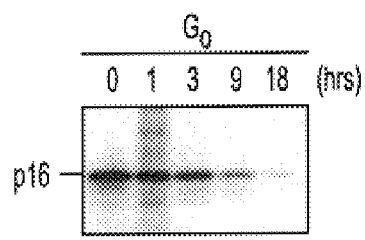
FIG. 3 is a photographic representation of a series of autoradiographs depicting the turnover rate of adenovirus-expressed CDKi's (AV-CDKi's) in transduced asynchronously growing human coronary artery smooth muscle cells (CASMCs) ($A_s$; middle column) as compared to transduced quiescent CASMCs ($G_0$; left column). Twenty-four hours following infection at a MOI of 50, cells were labeled for 2 hours with $^{35}$S-methionine and then chased with "cold" medium for the times indicated. Equivalent amounts of total cell extract from the transduced asynchronous ($A_s$) and quiescent ($G_0$) cells were immunoprecipitated using antibodies bound to protein A-Sepharose. With the exception of AV-p27, a p27 specific antibody was used for all immunoprecipitates of AV-CDKi-infected cells. For the immunoprecipitation of p16 from AV-p16 infected cells a p16 specific antibody was used. The precipitates were separated by SDS-PAGE, the gels vacuum dried and exposed to film. The far right column shows the results of a parallel experiment conducted with asynchronous ($A_s$) cells transduced with AV-W7 and harvested on days 1, 2,3,4, or 5, following a 2 hour pulse.
Figure 3B:
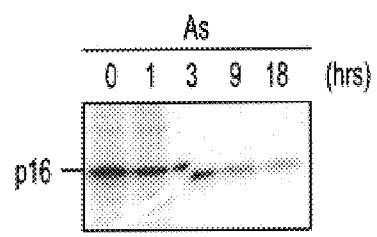
Figure 3C:
Figure 3D:
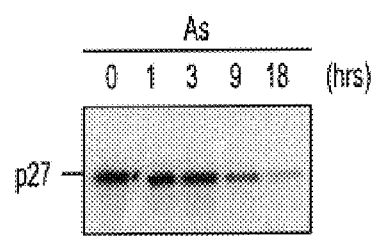
Figure 3E:
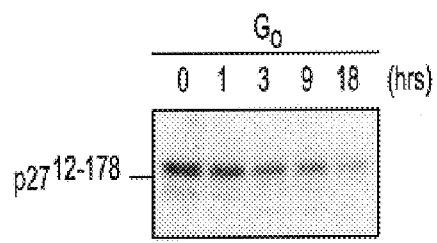
Figure 3F:
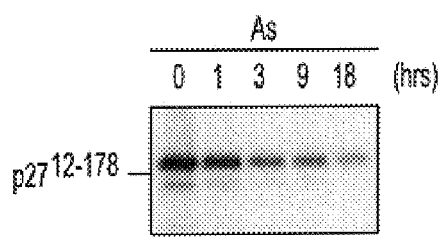
Figure 3G:
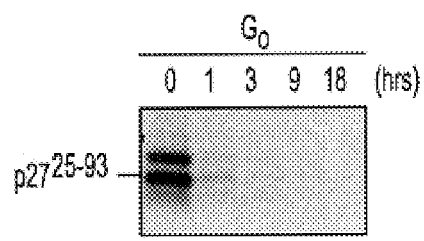
Figure 3H:
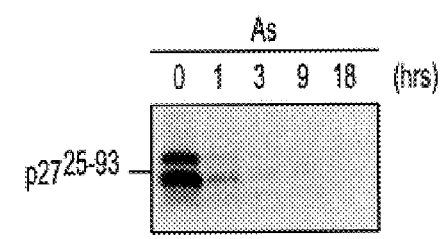
Figure 3I:
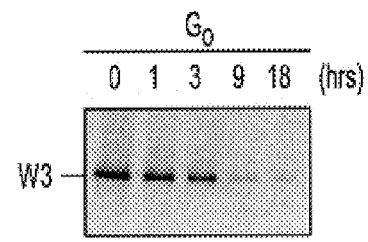
Figure 3J:
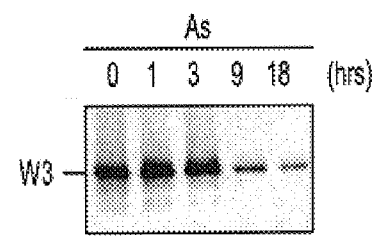
Figure 3K:
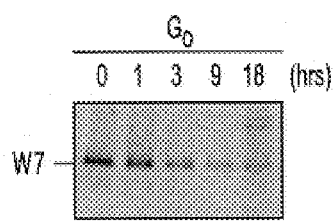
Figure 3L:
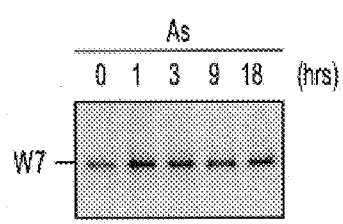
Figure 3M:
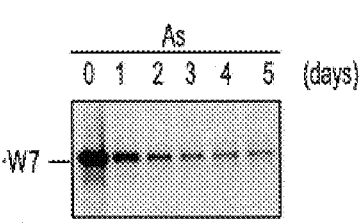
Figure 3N:
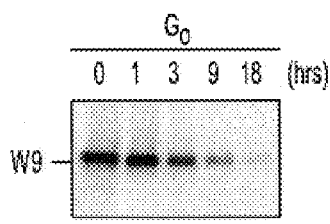
Figure 3O:
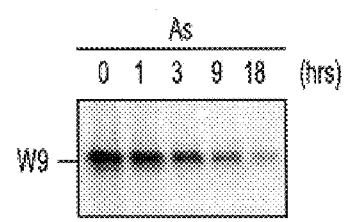
Figure 4A:
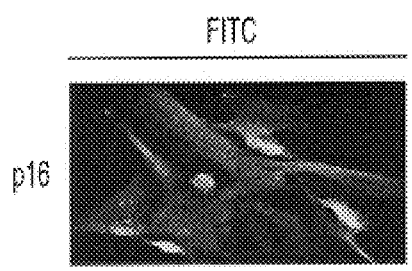
FIG. 4 is a representation of a series of photographs showing the comparison of the subcellular localization of various adenovirus-expressed CDK inhibitors in CASMCs.
Figure 4B:
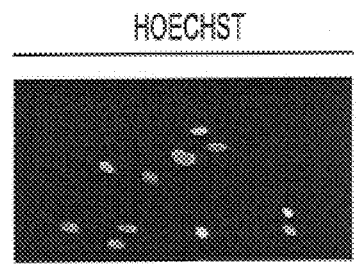
Figure 4C:
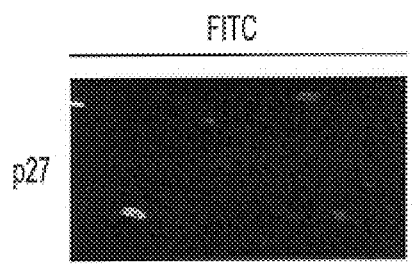
Figure 4D:
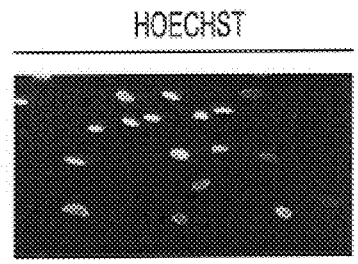
Figure 4E:
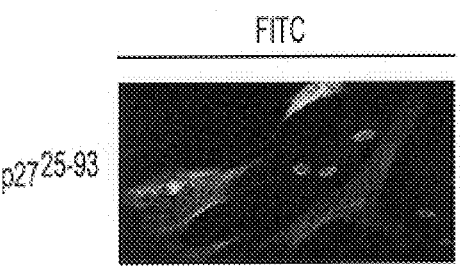
Figure 4F:
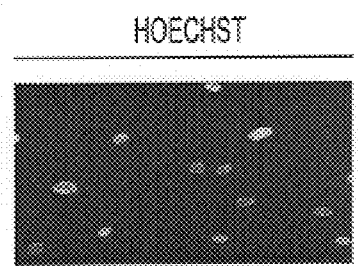
Figure 4G:
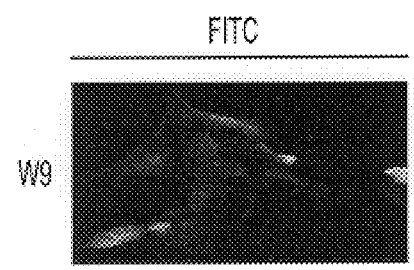
Figure 4H:
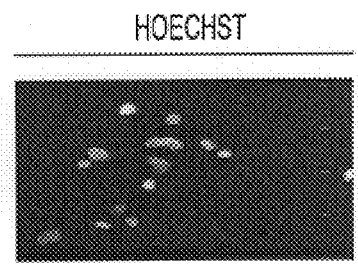

Based on the in vitro kinase data, a representative of each of the CDKi species was selected for further analysis. The genes encoding p16, p27 and its derivatives, W3, W7, or W9 CDKi were introduced into the E1 region of a replication deficient, E1 and E3 deleted (ΔE1/ΔE3) recombinant adenovirus (FIG. 2). The adenovirus vector system used for the construction of replication deficient, E1 region- and E3 region-deleted, E4 region-containing adenovirus 5 (Ad5) recombinants was purchased from Microbix Biosystems Inc. (Toronto, Ontario, Canada). The six-his residue, HA-tagged CDKI's were expressed under the control of the CMV promoter/enhancer and the SV40 polyA signal (FIG. 2). It should be noted, however, that the presence or absence of either the his tag and/or the hemaggluginin (HA) tag does not appear to affect the smooth muscle cell proliferation-inhibiting activities of any of the CDKi of the invention. Accordingly, the CDKi of the invention may be used as smooth muscle cell proliferation-inhibiting agents with or without the his tag and/or the hemaggluginin (HA) tag.

The ΔE1/ΔE3 adenovirus encoding $p^{27}$ (ΔE1/ΔE3-AV-p27, or simply AV-p27) was constructed by in vivo recombination in 293 cells following the manufacturer's instructions (Microbix). 293 cells, a human embryonic kidney cell line which contains the E1 region of the adenovirus and, therefore, provides the E1 region gene products lacking in the E1-deleted recombinant adenoviruses, are commercially available from the American Type Culture Collection, Manassas, VA (ATCC No. CRL 1573) (Graham et al. (1977) J. Gen. Virol. 36: 59–72). ΔE1/ΔE3-AV-p27 DNA was isolated from the amplified virus and digested with ClaI. This digest removed the p27 expression cassette (i.e., nucleic acid sequence encoding p27 operably linked to regulatory sequences) and the left inverted terminal repeat (ITR) and packaging signals of Ad5 (see FIG. 2). HA-tagged p16, $p27_{25-93}$, $p27_{12-178}$, W3, W7, and W9 molecules were cloned into a plasmid, pKS-ITR-CMV, which contains the expression cassette as well as the left ITR and packaging signals with flanking EcoRV and ClaI restriction sites. The order of the functional elements is the following from 5' to 3': EcoRV-left ITR-packaging signal-CMV enhancer/promoter-CDKi insert-SV40 polyA-ClaI. The EcoRV-ClaI fragments containing the CDKi inserts were ligated to the deleted, large Ad5 DNA in vitro and the ligated DNA was transfected into 293 cells.

Infectious, recombinant virus particles were rescued from 293 cells. The unligated, large Ad5 fragment was unable to generate infectious viruses alone because of the lack of the left ITR and packaging signal that are essential for virus replication. Infectious recombinants formed only when the small EcoRV-ClaI fragment containing the left ITR, packaging signal, the expression cassette and the CDKi insert was ligated to the ClaI digested end of the Ad5 DNA re-creating an infectious Ad5 recombinant virus DNA.

EXAMPLE IV

Stability of CDKi Proteins Delivered by Recombinant Adenovirus

To determine the half-life of the various CDKi in CASMC's, pulse-chase experiments were performed using growth arrested and proliferating CASMC's transduced with the adenoviruses lacking functional E1 and E3 regions, containing the entire E4 region, and expressing the various CDKi (ΔE1/ΔE3-AV-CDKi's, or simply AV-CDKi's).

Human coronary artery smooth muscle cells (CASMCs) were obtained from Clonetics (Walkersville, Md.). Low passage CASMC (less than passage 10) were plated at 3500 cells/cm$^2$ in complete SMC media (Clonetics, plus 5% FBS and growth factors) and allowed to recover overnight. For proliferating cells, cultures were maintained throughout in complete SMC media. For quiescent cells, cultures were serum starved for 48 hours in low serum media (SMC media with 0.05% FBS and 1:100 growth factors).

Growth arrested ($G_0$) and proliferating ($A_s$) CASMC were transduced at an MOI of 50 with the various recombinant adenoviruses expressing CDKi's. Twenty-four hours later, the cells were radiolabeled ("pulsed") for 2 hours in media containing $^{35}$S-methionine. The $^{35}$S-methionine containing media was then removed and replaced with media containing an excess of non-radiolabeled amino acids, and the cells "chased" for 0, 1, 3, 9, 18 hours and 0, 1, 2, 3, 4, and 5 days. Cell pellets were lysed in 50 mM Tris-Cl pH 7.5, 250 mM NaCl, 0.5% NP-40, 50 mM NaF, 5mM EDTA, 1 mM PMSF, 1 mM Sodium Vanadate, and protease inhibitors. Protein concentrations were determined using a protein assay (Biorad) with bovine serum albumin (BSA) as a standard. Equivalent amounts of total protein from the cells were then immunoprecipitated using antibodies bound to protein A-sepharose. The antibodies used were p27 (Kip1, commercially available from Transduction Laboratories, Lexington, Ky.), and p16-C20 (commercially available from Santa Cruz Biotech., Santa Cruz, Calif.). The immunoprecipitates were separated by SDS-PAGE, and the gels vacuum dried and exposed to film. Estimated half life was determined from the radiolabeled proteins on the autoradiographs, which were analyzed using the Gel Doc 1000 image analysis system and Molecular Analysts software (Biorad).

Figures 3, 7B:
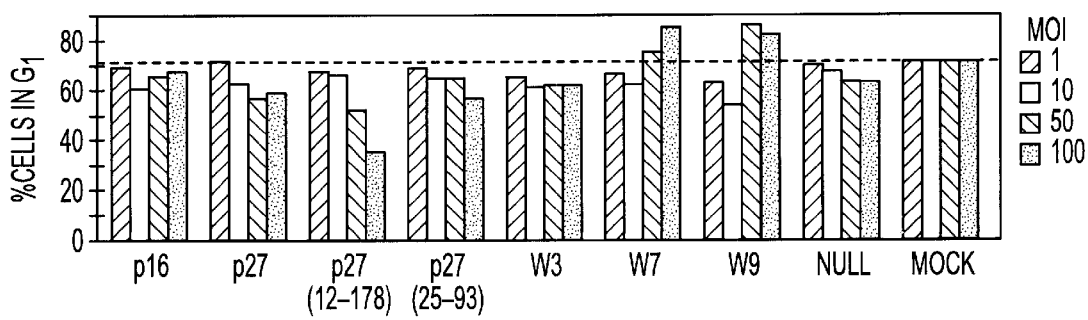

The observed molecular weights of the expressed, HA epitope tagged proteins corresponded to the expected sizes:

p27, approximately 30 kD; p27$_{12\text{-}178}$, approximately 28 kD; p27$_{25\text{-}93}$, approximately 10 kD; p16, approximately 19 kD; W3, approximately 48 kD; W7, approximately 46 kD; and W9, approximately 30 kD (FIG. 3). Interestingly, in AV-p27$_{25\text{-}93}$ infected cells, a protein band with the apparent molecular weight of approximately 24 kD was observed. The band was recognized by both p27 and HA epitope specific antibodies suggesting that it might be a stable dimer of two p27$_{25\text{-}93}$ molecules.

The kinetics of signal decay from the immunoprecipitated CDKi's was assessed by autoradiography at specific time-points (FIG. 3 and summarized in FIG. 1, two far right columns labeled "Half-Life (hrs)"). The half-life of the CDKi's was estimated as the time-point at which half the original CDKi protein signal remained. The half-lives of adenovirus expressed p$^{27}$ and p16 were similar, approximately 3 hours in quiescent cells. The half-lives of the truncated p27 derivatives were reduced compares to the full-length p27 molecule. The half-life of p27$_{12\text{-}178}$ was approximately 2 hours in quiescent cells and approximately 1 hour in proliferating cells. The p27$_{25\text{-}93}$ was extremely unstable with a half-life of less than 1 hour in CASMC's. The half-lives of the fusion protein CDKi, W3 and W9, were similar to the p27 molecule: approximately 2 hours in quiescent cells (G$_0$ cells) and approximately 6.5 and 4.5 hours, respectively, in proliferating cells. While the half-life of the W7 fusion protein was similar to the other CDKi in growth arrested SMC, it demonstrated a strikingly longer half live in proliferating cells (approximately 20 hours; see FIG. 3, far right panel). This represented an increase of at least 6-times and 20-times in stability over the contributing p16 and p27$_{12\text{-}178}$ molecules, respectively.

In quiescent CASMC (G$_0$ cells), the p16, p27, W3, W7, and W9 proteins all had half-lives of 2 to 3 hours (see FIG. 1). In proliferating cells(A$_s$), the W7 protein demonstrated a half-life of 20 hours.

EXAMPLE V

Adenovirus Delivered p16 p27$_{25\text{-}93}$, and W9 CDKi Localized to Both the Nucleus and the Cytoplasm of Transduced Cells To determine if the various CDKi's demonstrate differential subcellular localization, the adenovirus expressed CDKi's were examined by immunofluorescent staining of proliferating CASMC's using HA epitope specific antibodies. These studies revealed a very profound dichotomy in the localization of these proteins. The p 27, p27$_{12\text{-}128}$, W3, and W7 proteins predominantly localize to the nucleus (FIG. 4 and data not shown), although a small fraction (less than 5%) of ΔE1/ΔE3 AV-p27 and ΔE1/ΔE3 AV-W3 transduced cells were observed in which the protein localized to both the nucleus and the cytoplasm. In contrast, the p16, p27$_{25\text{-}93}$, and W9 CDKi proteins were present both in the nucleus and the cytoplasm (FIG. 4). Thus, W9 localized to both the nucleus and the cytoplasm, while W7 and W3 were found predominantly in the nucleus.

EXAMPLE VI

Efficacy of Recombinant Adenoviruses Encoding CDKi in Transducing Cells of the Vasculature To evaluate transduction efficiency of cells of the vasculature by ΔE1, ΔE3 deleted adenovirus, cultures of quiescent primary coronary artery smooth muscle cells (CASMC), aortic smooth muscle cells (AoSMC), coronary artery endothelial cells (CAEEC), and control HeLa cells were incubated with increasing does of a ΔE1, ΔE3 adenovirus encoding the β-gal transgene. Human coronary artery smooth muscle cells (CASMC) and aortic smooth muscle cells (AoSMC) were obtained from Clonetics Walkersville, Md.) and maintained in SMC media (Clonetics) supplemented with 5% fetal bovine serum (FBS). Human coronary artery endothelial cells (CAEC) were obtained from Clonetics (Walkersville, Md.) and maintained in EBM media supplemented with 5% bovine serum and growth factor supplements recommended by Clonetics. HeLa cells were maintained in DMEM containing 10% FBS.

Quiescent CASMC, AoSMC, CAEC or HeLa cells were seeded at confluency in the appropriate media containing 5% FBS and the cells were infected 24 hours later with ΔE1/ΔE3 AV-CMV-Lac-Z at MOI of 10, 30 and 100. The next day, virus was removed and replaced with fresh media. The cells were harvested 4 days later, and the β-gal positive cells were detected using fluorescein di-β-D-galactopyranoside (FDG) substrate (Sigma, St. Louis, Mo.) and quantified by FACS analysis.

Non-proliferating human CASMC, AoSMC and CAEC were readily transduced with transduction efficiencies approaching 100% at an MOI of 10 as shown in FIGS. 5A and 5B. Similar results were obtained with proliferating CASMC, AoSMC and CAEC.

EXAMPLE VII

Inhibition of Smooth Muscle Cell Growth by CDK Inhibitors

For the growth inhibition studies with growth arrested (i.e., synchronously growing) cells, CASMC's were seeded at 1.3 or 3×10$^4$ cells/well in 24 well plates in the appropriate media supplemented with 5% FBS. Twenty-four hours later, the media was changed to low serum conditions (media with 0.05% FBS) to growth arrest the cells. After 48 hours, cells were infected in low serum conditions with adenoviruses encoding the CDK inhibitor (ΔE1/ΔE3-AV-CKI) transgene or transgene encoding no protein (ΔE1/ΔE3-AV-CMV, or simply AV-CMV, which contains only the CMV promoter) at MOI's of 1, 10, 50, 100 and 250 in duplicate wells. After 24 hours, virus was removed and fresh media containing 10% FBS was added back. The cells were harvested three days later and counted to determine cell recovery, or evaluated for DNA content. Apoptosis was assessed by TdT assay (Phoenix Flow Systems, San Diego, Calif.) and annexin binding assay (R&D Systems, Minneapolis, Minn.).

Uninfected synchronized CASMC underwent approximately a 6-fold expansion in a three day period (FIG. 6). ΔE1/ΔE3-AV-W9, encoding the p27$_{25\text{-}93}$-p16 fusion protein, was the most potent inhibitor of vascular smooth muscle cells, and demonstrated complete CASMC growth arrest at an MOI of 10, which coincided with the MOI sufficient to achieve complete adenovirus transduction of a population of CASMC (FIG. 6). ΔE1/ΔE3-AV-W7, which encodes the p27$_{12\text{-}178}$-p16 fusion protein, demonstrated complete inhibition of synchronized CASMC at a 5 to 10 fold higher MOI. The extent of inhibition with ΔE1/ΔE3-AV-p27, ΔE1/ΔE3-AV-p27$_{12\text{-}178}$, and ΔE1/ΔE3-AV-p27$_{25\text{-}93}$ was similar to that observed with ΔE1/ΔE3-AV-W3.

At an MOI of 50, transduction with ΔE1/E3-AV-p16 resulted in a complete blockade of CASMC proliferation (FIG. 6). There was, however, some variability in relative activities of p16 and p27 from CASMC donor to donor. This inhibition profile may indicate the existence of a threshold mechanism of p16 inhibition that is operative in vivo. In all experiments involving CASMC, ΔE1/ΔE3-AV-W9 was the most active anti-proliferative agent. In this experiment, E1/ΔE3-AV-p16 showed an inhibitory effect at MOI of 50 (FIG. 6). ΔE1/ΔE3-AV-W7, which encodes the $p27_{12-178}$-p16 fusion protein, demonstrated complete inhibition at 100 MOI. ΔE1/ΔE3-AV-W9 had the strongest effect in blocking cell growth following infection in quiescent CASMC. The virus particle to plaque forming units for ΔE1/ΔE3-AV-p16, ΔE1/ΔE3-AV-p27, ΔE1/ΔE3-AV-W7 and ΔE1/ΔE3-AV-W9 were similar (305 vp/pfu, 267 vp/pfu, 141 vp/pfu and 197 vp/pfu respectively). The primacy of AV-W9 was observed in three independent experiments in which CASMC from three different donors were tested (data from one experiment is shown in FIG. 6). Some variation was observed from donor to donor in the relative strength of inhibition by ΔE1/ΔE3-AV-p16 or ΔE1/ΔE3-AV-p27 alone. In all donors, however, ΔE1/ΔE3-AV-W9, ΔE1/ΔE3-AV-W7, and ΔE1/ΔE3-AV-W3 had inhibitory effects. Importantly, the effect of ΔE1/ΔE3-AV-W9 was clearly cytostatic and not cytocidal since CDKi induction of SMC apoptosis was not observed as assayed by annexin and propidium iodide staining and analyzed by FACS.

EXAMPLE VIII

ΔE1/ΔE3 AV-W9 transduction Induces a Blockage of Smooth Muscle Cells in $G_1$, Phase and a Loss of Cells in S Phase The point in the cell cycle in which the ΔE1/ΔE3-AV-CDKi's transduced CASMC were growth arrested was determined by quantification of the cellular DNA content by FACS analysis. CASMC were transduced with ΔE1/ΔE3-AV-CDKi. Three days after restimulation, cells were washed once with PBS and fixed in 70% EtOH for at least 4 hours. Cells were then washed once with PBS and treated with 0.1% triton X-100, 200 μg/ml RNase A and 50 μg/ml propidium iodide in PBS at 37 ° C. for 15 minutes. Cells were analyzed on FACscan using Cell Quest software (Becton Dickinson, Santa Clara, Calif.). Cell cycle analyses were performed using ModFit LT software (Verity, Topsham, Me.). As controls for cell cycle analysis, cells were treated with n-butyrate or aphidicolin, which arrest cells in early $G_1$ (Darzynkiewicz et al. (1981) *Exp. Cell. Res.* 136(2): 279–293) or early S phase (Sorscher and Cordeiro-Stone (1991) *Biochemistry* 30(4): 1086–1090), respectively. 5 mM n-butyrate or 5 mg/ml aphidicolin was added to SMC at the time of restimulation, and cells were collected 36 hours later for analysis of DNA content.

Following incubation in low serum conditions, greater than 98% of SMC were synchronized in the $G_0/G_1$ phase (FIG. 7A, top panel, Serum Low). This block was similar to cells treated with n-butyrate, which blocks cell cycle progression in the early $G_1$ phase and entry into S phase of the cell cycle (Kruh, J. (1982) *Mol Cell Biochem* 42: 65–82) (FIG. 7A, top panel, Early $G_1$ Block). Upon stimulation of the synchronized CASMC with complete media, the normal profile of cells in $G_0/G_1$ phase, S phase and $G_2/M$ phase was observed; 71%, 18% and 11%, respectively (FIG. 7A, top panel, Mock Control).

As predicted from the experiments shown in FIG. 6, transduction with ΔE1/ΔE3-AV-W9 had a profound effect on the cell cycle of CASMC. CASMC transduced with the ΔE1/ΔE3-AV-W9 at MOI of 10 showed complete block of entry into the $G_2/M$ phase; >1% for ΔE1/ΔE3-AV-W9 as compared to 11% in Mock (FIG. 7A; W9, compared gray FACS to mock control solid line overlay). At lower MOI, transduction with ΔE1/ΔE3-AV-W9 initially induced an increase in the population of cells in S phase (47%) (FIG. 7B, middle panel), similar to that observed with the aphidicolin treatment which blocks cells in early S phase (FIG. 7A, top panel, Early S Block). At higher MOI of 50 and 100, however, the percentage of cells in S phase decreased and the fraction of CASMC arrested in Go/Gl phase increased to over 80% (FIG. 7B, lower panel). A similar pattern of growth arrest was observed with the ΔE1/ΔE3-AV-W7 transduced cells but at 5 fold higher MOI. Transduction with "empty" adenovirus, which demonstrated only modest inhibition of CASMC proliferation (FIG. 7A, Null), similarly had little effect on reducing the population of cells in $G_2/M$ even at MOI of greater than 100 (FIGS. 7A and 7B, Null).The ΔE1/ΔE3-AV-p27, ΔE1/ΔE3-AV-$p27_{12-178}$, ΔE1/ΔE3AV-$p27_{25-93}$, and ΔE1/ΔE3-AV-W3 induced a depletion of the $G_2/M$ population and a corresponding increase in the percentage of cells in S phase, although at MOI's 10 to 100 fold higher than necessary for ΔE1/ΔE3-AV-W9.

Thus, as might be expected from the anti-proliferative activity data, the W9 and W7 CDKi's were readily distinguished in analysis of their impact on CASMC cell cycle progression. Transduction of CASMC with any of the ΔE1/ΔE3-AV-p27-p16 fusion CDKi's as well as ΔE1/ΔE3-AV-p27 and ΔE1/ΔE3-AV-p27 derivatives lead to blockade of cells in S phase and loss of the cells in $G_2/M$ phase. Transduction with AV-W9, however, led to blockade of cells in $G_1$ phase and loss of the cells in S phase. At higher MOI's, ΔE1/ΔE3-AV-W7 produced a similar effect. This raises the possibility that at lower concentrations W9 and W7 primarily block CDK's whose activity is required for S-phase progression (CDK2/cyclin E or CDK2/cyclin A) and at higher concentrations, block the activity of CDK's whose activity is required in $G_1$ and at $G_1/S$ (Cdk4,6/cyclin D and Cdk2/cyclin E).

As cell hyper-proliferation is at the center of many human pathologies, including angioplasty associated restenosis, controlling cell proliferation is a critical therapeutic target. Prevention of the SMC proliferation that leads to vessel restenosis through gene therapy with CDKi's at the time of angioplasty, would offer a local-regional therapy with minimal systemic toxicity. While several groups have shown that various CDKi's and other cell cycle regulators do prevent restenosis in animal models, the creation of novel CDKi proteins with increased potency increases the likelihood of success of a CDKi vascular gene therapy strategy. By combining the activity of multiple CDKi, and eliminating regions that potentially limit their activity, regulators of the cell cycle with improved biological activity have been created.

EXAMPLE IX

Inhibition of Endothelial Cell Growth by CDK Inhibitors

For the growth inhibition studies with growth arrested (i.e., synchronized) cells, CAEC's were seeded at 1.3 or $3\times10^4$ cells/well in 24 well plates in the appropriate media supplemented with 5% FBS. Twenty-four hours later, the media was changed to low serum conditions (media with 0.05% FBS) to growth arrest the cells. After 48 hours, cells were infected in low serum conditions with ΔE1, ΔE3 recombinant adenoviruses encoding the CDK inhibitor (ΔE1/ΔE3-AV-CDKi), or simply AV-CDKi transgene or transgene encoding no protein (ΔE1/ΔE3-AV-CMV; "AV-Null") at MOI's of 1, 10, 50,100 and 250 in duplicate wells. After 24 hours, virus was removed and fresh media containing 10% FBS was added back. The cells were harvested 3 days later and counted to determine cell recovery, or evaluated for DNA content.

For growth inhibition studies with proliferating (i.e., asynchronous) cells, CAEC were plated at $5 \times 10^4$ per well in six-well plates. After 24 hours, cells were infected with 10 MOI ΔE1/ΔE3-AV-CDKi or ΔE1/ΔE3-AV-CMV. Cells were harvested 2 days later and counted to determine cell growth. Apoptosis was assessed by TdT assay (Phoenix Flow Systems, San Diego, Calif.) and annexin binding assay (R&D Systems, Minneapolis, Minn.).

ΔE1/ΔE3-AV-W9 was observed to be the most potent inhibitor of endothelial cell proliferation using primary CAEC that had been growth arrested following serum deprivation (FIG. 8A). In these experiments however, ΔE1/ΔE3-AV-W9 not only inhibited cell proliferation, but also resulted in cell loss. The empty adenoviral vector (Null) induced less significant cell losses. When the experiment was repeated with proliferating endothelial cells that had not been growth arrested, W9 inhibited CAEC proliferation, while the ΔE1/ΔE3-AV-p16 and ΔE1/ΔE3-AV-CMV viruses had little effect (FIG. 8B). As observed with the SMC, there was not evidence of apoptosis following infection in either synchronized or proliferating EC as determined by Tunnel staining of DNA fragments or by annexin binding. Similar results were obtained with human aortic endothelial cells.

EXAMPLE X

Rabbit Liver Toxicity and Transgene Expression Studies of Recombinant Adenoviruses Lacking the E1Region or Lacking Both the E1 and the E4 Regions A replication-defective recombinant adenovirus lacking both the E1 and the E4 regions has recently been described (see Wang et al., U.S. patent application Ser. No. 08/552, 829, filed Nov. 3, 1995, the entirety of which is hereby incorporated by reference). This adenovirus results in reduced pathologic effects and prolonged expression of the transgene. Moreover, the ΔE1/ΔE4 adenovirus can accommodate large transgene(s) than the singly deleted (i.e., ΔE1) adenovirus.

A ΔE1/ΔE4 adenovirus encoding W9 was generated using the methods and cells generally described in Wang et al., U.S. patent application Ser. No. 08/552, 829, filed Nov. 3, 1995. Because deletion of the adenovirus E4 region is a lethal mutation to adenoviruses, these recombinant adenoviruses were packaged in a 293-E4 cell, which is stably transfected with nucleic acid comprising the entire adenovirus E4 region under the control of the inducible promoter. The only adenovirus E4 region protein expressed by this E4 region-deleted adenoviruses was the E4orf4 protein, and that in very low amounts.

In order to study the toxicity of of the ΔE1/ΔE4 adenovirus, a comparison was made between the ΔE1/ΔE4 Adenovirus and ΔE1 Adenovirus delivery in the rabbit carotid artery using the vascular occlusive disease model. Thus, a ΔE1/ΔE4 adenovirus encoding the E. coli β-galactosidase gene (β-gal) under the control of the mouse phosphoglycerate kinase (PGK) promoter was generated. A ΔE1 adenovirus encoding β-gal was similarly generated. Viral stocks were purified by double cesium chloride gradient centrifugation and dialyzed against PBS. The stocks were stored in PBS containing 10% glycerol and 50 mg/ml human serum albumin. Infectious virus titer was determined by titration on 293 cells (see Wang et al. (1995) Gene Ther. 2: 775–783; Wang et al. (1997) Gene Ther. 4: 393–400).

To do this, male New Zealand white rabbits (2–2.5 kg) were maintained on a normal diet. Anesthesia was induced in Ketamine and Xylazine subcutaneously.

Rabbits underwent gene transfer to both carotid arteries via arteriotomy. Purified virus preparations were diluted with Dulbecco's modified Eagle's medium (DME)/virus storage medium to ensure equal composition of virus solutions at different viral titers. Sham infections were carried out using DMV/virus storage medium alone. Approximately 200 μl of virus solution was infused per vessel, which is sufficient to expand the vessel to physiologic dimensions. The solution was allowed to dwell for 15 minutes, then removed. The artery was then flushed with DME/virus storage medium and the arteriotomy closed.

Vessels were harvested at various time points. Briefly, the animals were anesthetized, heparinized (700 IU i.v.), and the carotid arteries dissected free. Animals were then killed with 100 mg/kg IV pentobarbitol. Vessels were immediately excised and washed in phosphate buffered saline (PBS). Segments from all vessels were 1) immediately frozen at −80° C. for protein extraction, 2) rapidly processed for frozen sections and immunohistochemistry, or 3) were hung without delay in organ baths for vasomotor studies.

For the immunohistochemistry studies, arterial frozen sections and paraffin-embedded sections were prepared. Immunohistochemistry for lymphocytes or macrophages was performed using antibodies directed against rabbit CD18 (Serotec, Oxford, UK) 18, rabbit CD43 (TII/1 35, Serotec)II or rabbit RAM 11 18 (Dako, Carpenteria, Calif.), respectively. Vascular cell adhesion molecule—I antibodies were raised against rabbit VCAM-1 and ICAM-1. Immunostaining of smooth muscle cells (HHF 35, Dako, Carpenterial Calif.) and endothelial cells (anti-von Willebrand's factor was also performed. Briefly, frozen sections were dried at room temperature, then equilibrated in PBS. Blocking solution (1.5% horse serum in PBS) was applied for 1 hour at room temperature or overnight at 4° C. Antibodies were diluted in blocking solution at the manufacturer's recommended concentration and were applied to issue sections for 1 hour. Endothelial inflammatory cell infiltration was assessed by counting the total number of CD18+, CD43+, or RM11+ leukocytes adherent to the lumenal surface. In addition, staining intensity was quantified with and image analysis system (Olympus IX70 inverted microscope, Optronics DE1-750 image capturing hardware, Adobe Premiere, and NIH Image 1.61 software).

For vasomotor studies, 5 mm arterial rings were mounted in 30 ml organ baths containing oxygenated (95%$O_2$, 5% $CO_2$) Krebs-Henseleit buffer at 37° C. and used in isometric tension studies. Briefly, cumulative does-response curves to phenylephrine (PE; $10^{-9}$ to $10^{-4}$ M) were established; vessels were then submaximally precontracted with PE (usually $3 \times 10^4$ M), and endothelial function was evaluated by vascular relaxation in response to acetylcholine (Ach, $10^{-8}$ to $10^{-4}$ M). The arteries were then washed, submaximally precontracted with PE, and endothelium-independent relaxation responses to sodium nitroprusside (SNP-, $10^{-8}$ to $10^{-4}$ M) were determined. Statistical significance was assessed by ANOVA.

For systemic toxicological analyses in the adenovirus delivery studies, serum was collected from rabbits that were either sham infected of transduced with either the ΔE1-AV or ΔE1/ΔE4-AV at 3, 10, or 28 days after transduction were tested for levels of liver transaminases (glutamic pyruvic transaminase (sGPT) and glutamic oxalacetic transaminase (sGOT), creatinine, and alkaline phosphatase. All test reagents were obtained from Sigma (St. Louis, Mo.). Serum from a mouse that received partial hepatectomy (induced liver damage) served as positive controls for sGPT/sGOT assays. The positive control for the creatinine assay was obtained from Sigma (St. Louis, Mo.).

As shown in FIGS. 9A and 9B, the ΔE1/ΔE4-AV-β-gal transduced rabbit carotid arteries showed significantly improved transgene (i.e.,β-gal) expression as compared to rabbit carotid arteries transduced with ΔE1-AV-β-gal. The ΔE1/ΔE4-AV-β-gal and the ΔE1-AV-β-gal were identical except that the former lacked the E4 region. Viral preparations from each were both carefully matched for lacZ-forming units in vitro, and were within 10% of one another in viral particle number.

In uninjured rabbit carotid arteries, both ΔE1/ΔE4-AV-β-gal and the ΔE1-AV-β-gal were effective in transducing vascular endothelium (FIGS. 9A and 9B). With both viruses, at least 80% of the endothelial cells were lacZ positive three days following gene transfer (FIGS. 9A and 9B). No medial transfer was observed with either virus, and no lacZ positive cells wre seen in any sham-treated artery.

By 10 days after gene transfer, the number of β-gal positive endothelial cells had declined considerably. However, there was a clear difference between ΔE1/ΔE4-AV-β-gal and the ΔE1-AV-β-gal treated arteries, with about 30% of the endothelial cells transduced with ΔE1/ΔE4 AV-β-gal still lacZ positive after 10 days as compared to only 5% of endothelial cells transduced with ΔE1-AV-β-gal (FIG. 9B). At 28 days after gene transfer, β-gal expression was no longer detectable in any artery (FIG. 9A).

To further quantify β-gal expression an ELISA was performed on whole vessel lysates. β-gal expression was compared at low dose, middle dose, and high dose at 3, 10, and 28 days after gene transfer with ΔE1/ΔE4-AV-β-gal or ΔE1-AV-β-gal. While there was an increase in transgene expression with increasing dose of virus, the effect was surprisingly relatively modest. For both the ΔE1/ΔE4-AV-β-gal and the ΔE1-AV-β-gal, a 25-fold increase in viral dose produced only a 2-fold dose increase in β-gal expression. In spite of this, there appeared to be little difference in gene expression between the two vectors, which confirmed that the titers and transduction conditions were essentially equal between ΔE1/ΔE4-AV-β-gal and the ΔE-AV-β-gal.

Differences in the durability of transgene expression was also observed between ΔE1/ΔE4-AV-β-gal and ΔE1-AV-β-gal. Although transgene expression and the number of β-gal positive cells decreased from day 3 to day 10, β-gal expression at the interim time point of 10 days was significantly higher in the ΔE1/ΔE4-AV-β-gal-treated vessels at all virus doses tested. For the middle dose of $5 \times 10^9$ ffu/ml there was a greater than 4 fold difference in β-gal protein between the ΔE1/ΔE4-AV-β-gal and the ΔE1-AV-β-gal-treated vessels. At the highest dose of $2.5 \times 10^{10}$ ffu/ml, the difference was only 1.5 fold. by day 28, β-gal staining and protein expression was negligible in vessels treated with either ΔE1/ΔE4-AV-β-gal or ΔE1-AV-β-gal (see FIG. 9A). Thus, transgene expression with the ΔE1/ΔE4-AV-β-gal virus was prolonged as compared to that observed with the ΔE1-AV-β-gal virus.

To compared the degree of endothelial activation induced by ΔE1/ΔE4-AV-β-gal and ΔE1-AV-β-gal, arterial cryosections were compared for expression of adhesion molecules, ICAM and VCAM, by immunohistochemistry (FIGS. 10A). In middle dose-treated arteries 10 days following gene transfer, clear differences were observable between sham treated, ΔE1/ΔE4-AV-β-gal-treated, and ΔE1-AV-β-gal-treated arteries. The same relationships were apparent at 3 days post-gene transfer (FIG. 10B). FIGS. 10B–C shows the quantitation of ICAM and VCAM expression using image analysis. The intensity of ICAM and VCAM staining induced by the ΔE1-AV-β-gal virus was between 3–8 times the staining of the ΔE1/ΔE4-AV-β-gal-treated arteries. These differences were statistically significant (FIGS. 10B–C; p<0.01). Although substantially lower than the ΔE1-AV-β-gal-treated arteries, the ΔE1/ΔE4 AV-β-gal-treated arteries showed higher adhesion molecule expression than sham treated arteries (FIGS. 10B–C).

Since first generation recombinant adenoviruses have been shown to induce titer-dependent infiltration of neutrophils, leukocytes, and monocytes (REF), we evaluated cellular infiltration by immunohistochemistry staining for two white blood cell markers, CD18 and CD43 to determine whether the ΔE1/ΔE4-AV-β-gal virus induced less vascular inflammation than the ΔE1-AV-β-gal virus. As shown in FIG. 11A, substantially fewer CD18 and CD43 positive cells were present in ΔE1/ΔE4-AV-β-gal-treated arteries as compared to arteries treated with ΔE1-AV-β-gal virus. This difference was quantitated both by cell counting (data not shown) and image analysis (FIG. 11B). As was the case for adhesion molecule expression (FIGS. 10A–C), the ΔE1/ΔE4-AV-β-gal virus induced significantly greater inflammatory cell infiltration than did sham-treatment, but induced significantly less inflammatory cell infiltration than the ΔE1-V-β-gal virus. This pattern was also observed with RAM 11 stained arteries (data not shown).

Recombinant first generation adenovirus (ΔE1-AV) impairs endothelium-dependent relaxation in a titer-dependent manner that corresponds closely to the degree of inflammation (REF); however, there is no effect on vascular smooth muscle cell contraction or sodium nitroprusside-induced relaxation. To determine whether the ΔE1/ΔE4-AV virus produced less function endothelial impairment, the vasomotor function of carotid arteries in organ baths at 3, 10, and 28 days following gene transfer was evaluated. Phenylephrine-induced contraction and SNP-induced relaxation were the same in all vessels, regardless of treatment (data not shown). However, the ΔE1-AV virus significantly impaired endothelium-dependent relaxation at all time points (FIG. 12). In contrast, as shown in FIG. 12, the ΔE1/ΔE4-AV virus had little impact on endothelium-dependent relaxation. Only at high titer was there any significant impairment observed, and even then, only at the 10 day time point.

In ΔE1-AV treated vessels receiving the middle dose, intimal hyperplasia was readily apparent as early as 10 days following gene transfer (FIG. 13A), and progressed to nearly double the 10-day thickness by 28 days after gene transfer (FIG. 13B). Intimal hyperplasia in ΔE1/ΔE4-AV-treated arteries was reduced by a factor of three relative to the ΔE1-AV-treated arteries (see FIG. 13C). All arteries receiving either middle or high-titer adenovirus doses showed significantly greater intimal hyperplasia than sham-treated arteries at both 10 and 28 days (FIGS. 13A, 13B, and 13C).

FIGS. 14A–14D show the results of the systemic toxicological analyses in the adenovirus delivery studies, which indicated that the serum enzymes did not significantly change following virus delivery to the carotid artery at any of the time points, where d3 indicates 3 days after transduction; d10 indicates 10 days after transduction.; and d28 indicates 28 days after transduction. Furthermore, there were no differences between ΔE1-AV and ΔE1/ΔE4-AV. Thus, in spite of the observed increases in vessel inflammatory cell infiltrates (FIGS. 11A and 11B), there was no apparent increase in the serum levels of liver transaminases, sGPT and SGOT, or creatinine or alkaline phosphatase in either the ΔE1/ΔE4-AV-β-gal or the ΔE1-AV-β-gal-treated vessels, suggesting the absence of any broad systemic toxicity following vascular delivery with either ΔE1-AV and ΔE1/ΔE4-AV. These results indicated that liver and renal functions were normal and support the absence of systemic toxicity due to either ΔE1-AV and ΔE1/ΔE4 AV virus.

EXAMPLE XI

A Recombinant Adenovirus Lacking the E1 and E3 Regions and Expressing the W9 Fusion Protein has Smooth Muscle Cell Proliferation-Inhibiting Activity In Vivo ΔE1/ΔE3 AV-W9 was delivered to balloon-injured rabbit carotid arteries to determine efficacy of the CDKi chimeric molecule for the prevention of restenosis. To do this, male New Zealand white rabbits (2–2.5 kg) were maintained on a normal diet. Anesthesia was induced in Ketamine and Xylazine subcutaneously. Prior to balloon injury, rabbits were fed a 1% cholesterol diet for six weeks. Three to four animals were tested in each treatment group (sham, control virus or test virus).

For in vivo gene transfer to injured artery, rabbits were placed under appropriate anesthesia. A midline incisions was made and the external carotid artery was exposed. An arteriotomy was performed, and a 2F Fogarty balloon catheter was inserted and inflated (50–60 μl saline to fill the balloon) and passed 5x. The catheter was then removed and the animals were recovered. Three days later, rabbits underwent gene transfer (by transduction with recombinant retrovirus) to both carotid arteries via arteriotomy. The vessel was clamped and an arteriotomy performed. Approximately 100 μl of virus solution was infused per vessel, which is sufficient to expand the vessel to physiologic dimensions. The solution was allowed to dwell for 15 minutes then removed. The artery was then flushed with DME/virus storage medium and the arteriotomy closed. The clamps were removed and circulation restored.

High titer viral stock was diluted with Dulbecco's modified Eagle's medium (DME)/virus storage medium at 1:1 ratio (final viral particle titer $2.5 \times 10^{12}$ vp/ml) to ensure equal composition of virus solutions at different viral titers. Sham infections were carried out using DMV/virus storage medium alone.

Vessels were harvested at 14 days after gene transfer. Briefly, animals were anesthetized, heparinized (700 IU i.v.), and the carotid arteries dissected free. Animals were then euthanized with 100 mg/kg IV pentobarbitol. Vessels were immediately excised and washed in phosphate buffered saline (PBS). The excised segments were approximately 2.0–2.5 cm total and were cut into six segments. Segments were snap frozen for DNA or protein for PCR or Western blot analyses. The first and third segments were processed for histology and immunohistochemistry.

For immunohistochemistry, arterial frozen sections and paraffin-embedded sections were prepared. Immunostaining was performed on sections to detect for transgene expression using the HA antibody (the CDKi transgenes in these viruses contain an HA tag at the N terminal of the protein) from Babco and for PCNA expression (Dako). Briefly, frozen sections were dried at room temperature, then equilibrated in PBS. Blocking solution (1.5% horse serum in PBS) was applied for 1 hour at room temperature or overnight at 4° C. Antibodies were diluted in blocking solution at the manufacturer's recommended concentration and were applied to tissue sections for 1 hour. The extent of neointimal hyperplasia was visualized following Voerhoff's stain or Masson Accustain Kit (Sigma).

Neointimal thicknesses and immunostaining intensity was quantified with and image analysis system (Olympus IX70 inverted microscope, Optronics DE1-750 image capturing hardware, Adobe Premiere and NIH Image 1.61 software). The results were quantified either by cell count or image analysis. For the analyses, 2 vessels per rabbit were treated. From each vessel, 2–3 sections were stained. Four to six views per section (20X) and 2–3 points per view taken for measurements. The extent of neointimal proliferation following the second balloon injury and viral infection was determined by measuring the neointimal thickness (μm) per HPF (high power field).

Three different strategies were tested using this example. For all three studies, the rabbits were given a 1% cholesterol diet for six weeks. Vessels were harvested two weeks after gene transfer. The first two rabbit studies were to test efficacy of ΔE1/ΔE3-AV-W9 in a double balloon injury model. The third study was to test efficacy in a single balloon injury model. Table II shows a summary of the experimental strategies in the rabbit carotid artery balloon injury model of this example.

TABLE II

| Rabbit Study 1 | 1st Balloon injury, wait 2 weeks, 2nd balloon injury plus gene transfer |
| Rabbit Study 2 | 1st Balloon injury, wait 1 week, 2nd balloon injury plus gene transfer |
| Rabbit Study 3 | 1 balloon injury followed by gene transfer 3 days later |

From these studies, the following results were obtained:

RABBIT STUDY 1

Double Balloon Injury Model with Second Balloon Injury Plus Gene Transfer 2 Weeks After First Balloon Injury ΔE1/ΔE3 AV-W9 was delivered to balloon-injured rabbit carotid arteries to as an initial study to determine efficacy of the CDKi chimeric molecule for the prevention of restenosis. A first balloon injury was performed to the rabbit carotid artery to induce smooth muscle cell proliferation. A second balloon injury and delivery of $1 \times 10^9$ pfu (plaque forming units) ΔE1/ΔE3-AV-W9 was performed two weeks after the first injury. The vessels were harvested 14 days later. The extent of neointimal proliferation following the second balloon injury and viral transduction was determined by measuring the neointimal thickness (μm) per HPF (high power field). The results shown in FIGS. 15A and 15B demonstrated that there was a 40–50% inhibition of neointimal hyperplasia when ΔE1/ΔE3-AV-W9 was used to transduce the cells as compared to cells that had been sham-infected. These results are positive at a low dose of p27/p16 fusion in the first generation adenovirus (i.e., the ΔE1/ΔE3-AV).

RABBIT STUDY 2

Double Balloon Injury Model with Second Balloon Injury Plus Gene Transfer 1 Week After First Balloon Injury FIG. 16A shows sections of the carotid artery that were either untreated or treated with ΔE1/ΔE3-AV-β-gal control virus or ΔE1/ΔE3-AV-W9. Approximately $2.5 \times 10^{11}$ viral particles were introduced to the carotid artery and used to transduce the smooth muscle cells of this artery after the second balloon injury. The arrows in FIG. 16A indicate the extent of neointimal hyperplasia. The graph is a quantification of the percentage of reduction in neointimal hyperplasia following ΔE1/ΔE3-AV-W9 infection compared to control.

33

RABBIT STUDY 3

Single Balloon Injury Model with Gene Transfer Three Days After Balloon Injury

FIGS. 17A and 17B show the results from the third study which indicated a 50% reduction in intimal hyperplasia when approximately $2.5\times10^{11}$ viral particles of ΔE1/ΔE3-AV-W9 was delivered just 3 days following the first balloon injury, as compared to sham-infection.

Taken together, the results shown in FIGS. 15A–17B from all three studies indicate that the p27/p16 fusion is efficacious for reducing neointimal formation in the rabbit balloon injury model. Thus, results from the first and second studies (i.e., the Double Balloon Injury Models) showed that intimal hyperplasia was reduced by 45% following the second balloon injury and gene transfer compared with sham or control virus treated arteries (p<0.001). In the third study (i.e., the Single Balloon Injury Model), intimal hyperplasia was reduced by 50% following a single balloon injury.

In addition, in the third rabbit study (i.e., the Single Balloon Injury Model), the impact of ΔE1/ΔE3-AV-W9 on PCNA (a maker of cell proliferation) was also evaluated. Below are the results following immunohistostaining of vessels with anti-PCNA antibody (commercially available from Dako). Cells were counterstained with hematoxylin to visualize nuclei.

FIG. 18A shows that the number of PCNA positive cells was significantly reduced in vessels that received ΔE1/ΔE3-AV-W9. Quantification of this staining (by cell count) indicated a 50% reduction in PCNA positive cells (see FIG. 18B). This correlated with the 50% reduction in neointimal proliferation (see, eg., FIG. 17B), further supporting an inhibition of SMC growth following balloon injury.

EXAMPLE XII

Comparison of ΔE1/ΔE3-AV-W9 with ΔE1/ΔE3-AV-p16 and ΔE1/ΔE3-AV-p27

The efficacy of ΔE1/ΔE3-AV-W9 was compared with the ΔE1/ΔE3-AV-p16 and ΔE1/ΔE3 AV-p27 which encode the individual parental molecules. Rabbits were treated the same as described for the Single Balloon Injury Model described in Example XI. Three days following the single balloon injury, vessels received equivalent viral particles ($2.5\times10^{11}$ v.p.) of ΔE1/ΔE3-AV-W9, ΔE1/ΔE3-AV-p16, or ΔE1/ΔE3 AV-p27. Vessels were harvested either 3 days or 2 weeks after gene transfer. Arterial sections were analyzed for neointimal proliferation, transgene expression, and PCNA expression.

FIG. 19 shows the results of quantification of neointimal proliferation in carotid artery segments. The results show that transduction with ΔE1/ΔE3-AV-W9, which reduced neointimal proliferation by 50%, was significantly more potent than ΔE1/ΔE3-AV-p16 or ΔE1/ΔE3-AV-p27 alone (FIG. 19). ΔE1/ΔE3-AV-p16 or ΔE1/ΔE3-AV-p27 alone demonstrated 20–30% inhibition in neointimal hyperplasia compared to sham or control virus treated vessels (FIG. 19).

The carotid artery vessels were also analyzed for transgene expression by staining with an anti-HA antibody (Babco), since the ΔE1/ΔE3-AV-CDKi adenoviruses used in these studies encode the CDKi proteins p16, p27 or W9 (p27/p16) fused to an HA (hemagglutinin peptide) tag (see Example III). Therefore, transgene expression can be detected by the HA antibody. Immunostaining was performed on vessels taken three days after gene transfer.

As shown in FIG. 20A, segments taken from animals which received with ΔE1/ΔE3-AV-W9, ΔE1/ΔE3-AV-p16,

34 or ΔE1/ΔE3-AV-p27 stained positive for the hemagglutinin tag, indicating the smooth muscle cells of these animals were indeed transduced and expressed W9, p16, and p27, respectively.

FIG. 20B shows the quantification of the transgene expression. The amount of transgene expression was quantified by image analyses. Positive cells were detected with the HA-antibody.

The level of PCNA expression was examined in rabbit artery at both 3 days and 2 weeks after gene transfer. PCNA expression decreased in vessels that received ΔE1/ΔE3-AV-p16, ΔE1/ΔE3-AV-p27, and ΔE1/ΔE3-AV-W9 (FIG. 21). Thus, PCNA expression was reduced in injured carotid arteries treated with ΔE1/ΔE3-AV-CDKi. As shown in FIG. 21, ΔE1/ΔE3-AV-W9 (black bars) had a significant reduction in PCNA expression as compared to ΔE1/ΔE3-AV-p16 (gray bars) or ΔE1/ΔE3-AV-p27 (cross-hatched bars) alone. The levels of PCNA expression were down in all vessels by 2 weeks after gene transfer indicating that the SMC proliferation that occurs in response to injury was nearly finished.

EXAMPLE XIII

Efficacy of Recombinant Adenovirus Delivery of W9 in a Rabbit Vein Graft Model

Efficacy of ΔE1/ΔE3-AV-W9 was also tested in a vein graft model. In this experiment, the external jugular vein was excised and grafted onto the carotid artery. The vessel was clamped at both ends and virus solution was delivered to the grafted vein for 15 minutes. Virus was then removed and clamps released and circulation restored. The vein graft was harvested 10 days following gene transfer and analyzed for the extent of adventitial hyperplasia and morphological changes. Adventitial thickening was assessed by weight gain of the vein graft. As shown in FIGS. 22A and 22B, transduction with approximately $1\times10^9$ pfu of AV-W9 resulted in 30% inhibition of adventitial hyperplasia. In addition, the overall cellularity and integrity of the vessel were better preserved following transduction with ΔE1/ΔE3-AV-W9.

EXAMPLE XIV

Smooth Muscle Cell Proliferation-Inhibiting Activity of Recombinant Lentiviruses Expressing CDKi Proteins A second virus-based delivery vehicle for the CDKi proteins of the invention was generated. Here, a lentivirus vector previously described (see Dull et al. (1998) J. Virol. 72: 8463–8471) was used to generate recombinant lentiviruses encoding W9, W7, p16, and p27. Transgenes similar to those described in Example III (i.e., a transgene consisting of CMV enhancer/promoter-CDKi insert-SV40 polyA) were inserted into the lentivirus transfer vector, pRRL.sin-18, between the splice acceptor cite and the 3' LTR (Dull et al., supra). It should be noted, however, that these lentivirus-expressed CDKi did not have the 6 His, HA tag.

The recombinant lentiviruses were packaged essentially as described in Dull et al., supra. The recombinant lentiviruses are used to transduce smooth muscle cells and are administered to rabbit blood vessels following angioplasty in the Single and Double Balloon Injury Models according to the methods generally described above for the recombinant adenoviruses.

In a slight modification, a second form of recombinant lentivirus is generated encoding CDKi fusion proteins of the invention. FIG. 23A illustrates a representative recombinant lentivirus vector containing a W9 expression cassette (i.e., W9-encoding nucleic acid sequence operably linked to regulatory sequences) flanked by HIV LTRS. Downstream of the 5' LTR, the vector contains the HIV leader sequence, the major 5' splice donor site (SD), the packaging sequence (Ψ), the first 43 bps of the HIV gag gene, the HIV Rev Response Element (RRE), and the splice accepter sites (SA) of the second exon of HIV tat and HIV rev. This vector may be packaged according to standard techniques to generate a recombinant lentivirus that encodes W9. Another recombinant lentiviral vector is shown on FIG. 23B. This self-inactivating lentiviral vector contains a W9 expression cassette flanked by a 5' HIV LTR having a substituted U3 region and a 3' HIV LTR, or a 5' HIV LTR and a deleted 3' HIV LTR. This vector further contains downstream from the 5' LTR and HIV leader sequence, the major 5' SD, Ψ, the first 43 bps of the gag gene, the RRE, and the SA of the second exon at tat and rev.

EQUIVALENTS

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the invention is as set forth in the appended claims rather than being limited to the examples contained in the foregoing description.

What is claimed is:

1. A method for inhibiting smooth muscle hyperproliferation, comprising:
   (a) transducing smooth muscle cells with an effective amount of a replication-deficient adenovirus that lacks a functional E1 region and comprises a transgene encoding a cyclin dependent kinase inhibitor (CDKi) and
   (b) wherein the said replication-deficient adenovirus is administered in vitro to cultivated cells, in vivo site specifically, or by vessel infusion at the time of surgery, expressing said transgene in the smooth muscle cells resulting in generation of transduced smooth muscle cells, wherein said transduced smooth muscle cells exhibit a decrease in hyperproliferation and said cyclin dependent kinase inhibitor is a fusion protein consisting of amino acids 25–93 of p27 fused to p16 (SEQ ID NO:14) or a fusion protein consisting of amino acids 12–178 of p27 fused to p16 (SEQ ID NO:20).

2. The method according to claim 1 wherein the fusion protein consists of amino acids 25–93 of p27 fused to p16.

3. The method according to claim 1 wherein the fusion protein consists of amino acids 12–178 of p27 fused to p16.

4. The method of claim 2 or 3 wherein the fusion protein comprises a linker positioned between the p27 and p16 components.

5. The method according to claim 1 wherein the hyperproliferation was induced by injury.

6. The method according to claim 5 wherein the injury was induced by angioplasty.

7. The method according to claim 1 wherein the replication-deficient adenovirus further lacks a functional E4 region.

8. The method according to claim 7 wherein the hyperproliferation was induced by injury.

9. The method according to claim 8 wherein the injury was induced by angioplasty.

10. The method according to claim 7 wherein the fusion protein consists of amino acids 25–93 of p27 fused to p16.

11. The method according to claim 7 wherein the fusion protein consists of amino acids 12–178 of p27 fused to p16.

12. The method of claim 10 or 11 wherein the fusion protein comprises a linker positioned between the p27 and p16 components.

13. The method according to claim 1 wherein the replication-deficient adenovirus further lacks a functional E3 region.

14. The method according to claim 13 wherein the hyperproliferation was induced by injury.

15. The method according to claim 14 wherein the injury was induced by angioplasty.

16. The method according to claim 13 wherein the fusion protein consists of amino acids 25–93 of p27 fused to p16.

17. The method according to claim 13 wherein the fusion protein consists of amino acids 12–178 of p27 fused to p16.

18. The method of claim 16 or 13 wherein the fusion protein comprises a linker positioned between the p27 and p16 components.

19. The method according to claim 7 wherein the replication-deficient adenovirus further lacks a functional E3 region.

20. The method according to claim 19 wherein the fusion protein consists of amino acids 25–93 of p27 fused to p16.

21. The method according to claim 19 wherein the fusion protein consists of amino acids 12–178 of p27 fused to p16.

22. The method of claim 20 or 21 wherein the fusion protein comprises a linker positioned between the p27 and p16 components.

23. A method for inhibiting smooth muscle hyperproliferation, comprising:

(a) transducing smooth muscle cells with an effective amount of a replication-deficient lentivirus, wherein said lentivirus comprises a transgene encoding a cyclin dependent kinase inhibitor (CDKi) and (b) wherein the said replication-deficient adenovirus is administered in vitro to cultivated cells, in vivo site specifically, or by vessel infusion at the time of surgery, expressing said transgene in the smooth muscle cells resulting in generation of transduced smooth muscle cells, wherein said transduced smooth muscle cells exhibit a decrease in hyperproliferation and said cyclin dependent kinase inhibitor is a fusion protein consisting of amino acids 25–93 of p27 fused to p16 or a fusion protein consisting of amino acids 12–178 of p27 fused to p16.

24. The method according to claim 23 wherein the fusion protein consists of amino acids 25–93 of p27 fused to p16.

25. The method according to claim 23 wherein the fusion protein consists of amino acids 12–178 of p27 fused to p16.

26. The method according to claim 24 or 25 wherein the fusion protein comprises a linker positioned between the p27 and p16 components.

* * * * *